US008397756B2

(12) United States Patent
Packham et al.

(10) Patent No.: US 8,397,756 B2
(45) Date of Patent: Mar. 19, 2013

(54) FLUID CONDUIT COUPLERS WITH DEPRESSIBLE LATCH MECHANISM

(75) Inventors: Trent Turner Packham, Fort Collins, CO (US); Francis J. Lombardi, Fort Collins, CO (US); Leonard L. Hofheins, Provo, UT (US); Gregg D. Niven, Kaysville, UT (US); Robert J. Elshof, Fort Collins, CO (US); Raymond L. Townsend, Johnstown, CO (US); Richard W. Cairns, Longmont, CO (US)

(73) Assignee: Nordson Corporation, Westlake, OH (US)

( * ) Notice: Subject to any disclaimer, the term of this patent is extended or adjusted under 35 U.S.C. 154(b) by 238 days.

(21) Appl. No.: 12/893,432

(22) Filed: Sep. 29, 2010

(65) Prior Publication Data

US 2011/0012340 A1    Jan. 20, 2011

Related U.S. Application Data

(63) Continuation of application No. 11/336,587, filed on Jan. 20, 2006, now Pat. No. 7,806,139.

(51) Int. Cl.
*F16L 37/23* (2006.01)
(52) U.S. Cl. ............................ 137/614.05; 285/320
(58) Field of Classification Search ............ 137/614.03–614.05, 594; 285/921, 285/319, 320, 305
See application file for complete search history.

(56) References Cited

U.S. PATENT DOCUMENTS

| 163,261 A | 5/1875 | Ruppenthal |
| 185,896 A | 1/1877 | Curtis |
| 187,982 A | 3/1877 | Pirsson et al. |
| 200,944 A | 3/1878 | Smith |
| 235,580 A | 12/1880 | Smith et al. |
| 327,509 A | 10/1885 | Aldridge |
| 584,008 A | 6/1887 | Munson |
| 465,868 A | 12/1891 | List |
| 725,421 A | 4/1903 | Dinkins |
| 727,982 A | 5/1903 | Ludwig |

(Continued)

FOREIGN PATENT DOCUMENTS

| BE | 479098 | 1/1948 |
| DE | 1868896 | 3/1963 |

(Continued)

OTHER PUBLICATIONS

About Us [online], Thuro Metal Products [retrieved on Apr. 9, 2010], retrieved from the Internet: <URL: http://www.thurometal.com/about.html>, 2 pages.

(Continued)

*Primary Examiner* — Kevin Lee
(74) *Attorney, Agent, or Firm* — Dorsey & Whitney LLP

(57) ABSTRACT

A fluid conduit coupling assembly has a depressible latch mechanism that secures a first fluid conduit to a second fluid conduit via a first coupler and a second coupler. The first coupler connects to the first fluid conduit and the second coupler connects to the second fluid conduit. The depressible latch mechanism is formed by a pair of cantilevered buttons disposed in symmetrically opposed positions on one of the couplers. The cantilevered buttons have engagement lips that extend distally with catches that extend radially outward to engage a ridge formed on an interior wall of the opposing coupler. Fluid ports within the couplers interface when the couplers connect to provide fluid flow between the first and second conduits. Valves may be disposed in each of the couplers to arrest fluid flow when the couplers are detached and automatically open to allow fluid to flow when the couplers are connected.

22 Claims, 53 Drawing Sheets

U.S. PATENT DOCUMENTS

| | | | |
|---|---|---|---|
| 874,957 A | 12/1907 | Godley |
| 884,461 A | 4/1908 | Browne |
| 909,131 A | 1/1909 | Antic |
| 951,889 A | 3/1910 | Teuer |
| D42,368 S | 3/1912 | Mossberg |
| 1,029,819 A | 6/1912 | Nylander |
| 1,033,187 A | 7/1912 | Metzger |
| 1,039,354 A | 9/1912 | Bonadio |
| 1,077,417 A | 11/1913 | McCracken |
| 1,078,112 A | 11/1913 | Storm |
| 1,115,945 A | 11/1914 | Kunz |
| 1,193,446 A | 8/1916 | Wells |
| 1,239,345 A | 9/1917 | Brown |
| 1,255,847 A | 2/1918 | Arkin |
| 1,259,684 A | 3/1918 | Vinten |
| 1,489,310 A | 4/1924 | Critchlow |
| 1,526,218 A | 2/1925 | Johnson |
| 1,578,504 A | 3/1926 | Bronson et al. |
| 1,587,079 A | 6/1926 | Machino |
| 1,767,073 A | 6/1930 | Ingold |
| 1,863,360 A | 6/1932 | Weatherhead |
| 1,950,947 A | 3/1934 | Mulroyan |
| 2,023,428 A | 12/1935 | Liebhardt |
| 2,056,524 A | 10/1936 | Johnson |
| 2,066,473 A | 1/1937 | Jorgensen |
| 2,097,628 A | 11/1937 | Liebhardt |
| 2,099,335 A | 11/1937 | Hansen |
| 2,108,714 A | 2/1938 | Hirsch et al. |
| 2,116,705 A | 5/1938 | Marx et al. |
| 2,139,745 A | 12/1938 | Goodall |
| 2,147,355 A | 2/1939 | Scholtes |
| 2,159,116 A | 5/1939 | Zacharias |
| 2,211,147 A | 8/1940 | Miller |
| 2,257,321 A | 9/1941 | Arnold |
| 2,263,293 A | 11/1941 | Ewald |
| 2,264,815 A | 12/1941 | Thomsen |
| 2,340,119 A | 1/1944 | Graham |
| 2,346,445 A | 4/1944 | Merker et al. |
| 2,352,728 A | 7/1944 | Merker et al. |
| 2,429,782 A | 10/1947 | Versoy |
| 2,432,946 A | 12/1947 | Theunissen |
| 2,470,800 A | 5/1949 | Ashton |
| 2,479,499 A | 8/1949 | Le Clair |
| 2,500,720 A | 3/1950 | Van der Heem |
| 2,507,536 A | 5/1950 | Goodson |
| 2,516,583 A | 7/1950 | Moore |
| 2,535,740 A | 12/1950 | Knopp |
| 2,577,009 A | 12/1951 | Frantz |
| 2,626,974 A | 1/1953 | Howard et al. |
| 2,630,131 A | 3/1953 | Snyder |
| 2,661,018 A | 12/1953 | Snyder |
| 2,701,147 A | 2/1955 | Summerville |
| 2,722,399 A | 11/1955 | Oetiker |
| 2,753,195 A | 7/1956 | Palmer |
| 2,774,616 A | 12/1956 | Dodd et al. |
| 2,790,571 A | 4/1957 | Flaith et al. |
| 2,864,628 A | 12/1958 | Edleson |
| 2,915,325 A | 12/1959 | Foster |
| 2,926,934 A | 3/1960 | Gill |
| 2,931,668 A | 4/1960 | Baley |
| 2,937,892 A | 5/1960 | Prescott, Jr. |
| 2,948,553 A | 8/1960 | Gill et al. |
| 2,967,067 A | 1/1961 | Singer |
| 2,991,090 A | 7/1961 | De Cenzo |
| 3,017,203 A | 1/1962 | Macleod |
| 3,037,497 A | 6/1962 | Roberson |
| 3,046,028 A | 7/1962 | Nathan |
| 3,048,415 A | 8/1962 | Shook |
| 3,073,342 A | 1/1963 | Magorien |
| 3,078,068 A | 2/1963 | Romney |
| D196,473 S | 10/1963 | Hill |
| 3,124,157 A | 3/1964 | Krzewina |
| 3,129,020 A | 4/1964 | Bujnowski |
| 3,171,196 A | 3/1965 | Helitas |
| 3,191,628 A | 6/1965 | Kirkwood et al. |
| 3,217,400 A | 11/1965 | Illesy et al. |
| 3,217,771 A | 11/1965 | Beall et al. |
| 3,227,380 A | 1/1966 | Pinkston |
| 3,237,974 A | 3/1966 | Press |
| 3,245,703 A | 4/1966 | Manly |
| 3,276,799 A | 10/1966 | Moore et al. |
| 3,279,497 A | 10/1966 | Norton et al. |
| 3,314,696 A | 4/1967 | Ferguson et al. |
| 3,317,214 A | 5/1967 | Durgom |
| D209,166 S | 11/1967 | Hunt |
| D209,168 S | 11/1967 | Hunt |
| 3,352,576 A | 11/1967 | Thomas |
| 3,382,892 A | 5/1968 | Cerbin |
| 3,403,930 A | 10/1968 | Bernier |
| 3,432,176 A | 3/1969 | Valenziano |
| 3,448,760 A | 6/1969 | Cranage |
| 3,450,424 A | 6/1969 | Calisher |
| 3,512,808 A | 5/1970 | Graham |
| 3,523,701 A | 8/1970 | Graham |
| 3,538,940 A | 11/1970 | Graham |
| 3,542,338 A | 11/1970 | Scaramucci |
| 3,545,490 A | 12/1970 | Burrus |
| 3,550,626 A | 12/1970 | Daniels et al. |
| 3,560,027 A | 2/1971 | Graham |
| 3,563,265 A | 2/1971 | Graham |
| 3,574,314 A | 4/1971 | Quercia |
| 3,588,149 A | 6/1971 | Demler |
| 3,596,933 A | 8/1971 | Luckenbill |
| 3,599,843 A | 8/1971 | Johnston |
| 3,600,917 A | 8/1971 | Krock |
| 3,649,050 A | 3/1972 | Woodling |
| 3,666,297 A | 5/1972 | Marks |
| 3,690,336 A | 9/1972 | Drum |
| 3,712,583 A | 1/1973 | Martindale et al. |
| 3,747,964 A | 7/1973 | Nilsen |
| 3,750,238 A | 8/1973 | Tanner |
| 3,815,887 A | 6/1974 | Curtis et al. |
| 3,817,561 A | 6/1974 | Kay |
| 3,829,135 A | 8/1974 | Forni |
| 3,876,234 A | 4/1975 | Harms |
| 3,889,710 A | 6/1975 | Brost |
| 3,899,200 A | 8/1975 | Gamble |
| 3,921,656 A | 11/1975 | Meisenheimer, Jr. et al. |
| 3,979,934 A | 9/1976 | Isenmann |
| 3,990,674 A | 11/1976 | Schattenberg |
| 4,025,049 A | 5/1977 | Schmidt |
| 4,039,213 A | 8/1977 | Walters |
| 4,072,330 A | 2/1978 | Brysch |
| 4,099,748 A | 7/1978 | Kavick |
| 4,113,627 A | 9/1978 | Leason |
| 4,116,476 A | 9/1978 | Porter et al. |
| 4,129,145 A | 12/1978 | Wynn |
| 4,142,546 A | 3/1979 | Sandau |
| D252,470 S | 7/1979 | Pawlak |
| 4,181,149 A | 1/1980 | Cox |
| 4,182,519 A | 1/1980 | Wilson |
| D254,505 S | 3/1980 | Parsons et al. |
| 4,200,605 A | 4/1980 | Imamura |
| D255,145 S | 5/1980 | Nederman |
| 4,220,360 A | 9/1980 | Jacek et al. |
| D258,526 S | 3/1981 | Nederman |
| 4,253,687 A | 3/1981 | Maples |
| D259,278 S | 5/1981 | McCaw |
| 4,271,865 A | 6/1981 | Galloway et al. |
| 4,282,175 A | 8/1981 | Volgstadt et al. |
| 4,287,644 A | 9/1981 | Durand |
| 4,294,285 A | 10/1981 | Joslyn |
| 4,296,949 A | 10/1981 | Muetterties et al. |
| 4,319,774 A | 3/1982 | Kavick |
| 4,330,010 A | 5/1982 | Drescher et al. |
| 4,330,142 A | 5/1982 | Paini |
| 4,331,175 A | 5/1982 | Brake et al. |
| 4,331,177 A | 5/1982 | Makishima |
| 4,340,200 A | 7/1982 | Stegmeier |
| 4,345,786 A | 8/1982 | Egert |
| 4,346,703 A | 8/1982 | Dennehey |
| 4,351,351 A | 9/1982 | Flory et al. |
| 4,366,816 A | 1/1983 | Bayard et al. |
| 4,393,548 A | 7/1983 | Herb |
| 4,397,442 A | 8/1983 | Larkin |
| 4,407,526 A | 10/1983 | Cicenas |
| 4,431,031 A | 2/1984 | Ettlinger |

| | | | | | |
|---|---|---|---|---|---|
| 4,431,218 A | 2/1984 | Paul | 5,090,747 A | 2/1992 | Kotake |
| 4,434,121 A | 2/1984 | Schaper | 5,094,482 A | 3/1992 | Petty et al. |
| 4,436,125 A | 3/1984 | Blenkush | 5,104,158 A | 4/1992 | Meyer et al. |
| 4,437,689 A | 3/1984 | Goebel et al. | 5,106,127 A | 4/1992 | Briet |
| 4,439,188 A | 3/1984 | Dennehey | D326,155 S | 5/1992 | Boehringer et al. |
| 4,458,719 A | 7/1984 | Strybel | 5,110,163 A | 5/1992 | Benson et al. |
| 4,489,914 A | 12/1984 | Stevenson et al. | 5,112,084 A | 5/1992 | Washizu |
| 4,489,961 A | 12/1984 | Laidig | 5,114,250 A | 5/1992 | Usui |
| 4,500,118 A | 2/1985 | Blenkush | D326,715 S | 6/1992 | Schmidt |
| 4,527,745 A | 7/1985 | Butterfield et al. | 5,123,677 A | 6/1992 | Kreczko et al. |
| 4,541,457 A | 9/1985 | Blenkush | 5,143,381 A | 9/1992 | Temple |
| 4,541,657 A | 9/1985 | Smyth | 5,160,177 A | 11/1992 | Washizu |
| 4,553,587 A | 11/1985 | Traylor | 5,160,474 A | 11/1992 | Huff |
| D282,962 S | 3/1986 | Gerber | 5,165,733 A | 11/1992 | Sampson |
| 4,580,816 A | 4/1986 | Campbell et al. | 5,169,161 A | 12/1992 | Jones |
| 4,603,888 A | 8/1986 | Goodall et al. | D332,482 S | 1/1993 | Petty et al. |
| 4,603,890 A | 8/1986 | Huppee | 5,176,406 A | 1/1993 | Straghan |
| 4,613,112 A | 9/1986 | Phlipot et al. | 5,178,303 A | 1/1993 | Blenkush et al. |
| 4,616,859 A | 10/1986 | Brunet | 5,181,752 A | 1/1993 | Benson et al. |
| 4,626,001 A | 12/1986 | Lee | D333,178 S | 2/1993 | Novy |
| 4,630,847 A | 12/1986 | Blenkush | 5,190,224 A | 3/1993 | Hamilton |
| 4,632,436 A | 12/1986 | Kimura | 5,222,279 A | 6/1993 | Frano et al. |
| 4,635,972 A | 1/1987 | Lyall | 5,228,724 A | 7/1993 | Godeau |
| 4,645,245 A | 2/1987 | Cunningham | 5,232,020 A | 8/1993 | Mason et al. |
| 4,658,326 A | 4/1987 | Clark et al. | D339,417 S | 9/1993 | Sampson et al. |
| 4,659,116 A | 4/1987 | Cameron | 5,251,025 A | 10/1993 | Cooper et al. |
| 4,694,544 A | 9/1987 | Chapman | 5,273,053 A | 12/1993 | Pohndorf |
| 4,699,298 A | 10/1987 | Grant et al. | 5,297,826 A | 3/1994 | Percebois et al. |
| 4,700,926 A | 10/1987 | Hansen | 5,316,041 A | 5/1994 | Ramacier, Jr. et al. |
| 4,703,957 A | 11/1987 | Blenkush | 5,318,332 A | 6/1994 | Hohmann et al. |
| 4,706,847 A | 11/1987 | Sankey et al. | 5,330,235 A | 7/1994 | Wagner et al. |
| 4,712,280 A | 12/1987 | Fildan | 5,348,051 A | 9/1994 | Kallenbach |
| 4,733,890 A | 3/1988 | Vyse | 5,348,354 A | 9/1994 | Badoureaux |
| 4,738,401 A | 4/1988 | Filicicchia | 5,353,836 A | 10/1994 | deCler et al. |
| 4,753,268 A | 6/1988 | Palau | 5,356,183 A | 10/1994 | Cole |
| 4,768,558 A | 9/1988 | Weber | 5,374,088 A | 12/1994 | Moretti et al. |
| 4,776,067 A | 10/1988 | Sorensen | 5,385,311 A | 1/1995 | Morikawa et al. |
| 4,790,567 A | 12/1988 | Kawano et al. | 5,385,331 A | 1/1995 | Allread et al. |
| 4,790,569 A | 12/1988 | Chaffee | D357,307 S | 4/1995 | Ramacier, Jr. et al. |
| 4,792,115 A | 12/1988 | Jindra et al. | 5,405,333 A | 4/1995 | Richmond |
| 4,793,637 A | 12/1988 | Laipply et al. | 5,405,339 A | 4/1995 | Kohnen et al. |
| D300,361 S | 3/1989 | Tokarz | 5,405,340 A | 4/1995 | Fageol et al. |
| 4,824,148 A | 4/1989 | Grabowski | 5,411,300 A | 5/1995 | Mitsui |
| 4,827,921 A | 5/1989 | Rugheimer | 5,417,442 A | 5/1995 | Jornhagen |
| 4,832,237 A | 5/1989 | Hurford, Jr. | 5,421,622 A | 6/1995 | Godeau |
| 4,834,423 A | 5/1989 | DeLand | 5,437,650 A | 8/1995 | Larkin et al. |
| 4,844,512 A | 7/1989 | Gahwiler | 5,462,313 A | 10/1995 | Rea et al. |
| 4,863,201 A | 9/1989 | Carstens | 5,494,074 A | 2/1996 | Ramacier, Jr. et al. |
| 4,863,202 A | 9/1989 | Oldford | D369,409 S | 4/1996 | Salter |
| 4,896,402 A | 1/1990 | Jansen et al. | 5,507,733 A | 4/1996 | Larkin et al. |
| 4,900,065 A | 2/1990 | Houck | 5,511,527 A | 4/1996 | Lorraine et al. |
| 4,903,995 A | 2/1990 | Blenkush et al. | D372,093 S | 7/1996 | Sampson et al. |
| 4,923,228 A | 5/1990 | Laipply et al. | 5,536,258 A | 7/1996 | Folden |
| 4,928,859 A | 5/1990 | Krahn et al. | 5,542,712 A | 8/1996 | Klinger et al. |
| 4,928,999 A | 5/1990 | Landriault et al. | 5,547,166 A | 8/1996 | Engdahl |
| 4,934,655 A | 6/1990 | Blenkush et al. | 5,547,230 A | 8/1996 | Bank et al. |
| 4,935,992 A | 6/1990 | Due | 5,553,895 A | 9/1996 | Karl et al. |
| 4,946,200 A | 8/1990 | Blenkush et al. | D375,160 S | 10/1996 | Sampson et al. |
| 4,946,204 A | 8/1990 | Boticki | 5,568,946 A | 10/1996 | Jackowski |
| 4,949,745 A | 8/1990 | McKeon | 5,595,217 A | 1/1997 | Gillen et al. |
| 4,966,398 A | 10/1990 | Peterson | 5,601,317 A | 2/1997 | Crouse et al. |
| 4,969,879 A | 11/1990 | Lichte | 5,607,190 A | 3/1997 | Exandier et al. |
| D313,067 S | 12/1990 | Kotake et al. | 5,617,609 A | 4/1997 | Bently |
| D313,277 S | 12/1990 | Haining | 5,620,025 A | 4/1997 | Lewin |
| D314,050 S | 1/1991 | Sone | 5,628,726 A | 5/1997 | Cotter |
| D314,233 S | 1/1991 | Medvick | D380,262 S | 6/1997 | Van Funderburk et al. |
| 4,982,736 A | 1/1991 | Schneider | 5,639,064 A | 6/1997 | deCler et al. |
| 4,991,880 A | 2/1991 | Bernart | D382,639 S | 8/1997 | Musgrave et al. |
| 5,009,252 A | 4/1991 | Faughn | D384,731 S | 10/1997 | Ramacier, Jr. et al. |
| 5,015,014 A | 5/1991 | Sweeney | 5,681,062 A | 10/1997 | Fukao et al. |
| 5,029,908 A | 7/1991 | Belisaire | 5,682,662 A | 11/1997 | Coules et al. |
| 5,033,777 A | 7/1991 | Blenkush | 5,683,117 A | 11/1997 | Corbett et al. |
| D319,312 S | 8/1991 | Schneider | D387,147 S | 12/1997 | Vandermast et al. |
| 5,052,725 A | 10/1991 | Meyer et al. | 5,695,223 A | 12/1997 | Boticki |
| 5,074,601 A | 12/1991 | Spors et al. | D388,876 S | 1/1998 | Sampson |
| 5,076,615 A | 12/1991 | Sampson | 5,709,244 A | 1/1998 | Patriquin et al. |
| 5,078,429 A | 1/1992 | Braut et al. | 5,725,258 A | 3/1998 | Kujawski |
| 5,085,472 A | 2/1992 | Guest | 5,737,810 A | 4/1998 | Krauss |
| 5,090,448 A | 2/1992 | Truchet | 5,745,957 A | 5/1998 | Khokhar et al. |

| | | | | | | |
|---|---|---|---|---|---|---|
| 5,746,414 | A | 5/1998 | Weldon et al. | 6,454,314 B1 | 9/2002 | Grosspietsch et al. |
| 5,762,646 | A | 6/1998 | Cotter | 6,481,758 B1 | 11/2002 | Andre et al. |
| 5,784,750 | A | 7/1998 | Sankovic et al. | 6,481,759 B1 | 11/2002 | Kawasaki et al. |
| 5,799,987 | A | 9/1998 | Sampson | 6,485,064 B1 | 11/2002 | Davidson |
| 5,820,614 | A | 10/1998 | Erskine et al. | 6,485,483 B1 | 11/2002 | Fujii |
| 5,837,180 | A | 11/1998 | Linder et al. | 6,497,433 B1 * | 12/2002 | Ketcham ................ 285/319 |
| 5,845,943 | A | 12/1998 | Ramacier, Jr. et al. | 6,505,866 B1 | 1/2003 | Nakamura et al. |
| 5,855,568 | A | 1/1999 | Battiato et al. | 6,508,807 B1 | 1/2003 | Peters |
| 5,879,033 | A | 3/1999 | Hansel et al. | 6,520,546 B2 | 2/2003 | Szabo |
| 5,882,047 | A | 3/1999 | Ostrander et al. | D471,261 S | 3/2003 | Kozu |
| 5,884,531 | A | 3/1999 | Koenig | 6,540,263 B1 | 4/2003 | Sausner |
| D407,803 | S | 4/1999 | Redman | 6,543,745 B1 | 4/2003 | Enerson |
| 5,897,142 | A | 4/1999 | Kulevsky | 6,595,964 B2 | 7/2003 | Finley et al. |
| 5,911,367 | A | 6/1999 | McInerney | 6,609,696 B2 | 8/2003 | Enerson |
| 5,911,403 | A | 6/1999 | deCler et al. | 6,612,634 B1 | 9/2003 | Zoppas |
| 5,911,404 | A | 6/1999 | Cheng | 6,626,419 B2 | 9/2003 | DeCler et al. |
| 5,930,424 | A | 7/1999 | Heimberger et al. | 6,626,465 B2 | 9/2003 | Lacroix et al. |
| 5,937,501 | A | 8/1999 | Imgram | D481,125 S | 10/2003 | Hayamizu |
| 5,938,244 | A | 8/1999 | Meyer | 6,641,177 B1 | 11/2003 | Pinciaro |
| 5,941,577 | A | 8/1999 | Musellec | 6,649,829 B2 | 11/2003 | Garber et al. |
| 5,942,730 | A | 8/1999 | Schwarz et al. | 6,652,007 B1 | 11/2003 | Hwang |
| D413,967 | S | 9/1999 | Yuen | D484,241 S | 12/2003 | Peters et al. |
| 5,957,898 | A | 9/1999 | Jepson et al. | 6,669,681 B2 | 12/2003 | Jepson et al. |
| 5,961,157 | A | 10/1999 | Baron et al. | 6,676,172 B2 | 1/2004 | Alksnis |
| 5,964,485 | A | 10/1999 | Hame et al. | D486,909 S | 2/2004 | Cise et al. |
| 5,965,077 | A | 10/1999 | Rowley et al. | 6,688,654 B2 | 2/2004 | Romero |
| 5,975,489 | A | 11/1999 | deCler et al. | 6,692,038 B2 | 2/2004 | Braun |
| 5,984,378 | A | 11/1999 | Ostrander et al. | 6,695,817 B1 | 2/2004 | Fangrow |
| 5,988,704 | A | 11/1999 | Ryhman | 6,705,591 B2 | 3/2004 | deCler |
| 6,012,743 | A | 1/2000 | Godeau et al. | 6,722,705 B2 | 4/2004 | Korkor |
| 6,015,171 | A | 1/2000 | Schorn | 6,722,708 B2 | 4/2004 | Morohoshi et al. |
| D419,861 | S | 2/2000 | Khokhar | 6,762,365 B2 | 7/2004 | Inoue et al. |
| 6,019,348 | A | 2/2000 | Powell | 6,767,017 B2 | 7/2004 | Crapart et al. |
| 6,024,124 | A | 2/2000 | Braun et al. | D495,050 S | 8/2004 | Guala |
| 6,029,701 | A | 2/2000 | Chaffardon et al. | 6,783,520 B1 | 8/2004 | Candray et al. |
| 6,032,691 | A | 3/2000 | Powell et al. | D497,428 S | 10/2004 | Hayamizu |
| 6,041,805 | A | 3/2000 | Gydesen et al. | 6,799,747 B1 | 10/2004 | Lai |
| D422,487 | S | 4/2000 | Khokhar | D498,533 S | 11/2004 | Hayamizu |
| 6,050,297 | A | 4/2000 | Ostrowski et al. | 6,814,726 B1 | 11/2004 | Lauer |
| 6,076,234 | A | 6/2000 | Khokhar et al. | 6,840,277 B1 | 1/2005 | Nimberger |
| 6,077,245 | A | 6/2000 | Heinrich et al. | 6,846,021 B2 | 1/2005 | Rohde et al. |
| 6,077,259 | A | 6/2000 | Caizza et al. | 6,848,602 B2 | 2/2005 | deCler et al. |
| 6,082,401 | A | 7/2000 | Braun et al. | 6,848,723 B2 | 2/2005 | Lamich |
| 6,086,044 | A | 7/2000 | Guest | 6,863,314 B2 | 3/2005 | Guest |
| 6,089,540 | A | 7/2000 | Heinrichs et al. | 6,871,669 B2 | 3/2005 | Meyer et al. |
| 6,099,045 | A | 8/2000 | Pirona | 6,871,878 B2 | 3/2005 | Miros |
| 6,112,855 | A | 9/2000 | Camacho et al. | D503,778 S | 4/2005 | Wicks |
| 6,123,690 | A | 9/2000 | Mejslov | 6,886,803 B2 | 5/2005 | Mikiya et al. |
| 6,135,150 | A | 10/2000 | Powell et al. | 6,897,374 B2 | 5/2005 | Garber et al. |
| 6,135,992 | A | 10/2000 | Wang | 6,899,315 B2 | 5/2005 | Maiville et al. |
| 6,142,538 | A | 11/2000 | Volgstadt et al. | 6,902,144 B2 | 6/2005 | deCler |
| 6,145,896 | A | 11/2000 | Vitel et al. | D507,647 S | 7/2005 | Beck et al. |
| 6,152,914 | A | 11/2000 | Van De Kerkhof et al. | 6,916,007 B2 | 7/2005 | deCler et al. |
| 6,155,610 | A | 12/2000 | Godeau et al. | 6,916,050 B2 | 7/2005 | Milhas |
| 6,161,578 | A | 12/2000 | Braun et al. | 6,926,311 B2 | 8/2005 | Chang et al. |
| 6,176,523 | B1 | 1/2001 | Winslett | 6,929,246 B2 | 8/2005 | Arzenton et al. |
| 6,182,694 | B1 | 2/2001 | Sievers et al. | 6,945,273 B2 | 9/2005 | Reid |
| 6,189,560 | B1 | 2/2001 | Reynolds | 6,949,084 B2 | 9/2005 | Marggi et al. |
| 6,199,915 | B1 | 3/2001 | Becker | 6,962,275 B2 | 11/2005 | deCler et al. |
| 6,199,919 | B1 | 3/2001 | Kawasaki et al. | 6,978,800 B2 | 12/2005 | deCler et al. |
| 6,199,920 | B1 | 3/2001 | Neustadtl | 6,981,547 B2 | 1/2006 | Maguire et al. |
| 6,221,064 | B1 | 4/2001 | Nadal | 6,997,486 B2 | 2/2006 | Milhas |
| 6,231,089 | B1 | 5/2001 | DeCler et al. | 6,997,919 B2 | 2/2006 | Olsen et al. |
| D444,054 | S | 6/2001 | Bernard et al. | 7,005,581 B2 | 2/2006 | Burnette |
| 6,250,688 | B1 | 6/2001 | Kirby | 7,011,342 B2 | 3/2006 | Guivarc'h et al. |
| 6,257,626 | B1 | 7/2001 | Campau | 7,014,214 B2 | 3/2006 | Kaneko |
| 6,260,851 | B1 | 7/2001 | Baron | D522,109 S | 5/2006 | White et al. |
| 6,261,282 | B1 | 7/2001 | Jepson et al. | 7,040,670 B2 | 5/2006 | Madden |
| 6,293,596 | B1 | 9/2001 | Kinder | 7,044,161 B2 | 5/2006 | Tiberghien |
| 6,296,796 | B1 | 10/2001 | Gordon | 7,044,506 B2 | 5/2006 | Dong |
| 6,302,147 | B1 | 10/2001 | Rose et al. | D523,553 S | 6/2006 | Beck et al. |
| 6,318,764 | B1 | 11/2001 | Trede et al. | 7,080,665 B2 | 7/2006 | Whall |
| 6,344,033 | B1 | 2/2002 | Jepson et al. | 7,081,223 B2 | 7/2006 | Khoury |
| 6,382,593 | B1 | 5/2002 | deCler et al. | 7,108,297 B2 | 9/2006 | Takayanagi et al. |
| D459,206 | S | 6/2002 | Caveney et al. | 7,118,138 B1 | 10/2006 | Rowley et al. |
| 6,402,207 | B1 | 6/2002 | Segal et al. | 7,128,348 B2 | 10/2006 | Kawamura et al. |
| 6,422,574 | B1 | 7/2002 | Mooklar | 7,137,654 B2 | 11/2006 | Segal et al. |
| 6,423,053 | B1 | 7/2002 | Lee | 7,140,592 B2 | 11/2006 | Phillips |
| 6,439,620 | B1 | 8/2002 | Guest | 7,147,252 B2 | 12/2006 | Teuscher et al. |

| | | |
|---|---|---|
| 7,150,478 B2 | 12/2006 | Poirier et al. |
| 7,153,296 B2 | 12/2006 | Mitchell |
| 7,163,022 B2 | 1/2007 | Whall |
| D540,944 S | 4/2007 | Guala |
| 7,210,917 B2 | 5/2007 | Lai et al. |
| D547,446 S | 7/2007 | Racz et al. |
| D550,355 S | 9/2007 | Racz et al. |
| D557,409 S | 12/2007 | Veliss et al. |
| 7,316,428 B2 | 1/2008 | Takayanagi et al. |
| D564,660 S | 3/2008 | Hayashi |
| 7,343,931 B2 | 3/2008 | Packham |
| D567,340 S | 4/2008 | Tiberghien |
| 7,352,771 B2 | 4/2008 | Garber |
| D569,507 S | 5/2008 | Blanchard |
| D569,955 S | 5/2008 | Chen |
| 7,377,553 B2 | 5/2008 | Takayanagi |
| D570,457 S | 6/2008 | Brown |
| 7,390,029 B2 | 6/2008 | Matsubara |
| 7,394,375 B2 | 7/2008 | Johnson |
| 7,434,842 B2 | 10/2008 | Schmidt |
| 7,434,846 B2 | 10/2008 | Baumgartner |
| 7,448,653 B2 | 11/2008 | Jensen et al. |
| 7,464,970 B2 | 12/2008 | Yamada et al. |
| 7,467,813 B2 | 12/2008 | Gunderson |
| 7,469,472 B2 | 12/2008 | DeCler et al. |
| 7,478,840 B2 | 1/2009 | Youssefifar |
| 7,488,446 B2 | 2/2009 | Meyer et al. |
| 7,494,156 B2 | 2/2009 | Okada |
| 7,503,595 B2 | 3/2009 | McKay |
| 7,516,990 B2 | 4/2009 | Jamison et al. |
| 7,546,857 B2 | 6/2009 | Chadbourne et al. |
| 7,547,047 B2 | 6/2009 | deCler et al. |
| D595,845 S | 7/2009 | Miros et al. |
| D595,846 S | 7/2009 | Racz et al. |
| D596,288 S | 7/2009 | Racz et al. |
| D596,739 S | 7/2009 | Ng et al. |
| 7,562,906 B2 | 7/2009 | Schmidt |
| 7,566,077 B2 | 7/2009 | Tsurumi |
| 7,581,763 B2 | 9/2009 | Salomon-Bahls |
| D602,128 S | 10/2009 | Williams et al. |
| 7,614,666 B2 | 11/2009 | Eggert et al. |
| 7,631,660 B2 | 12/2009 | deCler et al. |
| 7,647,954 B2 | 1/2010 | Garber et al. |
| 7,666,178 B2 | 2/2010 | McMichael |
| D612,019 S | 3/2010 | Williams et al. |
| D612,021 S | 3/2010 | Schmidt |
| 7,677,608 B2 | 3/2010 | Takayanagi |
| D613,853 S | 4/2010 | Ng et al. |
| 7,695,020 B2 | 4/2010 | Schmidt |
| 7,708,025 B2 | 5/2010 | Johnson |
| 7,731,244 B2 | 6/2010 | Miros et al. |
| D619,706 S | 7/2010 | Schon et al. |
| 7,770,939 B2 | 8/2010 | Jensen et al. |
| 7,806,139 B2 | 10/2010 | Packham et al. |
| 7,841,357 B2 | 11/2010 | Rankin |
| D629,894 S | 12/2010 | Lombardi, III et al. |
| 7,849,877 B2 | 12/2010 | Tan et al. |
| D630,320 S | 1/2011 | Lombardi, III et al. |
| D632,783 S | 2/2011 | Maesarapu |
| 7,878,553 B2 | 2/2011 | Wicks et al. |
| D634,840 S | 3/2011 | Lombardi, III et al. |
| D639,398 S | 6/2011 | Wilhelm |
| 7,954,374 B2 | 6/2011 | Rankin |
| 7,954,515 B2 | 6/2011 | Gerst |
| D642,244 S | 7/2011 | Wilhelm |
| 7,976,071 B2 | 7/2011 | Bibby |
| D645,547 S | 9/2011 | Lombardi, III et al. |
| 2001/0017466 A1 | 8/2001 | Braun |
| 2002/0022762 A1 | 2/2002 | Beane et al. |
| 2002/0093192 A1 | 7/2002 | Matkovich |
| 2002/0140172 A1 | 10/2002 | Platusich |
| 2002/0156344 A1 | 10/2002 | Pasricha et al. |
| 2002/0185861 A1 | 12/2002 | Inoue |
| 2003/0004397 A1 | 1/2003 | Kameya et al. |
| 2003/0067162 A1 | 4/2003 | Welsh et al. |
| 2003/0193188 A1 | 10/2003 | Miros |
| 2003/0230894 A1 | 12/2003 | Cleveland et al. |
| 2004/0021318 A1 | 2/2004 | Fritze et al. |
| 2004/0056484 A1 | 3/2004 | Kwon et al. |
| 2004/0094903 A1 | 5/2004 | Sutherland |
| 2004/0195830 A1 | 10/2004 | Gilmour |
| 2004/0199143 A1 | 10/2004 | Lauer |
| 2004/0227346 A1 | 11/2004 | Jamison et al. |
| 2004/0232696 A1 | 11/2004 | Andre |
| 2005/0033237 A1 | 2/2005 | Fentress et al. |
| 2005/0046184 A1 | 3/2005 | Chang |
| 2005/0057042 A1 | 3/2005 | Wicks |
| 2005/0082828 A1 | 4/2005 | Wicks et al. |
| 2005/0087981 A1 | 4/2005 | Yamada et al. |
| 2005/0209583 A1 | 9/2005 | Powers et al. |
| 2005/0217265 A1 | 10/2005 | Popp et al. |
| 2005/0242579 A1 | 11/2005 | Bright et al. |
| 2005/0275220 A1 | 12/2005 | Shu |
| 2006/0066100 A1 | 3/2006 | Nakashima et al. |
| 2006/0152003 A1 | 7/2006 | Slunick et al. |
| 2006/0264814 A1 | 11/2006 | Sage |
| 2006/0293629 A1 | 12/2006 | Cote, Sr. et al. |
| 2007/0025811 A1 | 2/2007 | Wilhelm |
| 2007/0029795 A1 | 2/2007 | Moner et al. |
| 2007/0029796 A1 | 2/2007 | Bibby |
| 2007/0106213 A1 | 5/2007 | Spera et al. |
| 2007/0137718 A1 | 6/2007 | Rushlander et al. |
| 2007/0169825 A1 | 7/2007 | Packham et al. |
| 2007/0209716 A1 | 9/2007 | Rankin |
| 2007/0284875 A1 | 12/2007 | Salomon-Bahls et al. |
| 2008/0007051 A1 | 1/2008 | Jensen et al. |
| 2008/0011703 A1 | 1/2008 | Schmeisser et al. |
| 2008/0012314 A1 | 1/2008 | Harger et al. |
| 2008/0018105 A1 | 1/2008 | Le Bars |
| 2008/0048448 A1 | 2/2008 | Jamison et al. |
| 2008/0078464 A1 | 4/2008 | Loewe |
| 2008/0111371 A1 | 5/2008 | Feger et al. |
| 2008/0111372 A1 | 5/2008 | Trede et al. |
| 2008/0129047 A1 | 6/2008 | Blivet et al. |
| 2008/0164694 A1 | 7/2008 | Zdroik et al. |
| 2008/0191466 A1 | 8/2008 | Knipple et al. |
| 2008/0200901 A1 | 8/2008 | Rasmussen et al. |
| 2008/0277923 A1 | 11/2008 | Brandt et al. |
| 2008/0277924 A1 | 11/2008 | Jensen et al. |
| 2008/0284167 A1 | 11/2008 | Lim et al. |
| 2008/0287920 A1 | 11/2008 | Fangrow et al. |
| 2009/0079187 A1 | 3/2009 | Malone |
| 2009/0127847 A1 | 5/2009 | Hagen et al. |
| 2009/0129047 A1 | 5/2009 | Park et al. |
| 2009/0140519 A1 | 6/2009 | Pavnaskar et al. |
| 2009/0167018 A1 | 7/2009 | Lien |
| 2009/0187166 A1 | 7/2009 | Young |
| 2009/0188575 A1 | 7/2009 | Williams et al. |
| 2009/0256355 A1 | 10/2009 | Wicks et al. |
| 2010/0001516 A1 | 1/2010 | Pisula, Jr. et al. |
| 2010/0056975 A1 | 3/2010 | Dale et al. |
| 2010/0078934 A1 | 4/2010 | Matsunaga |
| 2010/0185040 A1 | 7/2010 | Uber et al. |
| 2010/0194100 A1 | 8/2010 | Koch |
| 2010/0276922 A1 | 11/2010 | Rehder et al. |
| 2010/0295295 A1 | 11/2010 | Schmidt |
| 2010/0301599 A1 | 12/2010 | Jensen et al. |
| 2010/0319796 A1 | 12/2010 | Whitaker |
| 2011/0012340 A1 | 1/2011 | Packham et al. |
| 2011/0127767 A1 | 6/2011 | Wicks et al. |
| 2011/0204621 A1 | 8/2011 | Whitaker et al. |
| 2011/0204622 A1 | 8/2011 | Lewis et al. |

FOREIGN PATENT DOCUMENTS

| | | |
|---|---|---|
| DE | 3439522 | 8/1985 |
| DE | 3533000 | 3/1987 |
| DE | 4122455 | 1/1993 |
| DE | 19800050 | 7/1998 |
| DE | 102005015343 | 10/2006 |
| EP | 0360634 | 3/1990 |
| EP | 0390746 | 10/1990 |
| EP | 0267067 | 7/1991 |
| EP | 0482277 | 4/1992 |
| EP | 0592823 | 4/1994 |
| EP | 0715111 | 6/1996 |

| | | |
|---|---|---|
| EP | 0865779 | 9/1998 |
| EP | 0877891 | 11/1998 |
| EP | 0890054 | 1/1999 |
| EP | 0982525 | 3/2000 |
| EP | 1497582 | 1/2005 |
| EP | 1564469 | 8/2005 |
| EP | 1843074 | 10/2007 |
| FR | 2031965 | 11/1970 |
| FR | 2429370 | 1/1980 |
| FR | 280871 | 10/2001 |
| FR | 2853043 | 10/2004 |
| FR | 2870921 | 12/2005 |
| FR | 2903164 | 1/2008 |
| GB | 583459 | 12/1946 |
| GB | 890775 | 3/1962 |
| GB | 2177769 | 1/1987 |
| GB | 2218166 | 11/1989 |
| GB | 2271157 | 4/1994 |
| GB | 2379253 | 3/2003 |
| JP | 53-006918 | 1/1978 |
| JP | 5-223189 | 8/1993 |
| JP | 7-145889 | 6/1995 |
| JP | 10-169869 | 6/1998 |
| JP | 11-82849 | 3/1999 |
| JP | 2003-42363 | 2/2003 |
| JP | 2003-42368 | 2/2003 |
| WO | WO 93/17270 | 9/1993 |
| WO | WO 95/08732 | 3/1995 |
| WO | WO 00/79172 | 12/2000 |
| WO | WO 2004/104466 | 12/2004 |
| WO | WO 2005/064216 | 7/2005 |
| WO | WO 2006/031958 | 3/2006 |
| WO | WO 2006/073778 | 7/2006 |
| WO | WO 2006/084171 | 8/2006 |
| WO | WO 2006/135666 | 12/2006 |
| WO | WO 2007/038222 | 4/2007 |
| WO | WO 2007/116387 | 10/2007 |
| WO | WO 2007/120620 | 10/2007 |
| WO | WO 2008/023021 | 2/2008 |
| WO | WO 2009/026441 | 2/2009 |

OTHER PUBLICATIONS

Barbed Tee Adapter, 1/2 in to 2/8 in to 1/2 in [Item # F1728], http://www.horticulturesource.com/product_info.php/products_id/4016/language/en; dated accessed Sep. 14, 2009, 3 pages.

Brochure, "Precision Components", Value Plastics, Inc., 2002, 132 pages.

Capabilities [online], Jay Manufacturing Corp., retrieved on Apr. 9, 2010, retrieved from the Internet: <URL: http://www.jaymfg.com/capabilities.htm>, 2 pages.

Flojet "Quick Connect" Port System Adapter 90 Elbow Type Quad Port X 1/2" Hose Barb, http://www.amazon.com/Quick-Connect-Port-System-Quad-Barb-90/dp/B0000AZ771/ref=sr_1_16?s=sporting-goods&ie=UTF8&qid=1300220596&sr=1-16, date accessed Sep. 14, 2009; 3 pages.

High-Flow Quick Disconnect Couplings; http://www.coleparmercom/catalog/product_view.asp?sku=3130355; date accessed Sep. 14, 2009, 3 pages.

Mills, The Process of Vacuum-forming Plastic Parts, IPFrontline.com [online], retrieved on Apr. 9, 2010, retrieved from the Internet: <URL: http://www.ipfrontline.com/depts/article.asp?id=453&deptid=2>, 3 pages.

Nylon, Polypropylene Kynar (PVDF) Plastic Fittings for Flexible Tubing & Hose, http://www.omega.com/pdf/tubing/fittings_tubing_hose/nylon_poly_kynar/nylon.asp; dated accessed Sep. 14, 2009, 2 pages.

Science of Hose Barbs, Colder Products Company, http://www.pddnet.com/article-the-science-of-hose-barbs/, date accessed Sep. 4, 2009, 6 pages.

Stackable Hose Barb Elbow—1/2" CTS x 1/2 ID Barb, http://www.freshwatersystems.com/p-1714-stackable-hose-barb-elbow-12-cts-x-12-id-barb.aspx?affiliatied=10052&utm_source=shopzilla&utm_medium=Feed&utm_campaign=Product&utm_term=3512-1008, date accessed Sep. 14, 2009, 1 page.

Stainless Steel Overview: History [online], Stainless Steel Industry of North America, retrieved on Apr. 9, 2010, retrieved from the Internet: <URL: http://www.ssina.com/overview/history.html>, 1 page.

* cited by examiner

FLUID CONDUIT COUPLERS WITH DEPRESSIBLE LATCH MECHANISM

CROSS REFERENCE TO RELATED APPLICATIONS

This application is a continuation of U.S. patent application Ser. No. 11/336,587 filed 20 Jan. 2006, now U.S. Pat. No. 7,806,139, entitled "Fluid conduit coupling assembly having male and female couplers with integral valves," which is hereby incorporated herein by reference in its entirety.

TECHNICAL FIELD

The technology disclosed herein is related to latch mechanisms that connect male and female couplers that connect the ends of two fluid lines together.

BACKGROUND

Quick connect/disconnect coupling assemblies for small flexible tube applications are known in the art. Such coupling assemblies are utilized for bio-medical applications, convenience handling, beverage dispensing, pneumatic instrument connections, photochemical handling, and many others. Despite the existence of such coupling assemblies, there is a need in the art for a coupling assembly that offers higher flow rates, improved coupling security, simplified operation, positive fluid shut-off when detached, and decreased manufacturing costs.

The information included in this Background section of the specification, including any references cited herein and any description or discussion thereof, is included for technical reference purposes only and is not to be regarded subject matter by which the scope of the invention is to be bound.

SUMMARY

The invention disclosed herein is directed to fluid conduit coupling assembly has a depressible latch mechanism that secures a first fluid conduit to a second fluid conduit via a first coupler and a second coupler. The first coupler connects to the first fluid conduit and the second coupler connects to the second fluid conduit. The depressible latch mechanism may be formed by a pair of cantilevered buttons, which may be disposed in symmetrically opposed positions on one of the couplers. The cantilevered buttons may have engagement lips that extend distally and may have catches that extend radially outward to engage an engagement feature formed on an interior wall of the opposing coupler. Fluid ports within the couplers interface when the couplers connect to provide fluid flow between the first and second conduits. Valves may be disposed in each of the couplers to arrest fluid flow when the couplers are detached and automatically open to allow fluid to flow when the couplers are connected.

In one implementation, a fluid conduit coupling assembly may be composed of a first coupler and a second coupler that connect fluid conduits together. The first coupler may have a first attachment end that defines a first fluid lumen and that is configured for attaching to a first fluid conduit. The second coupler may similarly have a second attachment end that defines a second fluid lumen and that is configured for attaching to a second fluid conduit. The first coupler has a first housing that defines a pair of cantilevered buttons. Each of the cantilevered buttons may be attached at a proximal end to the first housing. The cantilevered buttons may be separated from the first housing by slots on lateral sides of each cantilevered button. The cantilevered buttons may further extend to a distal end congruent with a seam face of the first housing. The cantilevered buttons may each further have an engagement lip that extends distally from the distal end and that has a catch directed radially outward with respect to the first couple. The first coupler may also have a first barrel substantially encompassed by the first housing and that defines a first fluid path in fluid communication with the first fluid lumen in the first attachment end. The second coupler may have a second housing that defines a ridge on an interior wall of the second housing for interfacing with the catch on the engagement lip on each of the cantilevered buttons. The second coupler may further have a second barrel substantially encompassed by the second housing and that defines a second fluid path in fluid communication with the second fluid lumen in the second attachment end. When the first and second couplers are mated together, the pair of engagement lips operably connect with the ridge on the second housing and the first fluid path of the first barrel is fluidly coupled with the second fluid path in the second barrel.

In another implementation, a fluid conduit coupling assembly may be composed of a male coupler and a female coupler that connect fluid conduits together. The male coupler may have a first barbed fitting configured for attachment with a first fluid conduit and the female coupler may have a second barbed fitting for attachment with a second fluid conduit. The male coupler may have a male housing attached to the first barbed fitting. Similarly, the female coupler may have a female housing attached to the second barbed fitting. An elongated male fluid port may extend from within the male housing past a mating end of the male housing and be in fluid communication with the first barbed fitting. Similarly, an elongated female fluid port may extend from within the female housing and be in fluid communication with the second barbed fitting. The male housing may further define a pair of depressible latch mechanisms disposed at the mating end of the male coupler. The female housing may define an engagement feature on an interior wall adjacent a mating end of the female housing. When the male coupler is connected to the female coupler, the depressible latch mechanism enters the female housing and operably connects with the engagement feature on the interior wall thereof to hold the male and female couplers together. Further, the elongated male fluid port is received within the elongated female fluid port to create a fluid pathway from the first barbed fitting, through the elongated male and female ports, and through the second barbed fitting.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention is provided in the following written description of various embodiments of the invention, illustrated in the accompanying drawings, and defined in the appended claims.

DETAILED DESCRIPTION a. Overview of Coupling Assemblies

A quick disconnect coupling assembly for connecting the ends of two fluid conduits such as the small flexible tubing utilized in bio-medical applications, convenience handling, beverage dispensing, instrument connections, photochemical handling, and others. Such a quick disconnect coupling assembly is particularly useful in connecting two fluid conduits in a bio-medical environment. The coupling assembly of the present invention is ergonomically designed, easily and securely connected, and yet easily intentionally disconnected. The coupling assembly of the subject invention has a male coupler with an integral valve and a female coupler with an integral valve. Each valve is biased closed via a biasing mechanism, but opens automatically by simply connecting the male and female couplers together. Upon the male and female couplers being disconnected from each other, each valve closes automatically via its integral biasing mechanism.

In a first embodiment of a coupling assembly according to the present invention, the male and female couplers each have a structural member. When the male and female couplers are being connected, their respective structural members enter the other coupler to cause the valve of the other coupler to open. When the male and female couplers are disengaged from each other, their respective structural members exit the other coupler and the valve of the other coupler is allowed to bias closed.

In a second embodiment of a coupling assembly according to the present invention, the male and female couplers each have a body that is displaceable within its respective coupler. When the male and female couplers are being connected, their respective bodies contact each other. This contact causes each body to displace within its respective coupler, which causes the valve of the respective coupler to open. When the male and female couplers are disengaged from each other, their respective bodies cease contacting each other and the valves are allowed to bias closed.

b. First Embodiment of the Quick Disconnect Coupling Assembly

Figure 1:
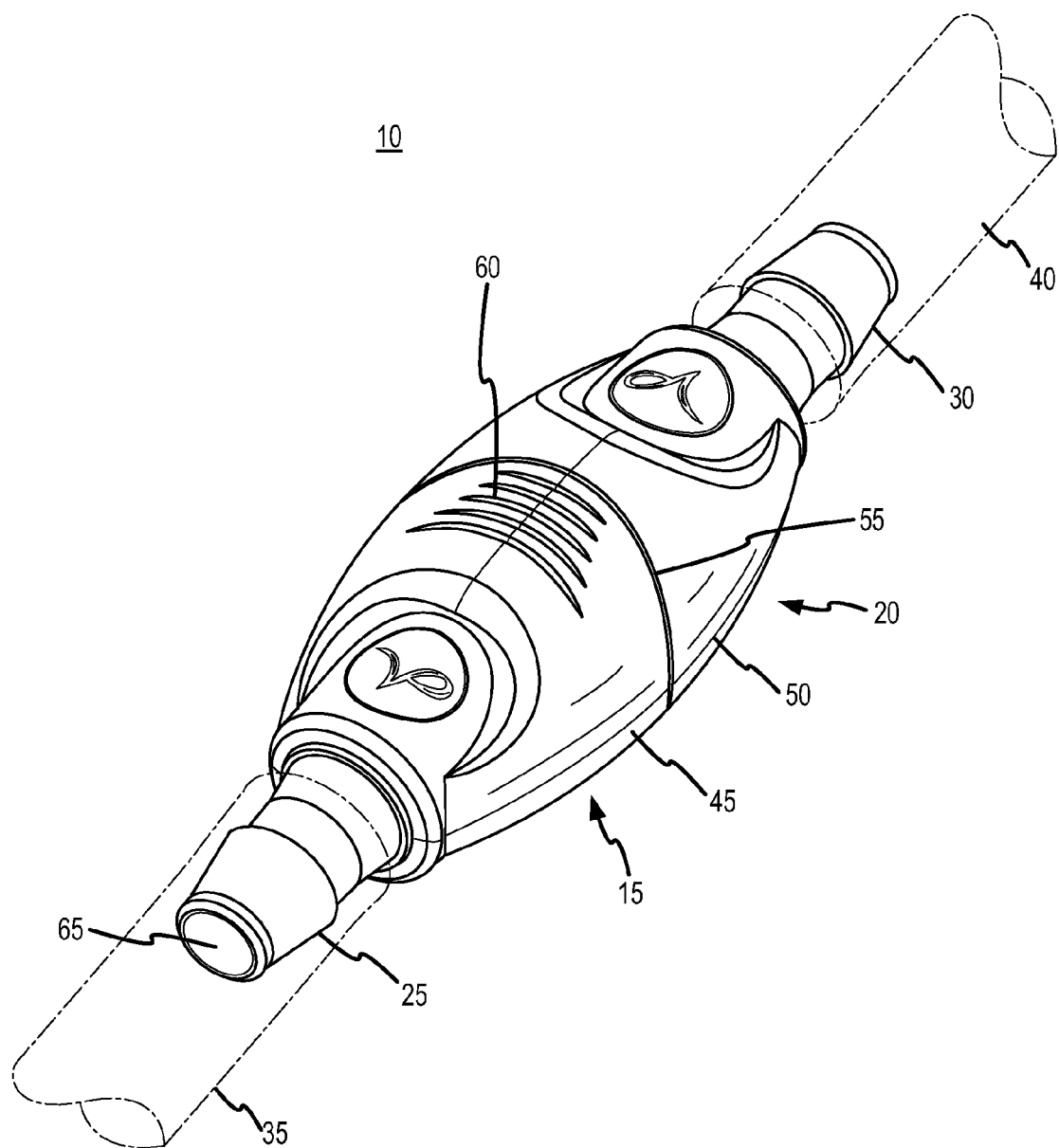
FIG. 1 is an isometric view of the quick disconnect coupling assembly, wherein the male coupler and female coupler are connected.
Figure 2:
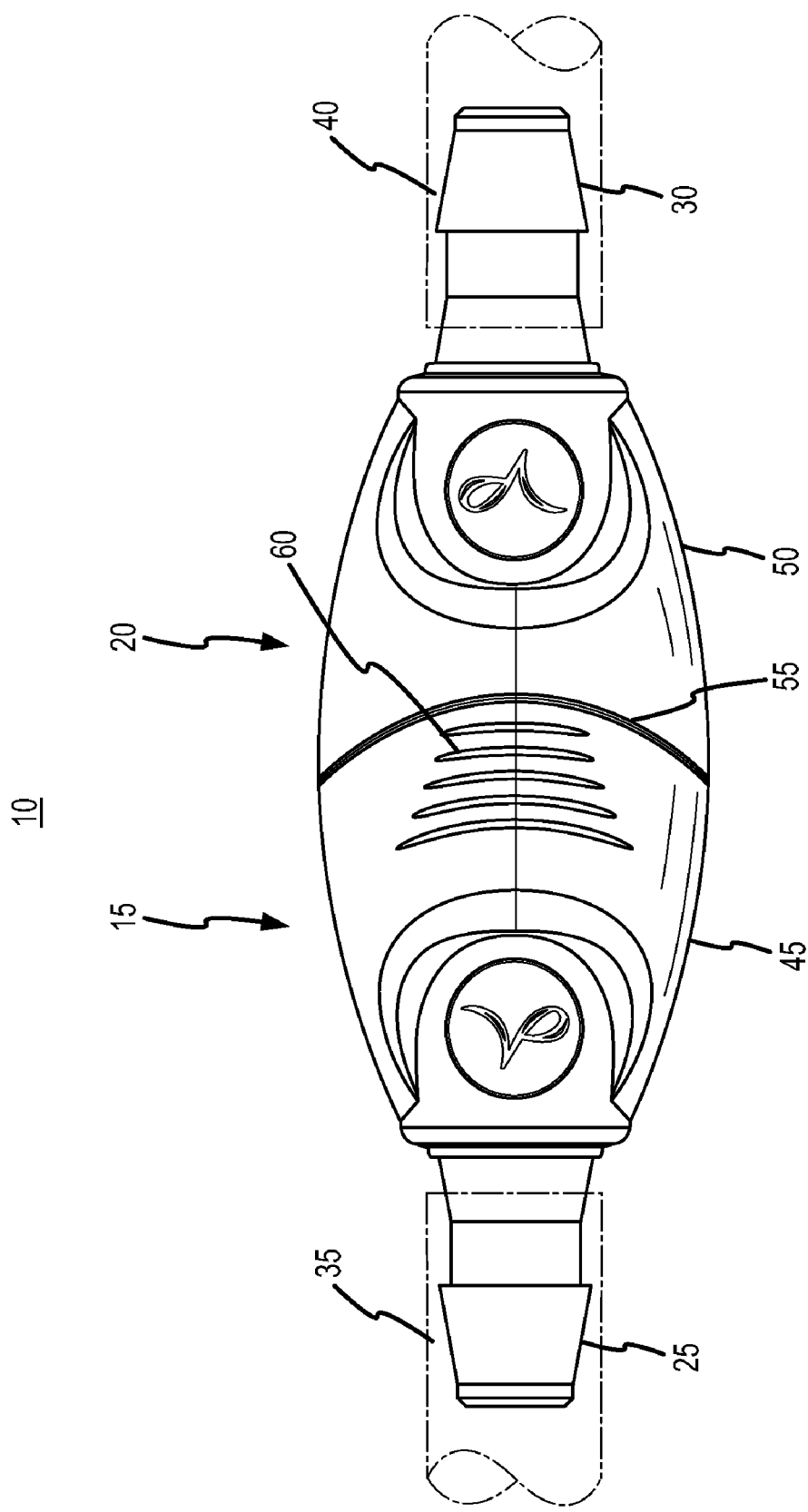
FIG. 2 is a top plan of the coupling assembly in the same connected state as depicted in FIG. 1.
Figure 3:
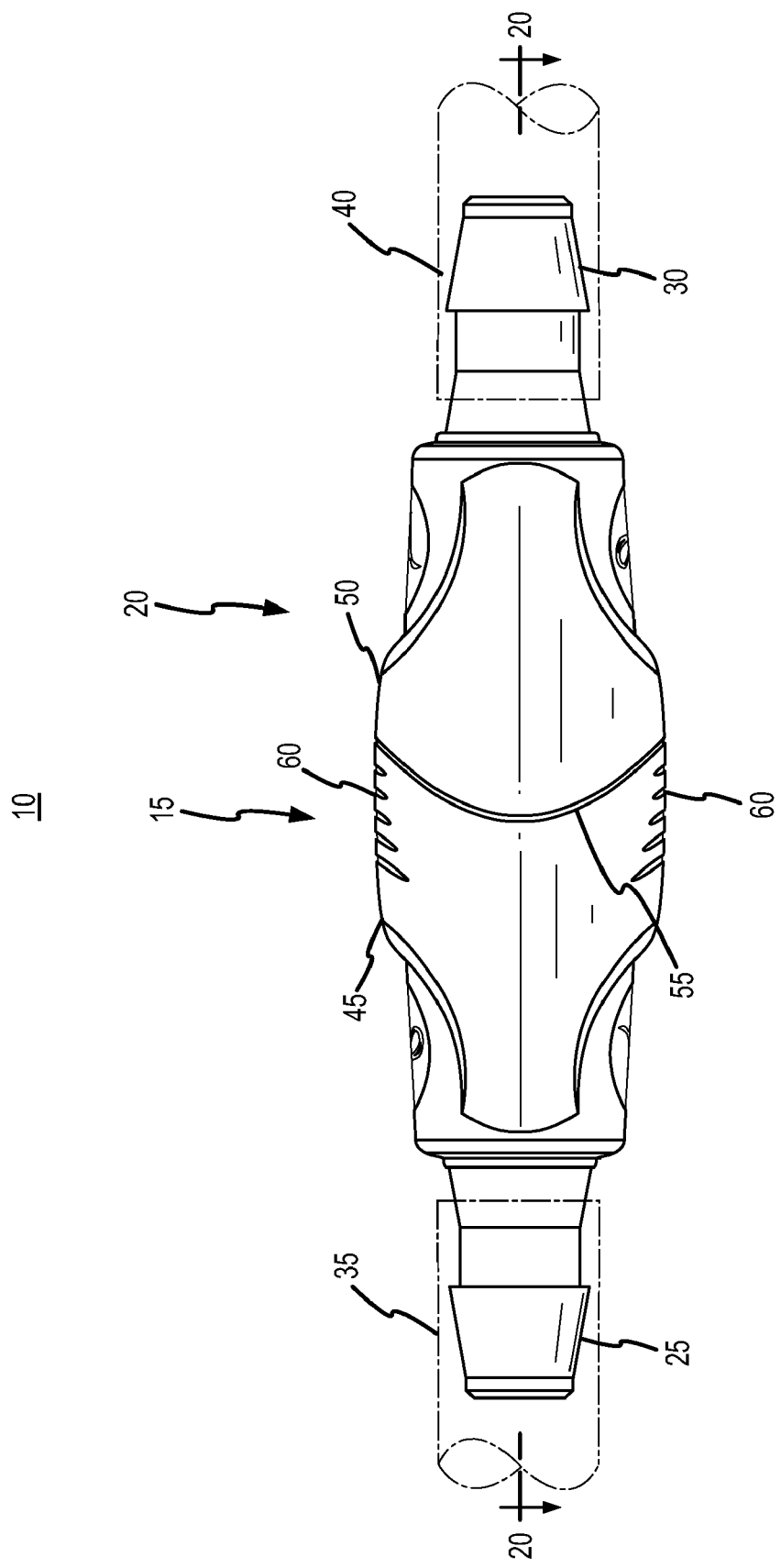
FIG. 3 is a side elevation of the coupling assembly in the same connected state depicted in FIG. 1.
Figure 4:
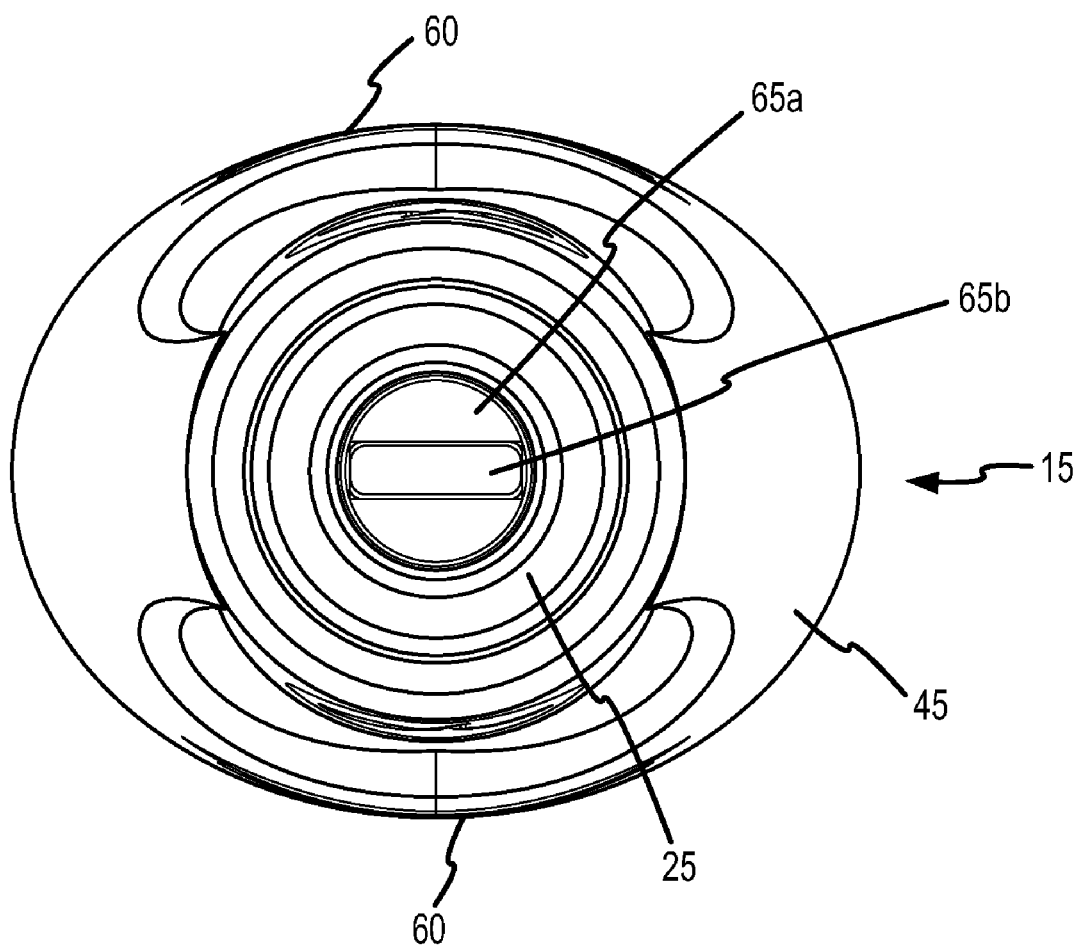
FIG. 4 is an end elevation of the coupling assembly in the same connected state depicted in FIG. 1 and as viewed from the male coupler end.

For a discussion of the first embodiment of the quick disconnect coupling assembly 10 of the present invention, reference is made to FIGS. 1-4. FIG. 1 is an isometric view of the quick disconnect coupling assembly 10, wherein the male coupler 15 and female coupler 20 are connected. FIG. 2 is a top plan of the coupling assembly 10 in the same connected state as depicted in FIG. 1. While a bottom plan of the coupling assembly 10 is not provided, it should be understood that it would appear identical to the view depicted in FIG. 2. FIG. 3 is a side elevation of the coupling assembly 10 in the same connected state depicted in FIG. 1. While a view of the opposite side of the coupling assembly 10 is not provided, it should be understood that it would appear identical to the view depicted in FIG. 3. FIG. 4 is an end elevation of the coupling assembly 10 in the same connected state depicted in FIG. 1 and as viewed from the male coupler end. While a view of the coupling assembly 10 as viewed from the female coupler end is not provided, it should be understood that it would appear identical to the view depicted in FIG. 4.

As shown in FIG. 1-3, the quick disconnect coupling assembly 10 includes a male coupler 15 and a female coupler 20. Each coupler 15, 20 includes a barbed end 25, 30 for insertion into, and connection with, a fluid conduit 35, 40 such as medical grade flexible tubing. Each coupler 15, 20 includes a housing or shroud 45, 50 that forms the exterior shell of each coupler 15, 20. When the couplers 15, 20 are connected, as depicted in FIGS. 1-3, the housings 45, 50 form a body that is semi-elliptical or egg-shaped as viewed from above or below, as shown in FIG. 2. When the couplers 15, 20 are connected, the joining ends of the housings 45, 50 of each coupler 15, 20 abut along a seam 55 that arcuately transitions as the seam 55 circumferentially latitudinally extends about the exterior shell of the coupling assembly 10 such that the male coupler housing 45 arcuately extends past the mid-point of the coupling assembly 10 at the top and bottom of the coupling assembly 10, and the female coupler housing 50 arcuately extends past the mid-point of the coupling assembly 10 at the sides of the coupling assembly 10. The male coupling housing 45 includes a group of latitudinally extending slots 60 that provide friction contact points for a user's fingers when disengaging an engagement mechanism (shown in later described figures) that hold the couplers 15, 20 together.

As can be understood from FIGS. 1 and 4, a fluid flow path 65 extends through the coupler assembly 10 from the male coupler barbed end 25 to the female coupler barbed end 30. In one embodiment, as indicated in FIG. 4, and as will be described with greater detail later in this Detailed Description, the fluid flow path 65 transitions from a circular cross-section 65a to a rectangular cross-section 65b and back to a circular cross-section 65a as the fluid flow path 65 extends through the coupler assembly 10.

Figure 5:
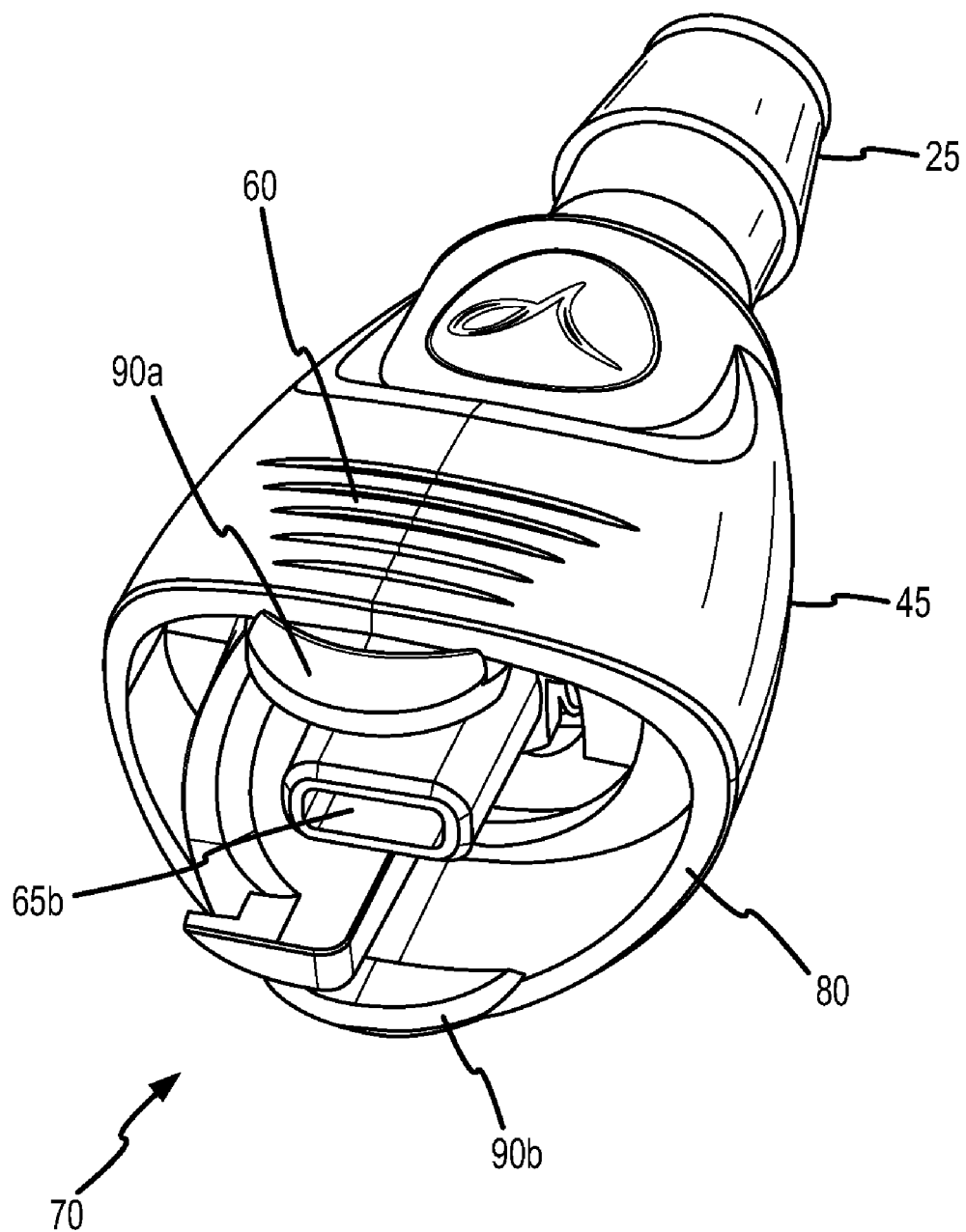
FIG. 5 is an isometric view of the male coupler as viewed from the joining side of the male coupler.
Figure 6:
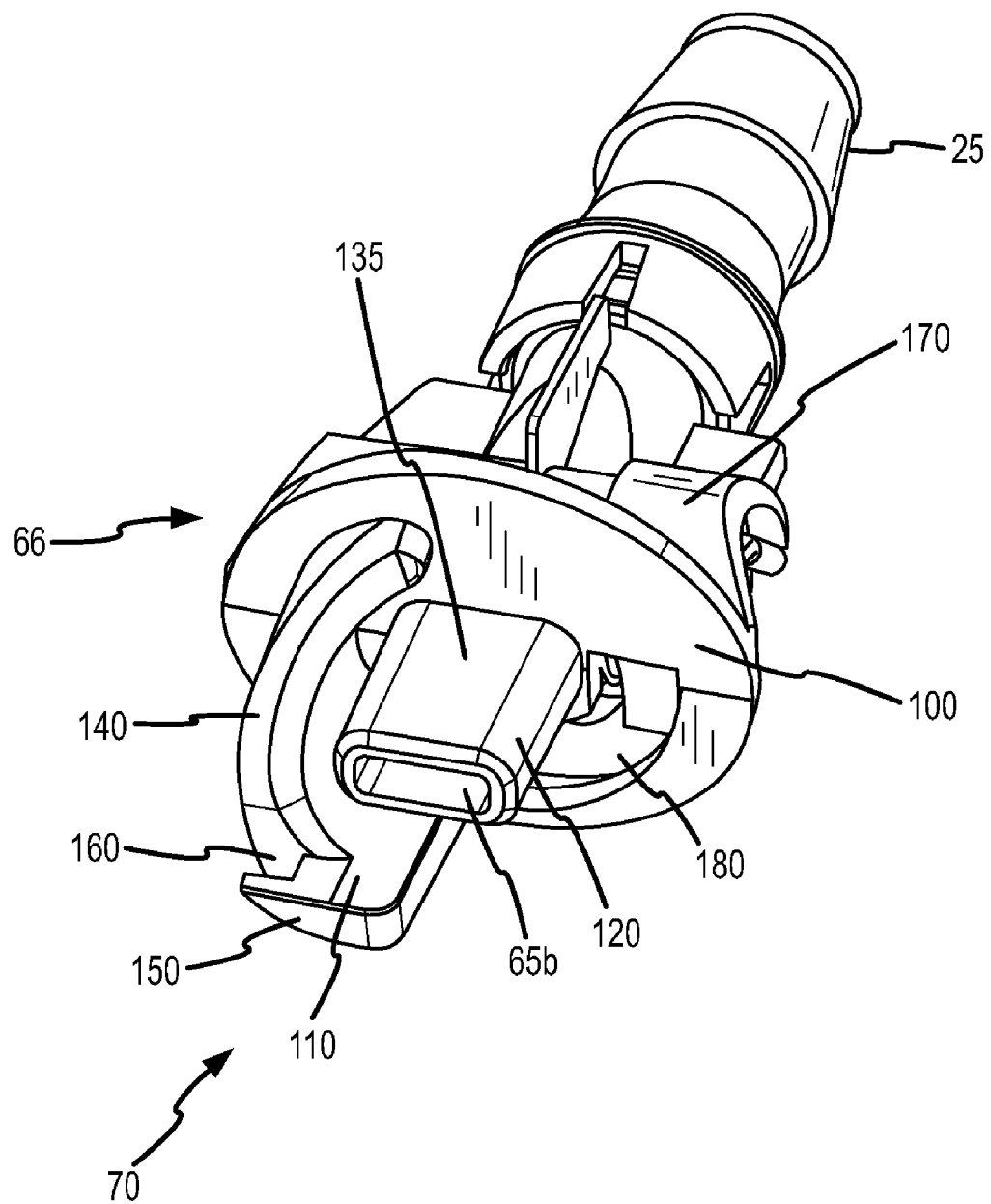
FIG. 6 is the same view of the male coupler depicted in FIG. 5, except the male coupler housing has been removed from the male coupler to reveal the male barrel.
Figure 7:
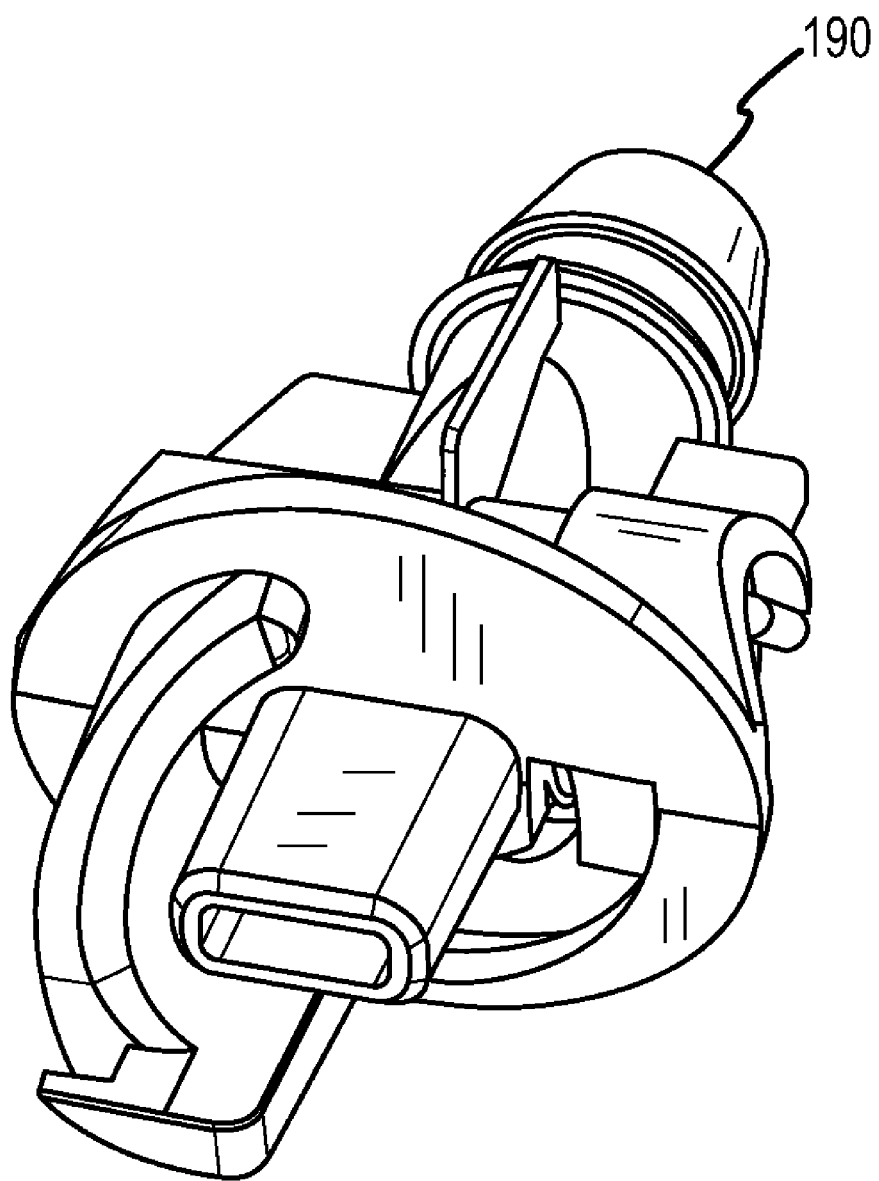
FIG. 7 is the same view of the male barrel depicted in FIG. 6, except the barbed end has been removed from the male barrel.
Figure 8:
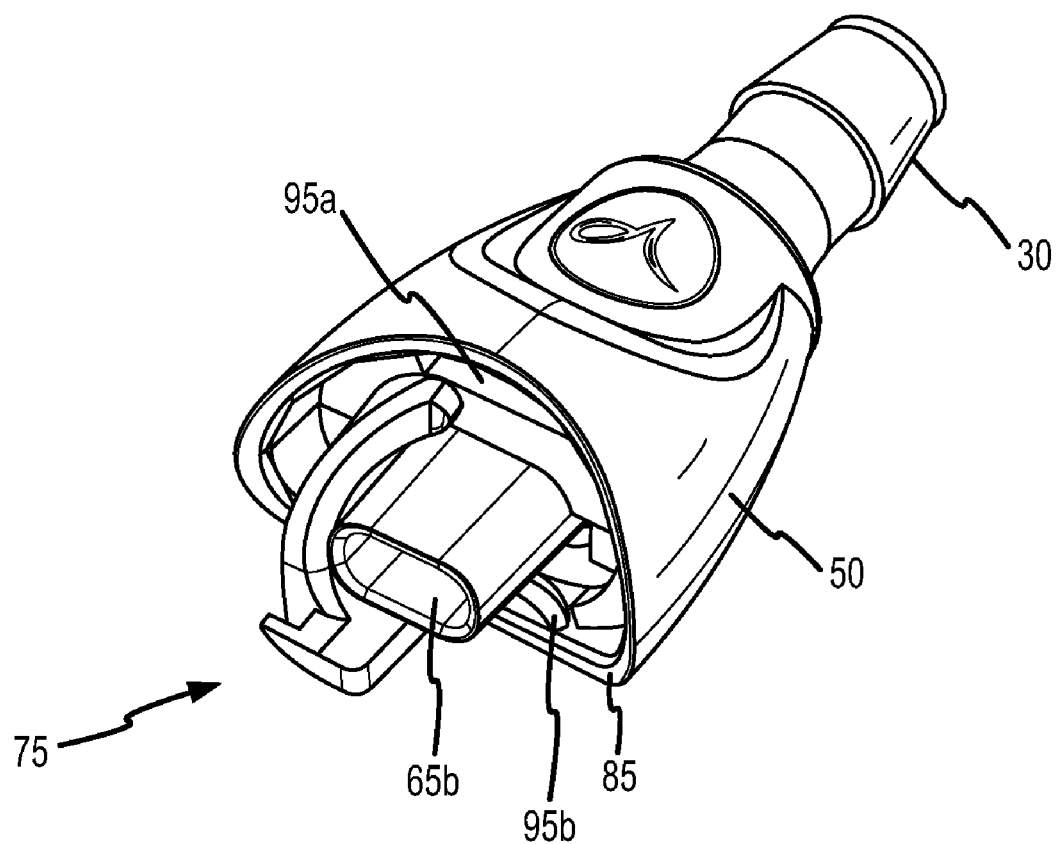
FIG. 8 is an isometric view of the female coupler as viewed from the joining side of the female coupler.
Figure 9:
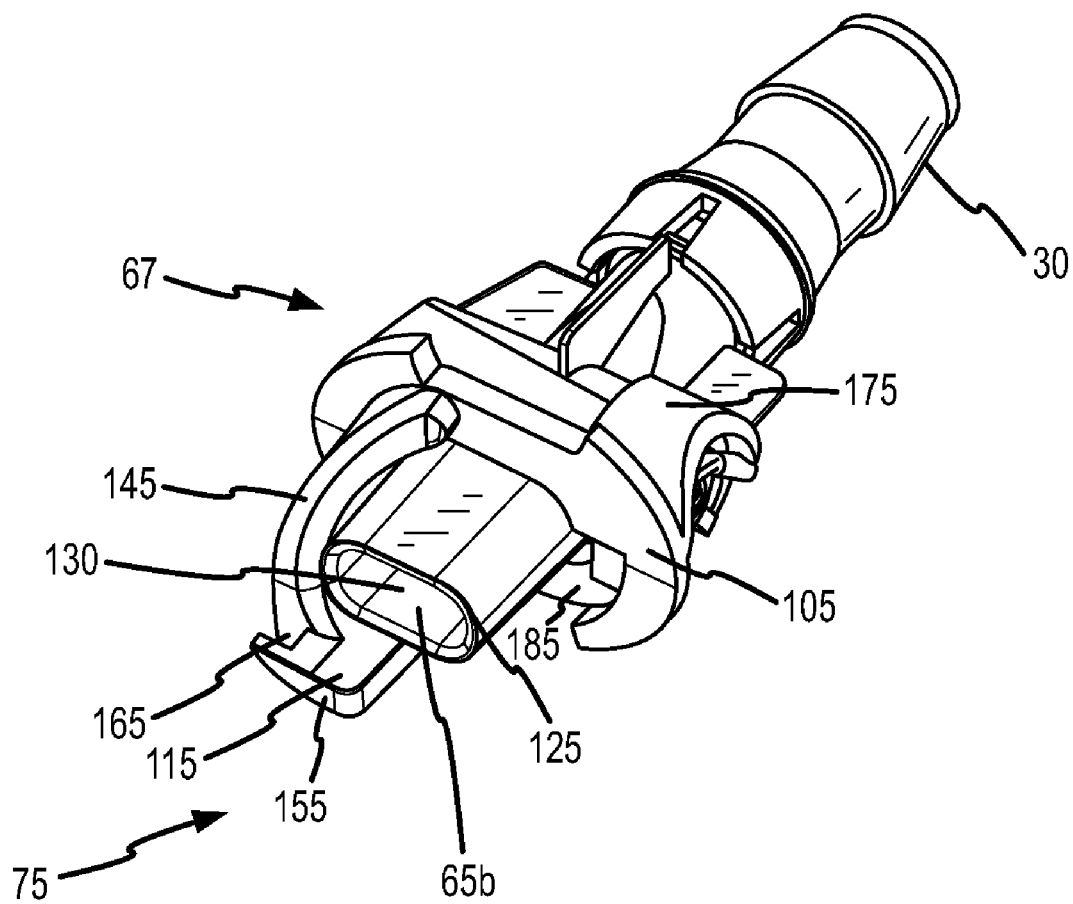
FIG. 9 is the same view of the female coupler depicted in FIG. 8, except the female coupler housing has been removed from the female coupler to reveal the female barrel.
Figure 10:
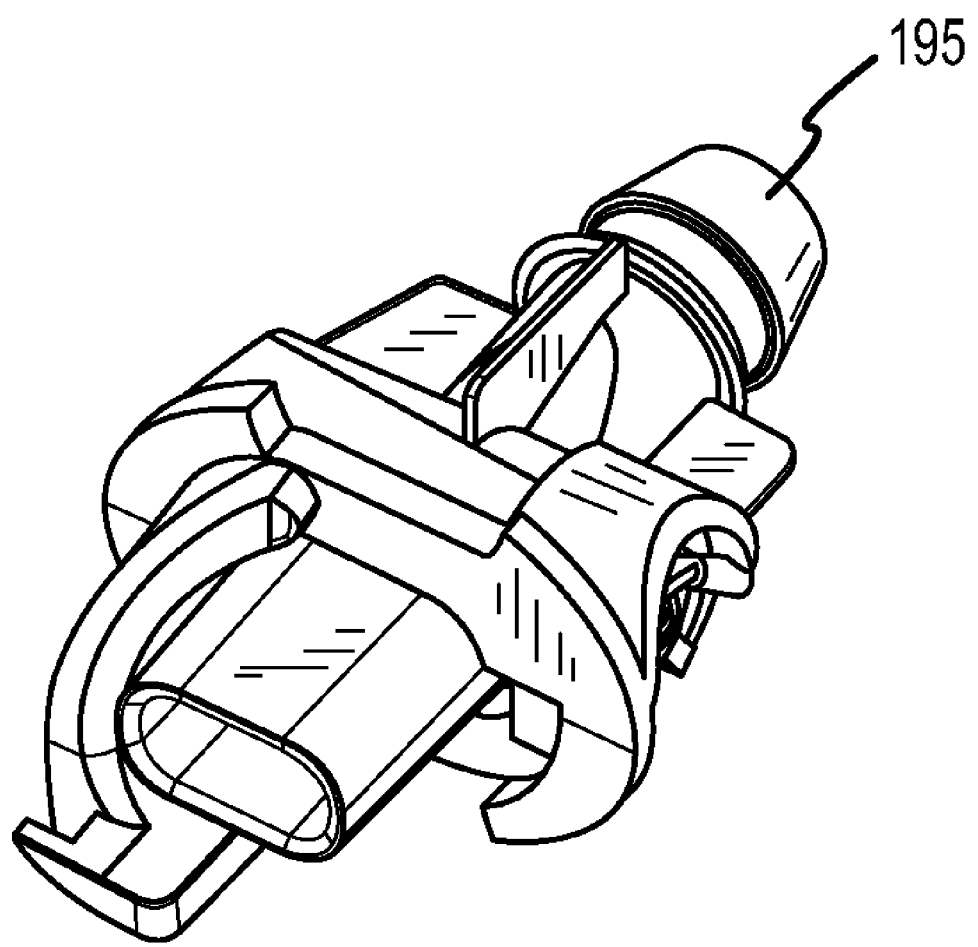
FIG. 10 is the same view of the female barrel depicted in FIG. 8, except the barbed end has been removed from the female barrel.

For a detailed discussion of the male coupler 15 and female coupler 20 as each coupler 15, 20 appears when disconnected from the other coupler 15, 20, reference is made to FIGS. 5-10. FIG. 5 is an isometric view of the male coupler 15 as viewed from the joining side of the male coupler 15. FIG. 6 is the same view of the male coupler 15 depicted in FIG. 5, except the male coupler housing 45 has been removed from the male coupler 15 to reveal the male barrel 66. FIG. 7 is the same view of the male barrel 66 depicted in FIG. 6, except the barbed end 25 has been removed from the male barrel 66. FIG. 8 is an isometric view of the female coupler 20 as viewed from the joining side of the female coupler 20. FIG. 9 is the same view of the female coupler 20 depicted in FIG. 8, except the female coupler housing 50 has been removed from the female coupler 20 to reveal the female barrel 67. FIG. 10 is the same view of the female barrel 67 depicted in FIG. 6, except the barbed end 30 has been removed from the female barrel 67.

As shown in FIGS. 5 and 8, the male and female couplers 15, 20 each have joining ends 70, 75 that mate with, and couple to, the joining end 70, 75 of the other coupler 15, 20. Each joining end 70, 75 includes a seam face 80, 85 that forms a leading surface of each housing 45, 50. When the couplers 15, 20 are connected together, as illustrated in FIGS. 1-3, the seam faces 80, 85 abut to form the seam 55.

As illustrated in FIGS. 5 and 8, the male housing 45 includes upper and lower engagement lips 90a, 90b that extend forwardly from the male housing 45 to engage with upper and lower engagement ridges 95a, 95b formed in the inner surface of the female housing 50. When the joining ends 70, 75 are pushed together in order connect the couplers 15, 20, the lips 90 and ridges 95 engage to maintain the couplers 15, 20 in a connected state. The lips 90 and ridges 95 form the previously mentioned engagement mechanism. The lips 90 are disengaged from the ridges 95 by pressing inward on the slots 60 and pulling the couplers 15, 20 longitudinally away from each other.

As indicated in FIGS. 6 and 9, the male and female couplers 15, 20 respectively include male and female barrels 66, 67 within the housings 45, 50. Each joining end 70, 75 of the male and female barrels 66, 67 includes a faceplate 100, 105, an arm or structural member 110, 115, and a neck 120, 125. Each neck 120, 125 protrudes forwardly from its respective faceplate 100, 105. The rectangular cross-sectioned fluid flow path 65b extends through the longitudinal center of each neck 120, 125. The fluid flow path 65b extends through the female neck 125 via a longitudinally extending orifice 130 that is sufficiently oversized to receive the outer circumferential surface 135 of the male neck 120 when the male neck 120 is plugged into the orifice 130 of the female neck 125. In one embodiment, the outer circumferential surface 135 of the male neck 120 and the orifice 130 of the female neck 125 are sufficiently close in size to form a fluid tight fit when the male neck 120 is plugged into the female neck 125. In one embodiment, an o-ring extends about the outer circumferential surface 135 of the male neck 120 to provide a fluid tight fit when the male neck 120 is received within the orifice 130 of the female neck 125.

As depicted in FIGS. 6 and 9, each structural member 110, 115 extends forwardly from its respective faceplate 100, 105. In one embodiment, each structural member 110, 115 includes an arcuate portion 140, 145 that arcuately sweeps from the faceplate 100, 105 to a point near the tip 150, 155 of the structural member 110, 115. Each arcuate portion 140, 145 acts as an alignment key to achieve proper alignment between the male and female couplers 15, 20 when being coupled together. In one embodiment, each tip 150, 155 of a structural member 110, 115 includes a groove or slot 160, 165 for mating with a slot or groove on an extreme end of a lever arm of a valve as described later in this Detailed Description.

As shown in FIGS. 6 and 9, each barrel 66, 67 includes a valve 170, 175 located along the fluid flow path 65 between the barbed end 25, 30 and the neck 120, 125 of each barrel 66, 67. The valves 170, 175 will be discussed in greater detail later in this Detailed Description.

As illustrated in FIGS. 6 and 9, each faceplate 100, 105 includes an opening 180, 185. Each opening 180, 185 serves as a passage by which the structural member 110, 115 of the other barrel 66, 67 encounters a valve lever arm, as discussed in greater detail later in this Detailed Description.

As can be understood from a comparison between FIGS. 6, 9, 7 and 10, in one embodiment, the barbed ends 25, 30 are rotatable relative to the barrels 66, 67, yet sealable. The barbed ends 25, 30 friction fit onto sub-ends 190, 195. In one embodiment, each barbed end 25, 30 is formed from a generally hard and rigid material such as polycarbonate, polycarbonate blend, or other similar polymers, and each sub-end 190, 195 is formed from a generally soft, pliable and resilient material such as high density polyethylene ("HDPE"), acetale, or other similar polymers. This arrangement eliminates the need for an o-ring to form fluid tight connections between the barbed ends 25, 30 and the sub-ends 190, 195. In other embodiments, the barbed ends 25, 30 and sub-ends 190, 195 are formed from the same hard and rigid material such as polycarbonate, polycarbonate blend, or other similar polymers and are provided with one or more o-rings to create fluid tight connections between the barbed ends 25, 30 and the sub-ends 190, 195. In either case, having a configuration with barbed ends 25, 30 that are rotatable relative to the sub-ends 190, 195, yet sealable with the sub-ends 190, 195, allows a fluid conduit 35, 40 to pivot/rotate about the longitudinal axis of a sub-end 190, 195 without jeopardizing the sealed connection between the fluid conduit 35, 40 and its respective coupler 15, 20.

In one embodiment, the barbed ends 25, 30 are an integral formed as part of the barrels 66, 67 such that there are no sub-ends 190, 195. As a result, the barbed ends 25, 30 are not removable from the barrels 66, 67.

Figure 11:
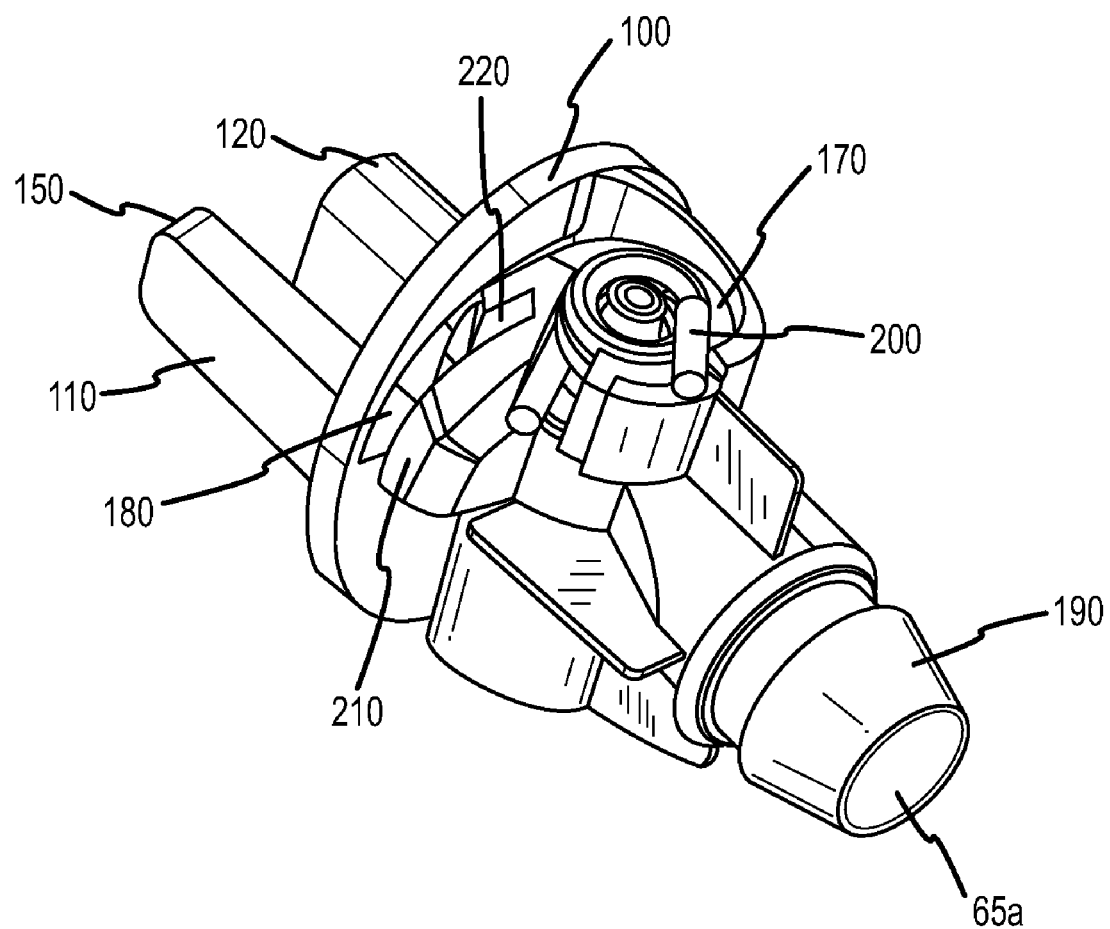
FIG. 11 is an isometric view of the male barrel as viewed from the fluid conduit connecting side of the male barrel.
Figure 12:
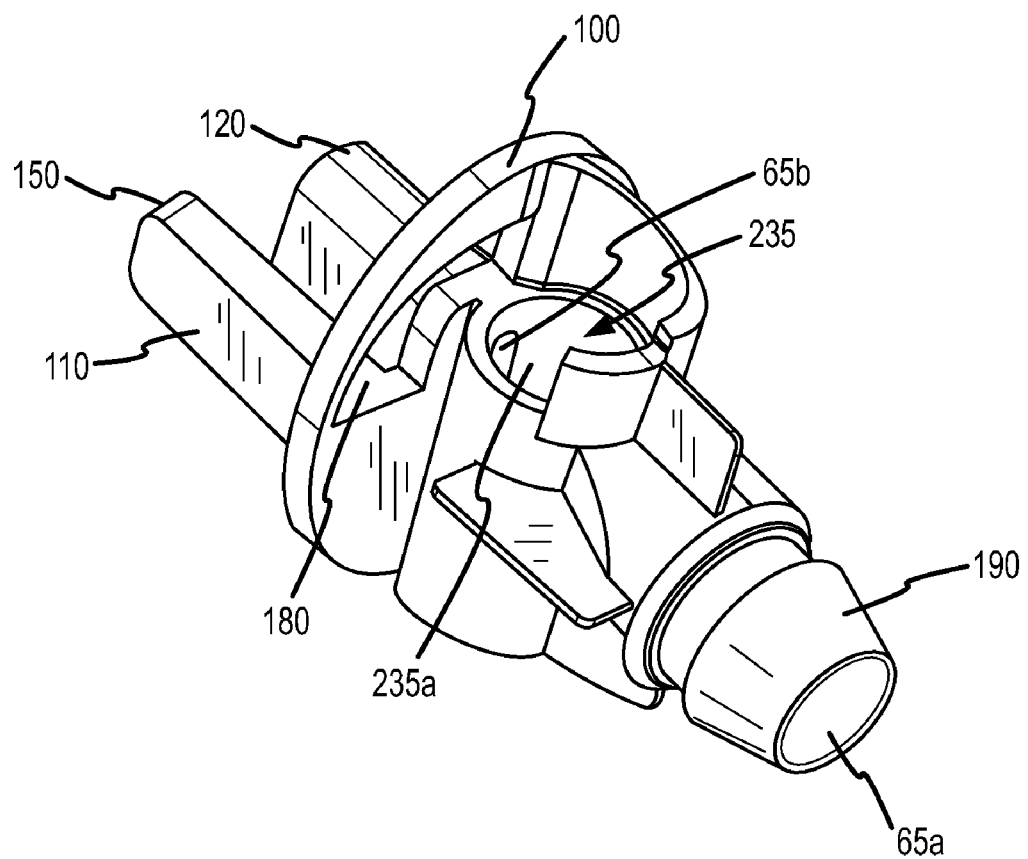
FIG. 12 is the same view of the male barrel depicted in FIG. 11, except the valve has been removed from the male barrel.
Figure 13:
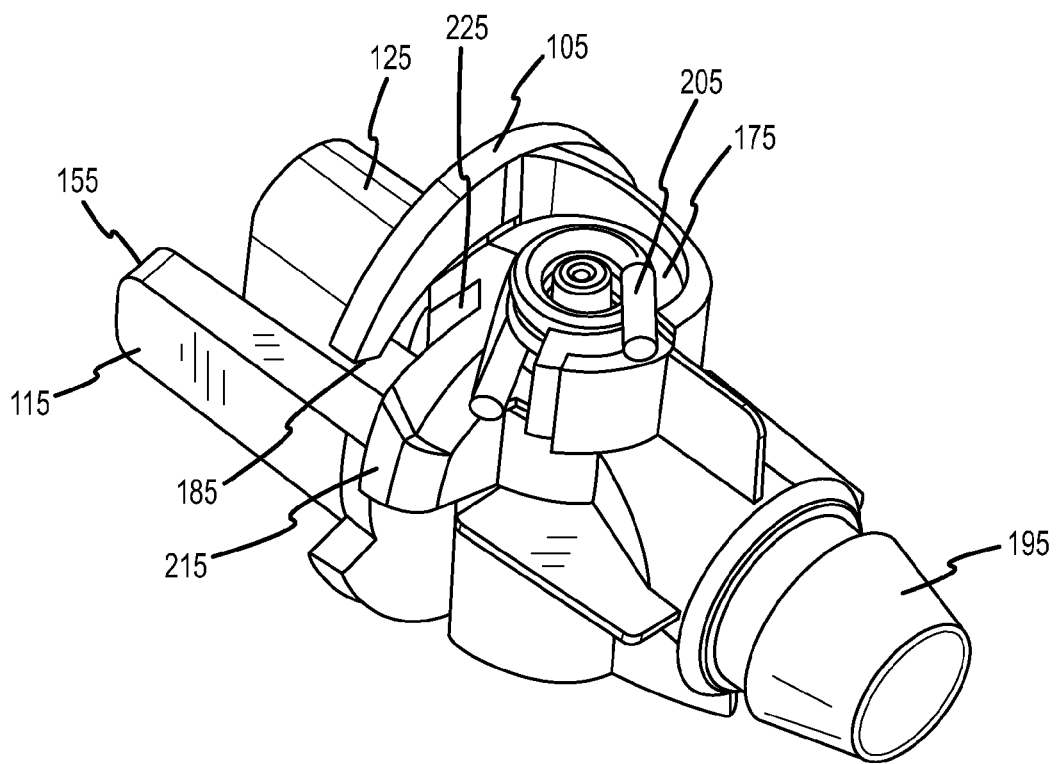
FIG. 13 is an isometric view of the female barrel as viewed from the fluid conduit connecting side of the female barrel.
Figure 14:
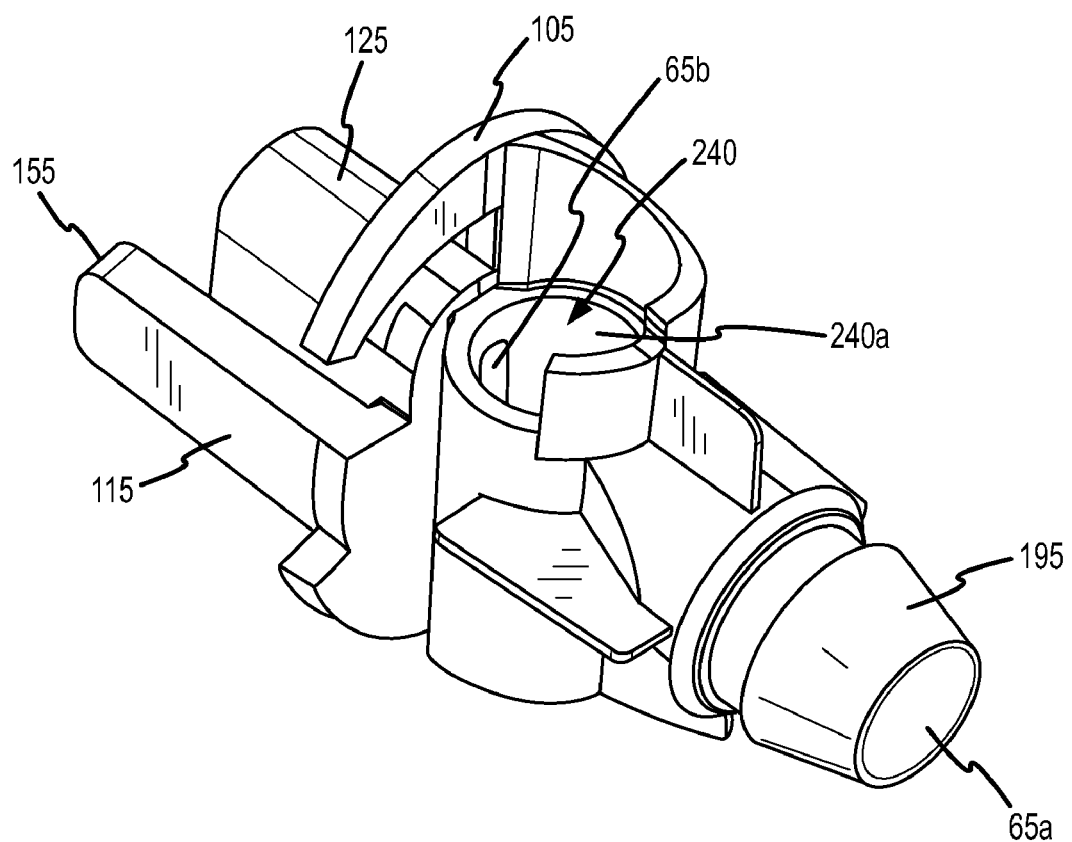
FIG. 14 is the same view of the female barrel depicted in FIG. 13, except the valve has been removed from the female barrel.
Figure 15:
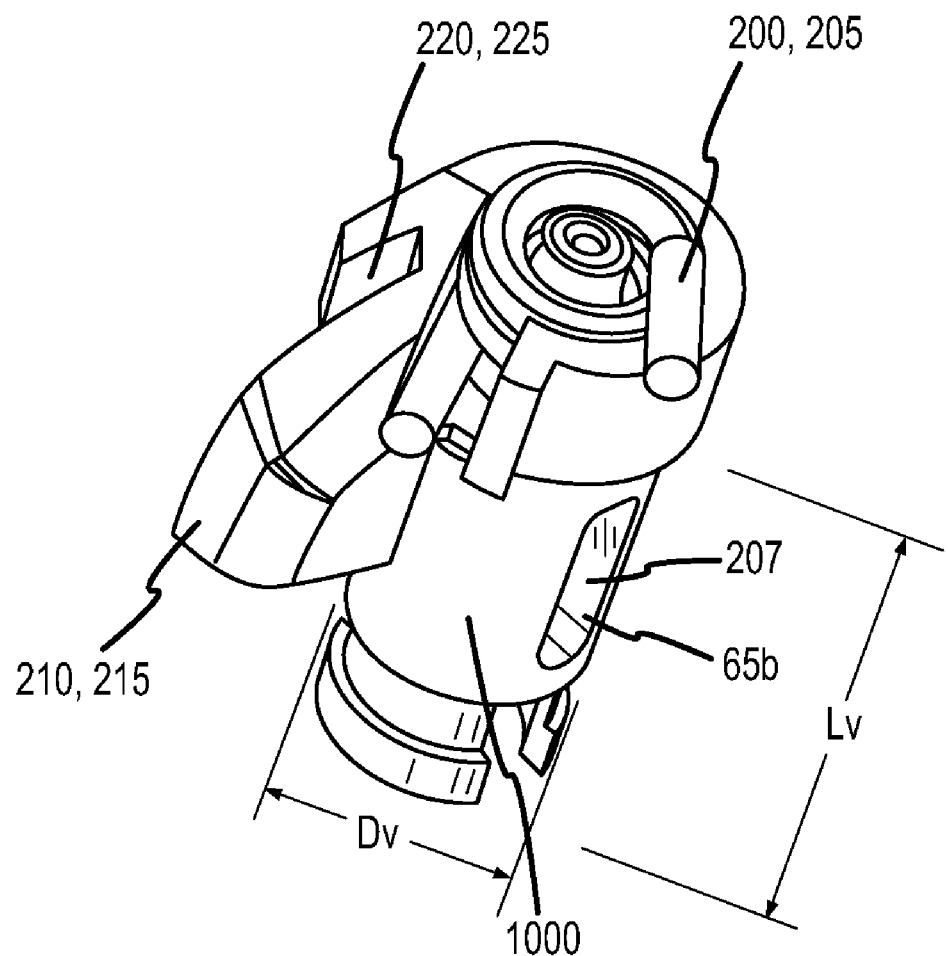
FIG. 15 is an isometric view of a valve and its biasing mechanism or spring as it would appear in FIG. 11 or 13 were the rest of the barrel removed from about the valve.
Figure 16:
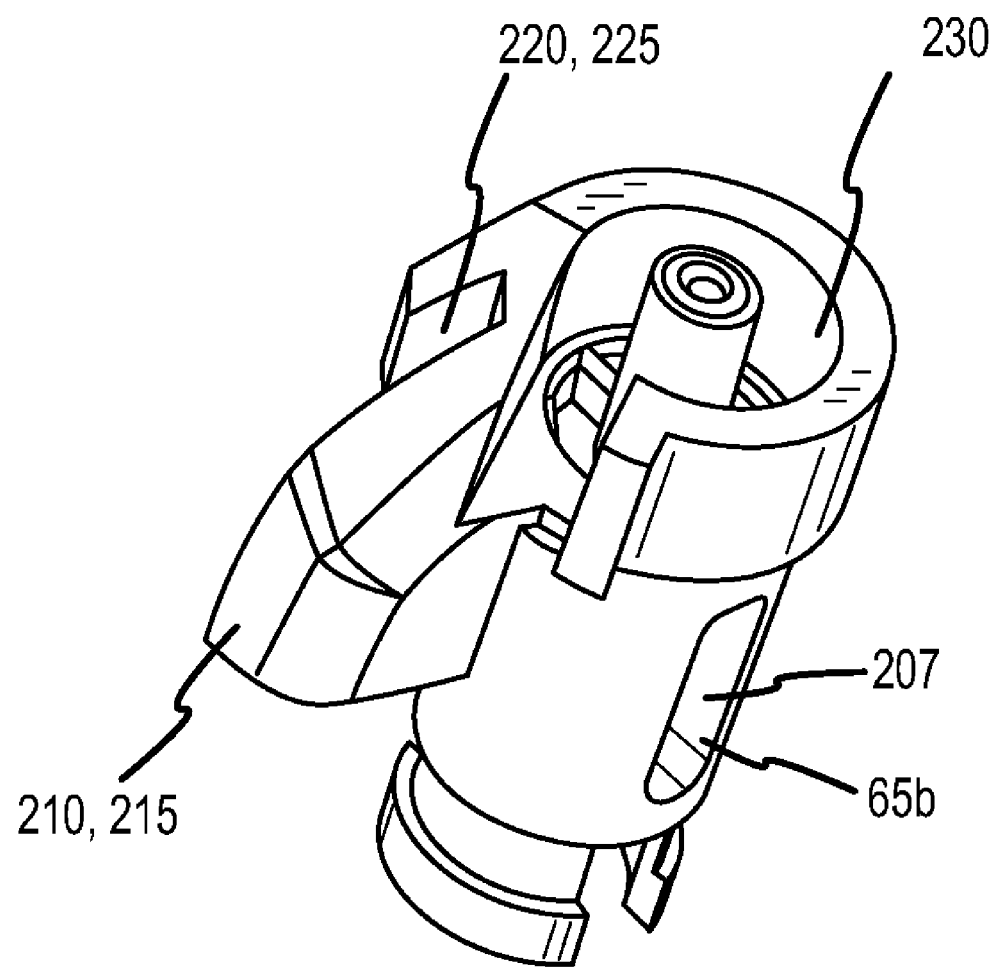
FIG. 16 is the same view of the valve depicted in FIG. 15, except the spring has been removed from the valve.

For a better understanding of the valve configuration of each barrel 66, 67, reference is made to FIGS. 11-16. FIG. 11 is an isometric view of the male barrel 66 as viewed from the fluid conduit connecting side of the male barrel 66. FIG. 12 is the same view of the male barrel 66 depicted in FIG. 11, except the valve 170 has been removed from the male barrel 66. FIG. 13 is an isometric view of the female barrel 67 as viewed from the fluid conduit connecting side of the female barrel 67. FIG. 14 is the same view of the female barrel 67 depicted in FIG. 13, except the valve 175 has been removed from the female barrel 67. FIG. 15 is an isometric view of a valve 170, 175 and its biasing mechanism or spring 200, 205 as it would appear in FIG. 11 or 13 were the rest of the barrel 66, 67 removed from about the valve 170, 175. FIG. 16 is the same view of the valve 170, 175 depicted in FIG. 15, except the spring 200, 205 has been removed from the valve 170, 175.

As indicated in FIGS. 11 and 13, each barrel 66, 67 includes a valve 170, 175 that is located between the back surface of the faceplate 100, 105 and the sub-end 190, 195. As shown in FIGS. 15 and 16, each valve 170, 175 has a cylindrical or barrel shaped body and includes a non-circular shaped orifice 207 that extends through the body of the valve 170, 175 perpendicular to the longitudinal axis of the body of the valve 170, 175. In one embodiment, the orifice 207 is rectangular and oriented such that its longitudinal axis coincides with the longitudinal axis of the body of the valve 170, 175. The orifice 207 serves as part of the rectangular cross-section fluid flow path 65b in each barrel 66, 67.

As shown in FIGS. 11, 13, 15 and 16, each valve 170, 175 includes a lever arm 210, 215 and a biasing mechanism or spring 200, 205. Each lever arm 210, 215 radially extends outward from the valve 170, 175 and includes a groove or slot 220, 225 that mates with the groove or slot 160, 165 in the tip 150, 155 of the structural member 110, 115 of the other barrel 66, 67, as will be discussed more fully later in this Detailed Description. Each biasing mechanism or spring 200, 205 acts between structural features of the valve 170, 175 and structural features of the barrel 66, 67 to bias the lever arm 210, 215 towards the opening 180, 185 in the faceplate 100, 105 immediately adjacent the valve 170, 175. In one embodiment, the biasing mechanism 200, 205 is a helical spring 200, 205 that resides within a cylindrical recess 230 in an end of the valve 170, 175.

As indicated in FIGS. 12 and 14, each barrel 66, 67 includes a cylindrical opening 235, 240 that receives therein the body of the valve 170, 175 and serves as a valve seat for the valve 170, 175. The rectangular cross-section fluid flow path 65b penetrates each cylindrical opening 235, 240 to form a pair of rectangular openings 65b in the inner circumferential surface 235a, 240a of the cylindrical opening 235, 240. Each valve 170, 175 is pivotally displaceable about its longitudinal axis within its cylindrical opening or valve seat 235, 240 of a barrel 66, 67.

As can be understood from FIGS. 11-16, when the valve 170, 175 pivotally is displaced within the valve seat 235, 240 of a barrel 66, 67 such that the valve's lever arm 210, 215 is displaced away from the faceplate 100, 105 of the barrel 66, 67, the rectangular orifice 207 extending through each valve 170, 175 aligns with the rectangular openings 65b in the inner circumferential surface 235a, 240a of the valve seat 235, 240. As a result, the fluid flow path 65 extends uninterrupted through the barrel 66, 67 from the sub-end 190, 195 to the neck 120, 125. Conversely, when the valve 170, 175 pivotally displaced within the valve seat 235, 240 of a barrel 66, 67 such that the valve's lever arm 210, 215 is displaced towards the faceplate 100, 105 of the barrel 66, 67, the rectangular orifice 207 extending through each valve 170, 175 does not coincide to any extent with the rectangular openings 65b in the inner circumferential surface 235a, 240a of the valve seat 235, 240. As a result, the fluid flow path 65 is sealed off or interrupted at the location of the valve 170, 175.

Figure 17:
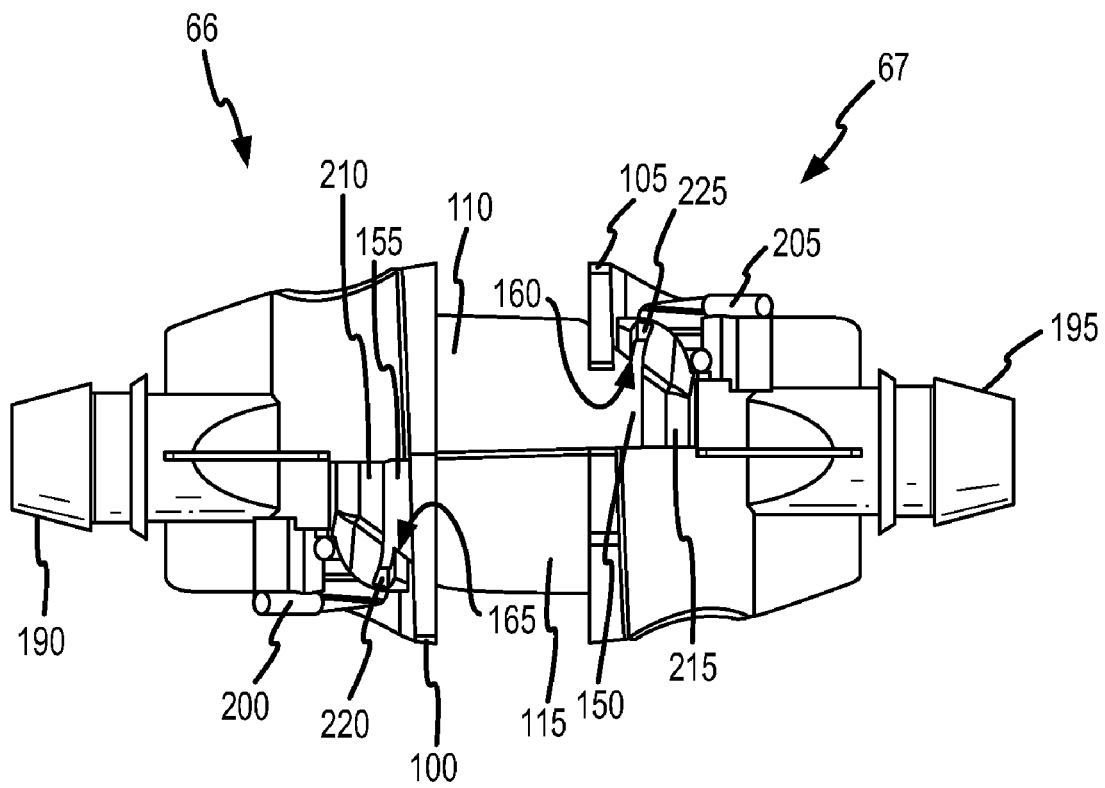
FIG. 17 is the same top plan of the coupling assembly as depicted in FIG. 2 and wherein the coupling assembly is in a connected state, except the housings and barbed ends have been removed to show the barrels.
Figure 18:
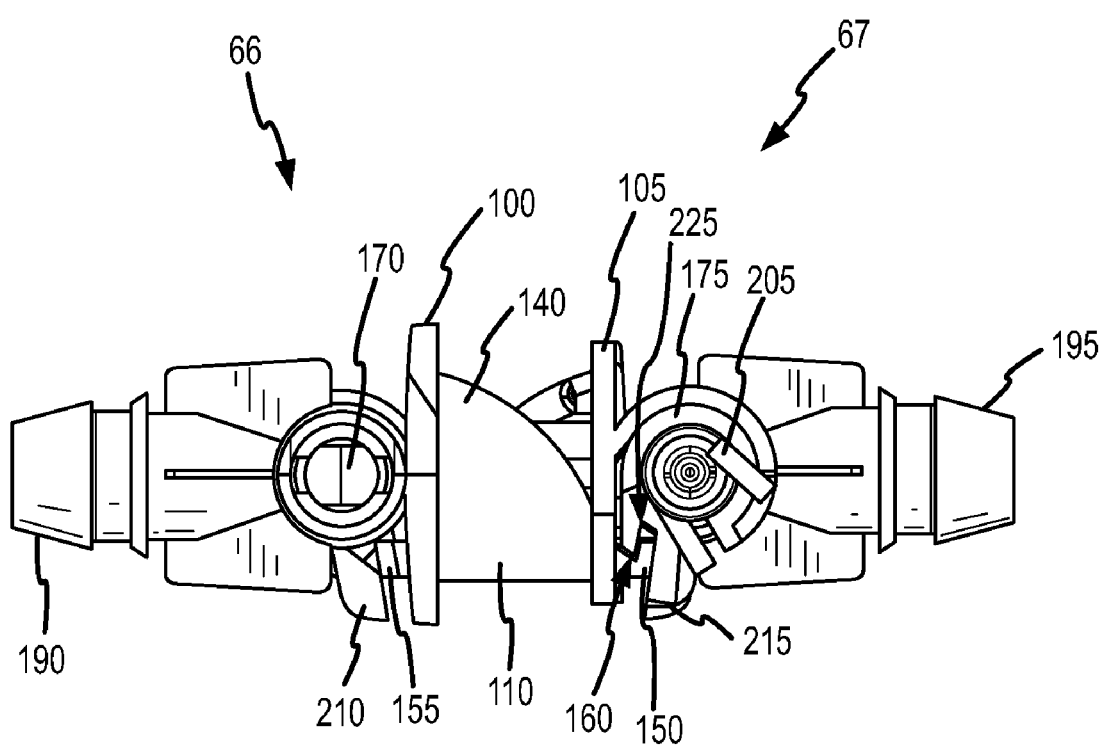
FIG. 18 is a side elevation of the barrels in the same connected state depicted in FIG. 17.
Figure 19:
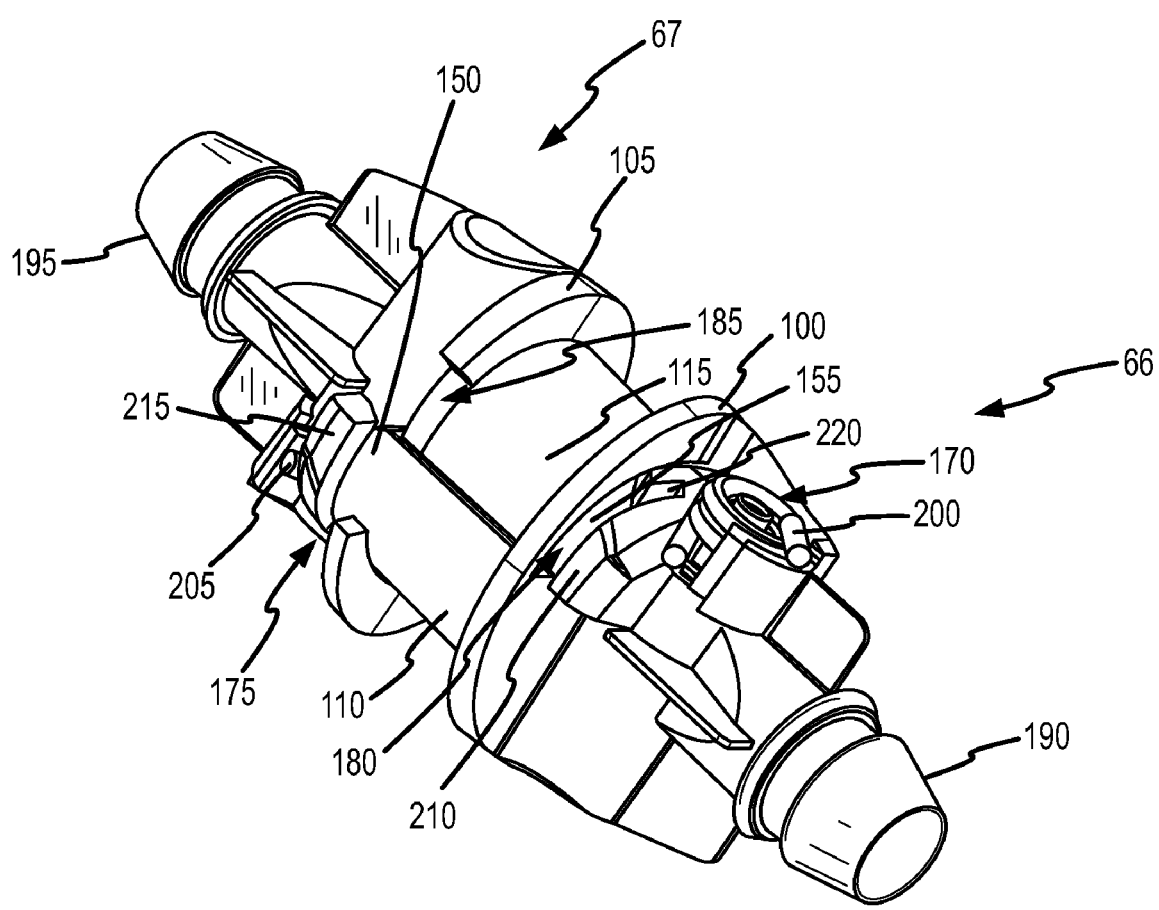
FIG. 19 is an isometric view of the barrels in the same connected state depicted in FIG. 17.
Figure 20:
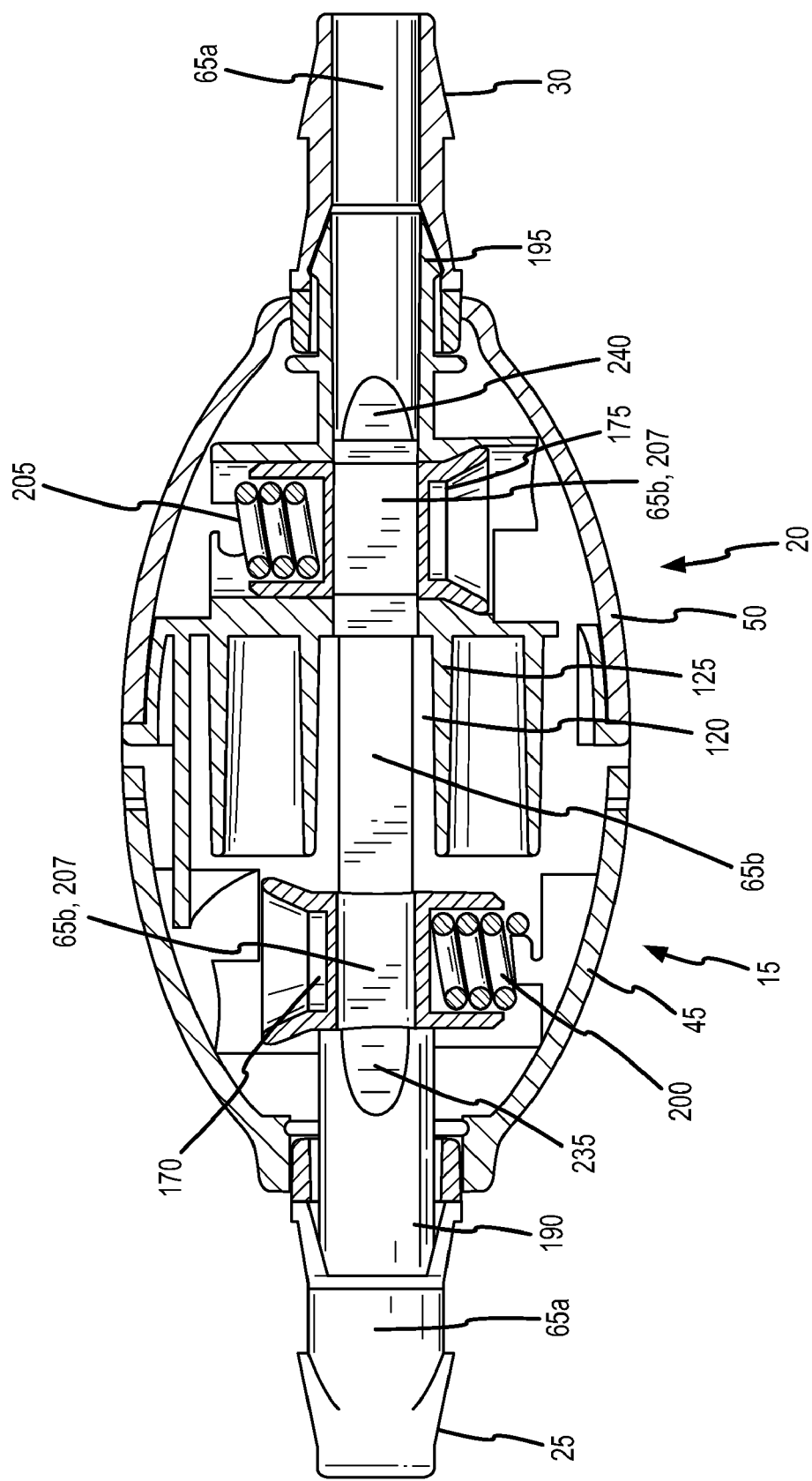
FIG. 20 is a cross-sectional top plan of the coupling assembly in a connected state as taken along section line 20-20 in FIG. 3.

For a better understanding of the interaction of the various components of the quick disconnect coupling assembly 10 when the male and female couplers 15, 20 are connected as illustrated in FIGS. 1-3, reference is made to FIGS. 17-19. FIG. 17 is the same top plan of the coupling assembly 10 as depicted in FIG. 2 and wherein the coupling assembly 10 is in a connected state, except the housings 45, 50 and barbed ends 25, 30 have been removed to show the barrels 66, 67. FIG. 18 is a side elevation of the barrels 66, 67 in the same connected state depicted in FIG. 17. FIG. 19 is an isometric view of the barrels 66, 67 in the same connected state depicted in FIG. 17. FIG. 20 is a cross-sectional top plan of the coupling assembly 10 in a connected state as taken along section line 20-20 in FIG. 3.

As can be understood from FIGS. 1-3, 5, 8 and 17-20, when the joining ends 70, 75 of the male and female couplers 15, 20 are pressed together, the male neck 120 is received within the orifice 130 of the female neck 125 to place the rectangular cross-section fluid flow path 65b of the male coupler 15 into fluid communication with the rectangular cross-section fluid flow path 65b of the female coupler. At the same time, the structural member 110 of the male barrel 66 passes through the faceplate opening 185 of the female barrel 67 to push the valve lever arm 215 of the female barrel 67 away from the faceplate 105 of the female barrel 67, and the structural member 115 of the female barrel 67 passes through the faceplate opening 180 of the male barrel 66 to push the valve lever arm 210 of the male barrel 66 away from the faceplate 100 of the male barrel 66. As a result, each valve 170, 175 pivots within its respective valve seat 235, 240 such that each rectangular valve orifice 207 aligns with the rectangular fluid flow paths 65b extending through the barrels 66, 67. In other words, each valve 170, 175 pivots from a closed position to an open position wherein the fluid flow path 65 extends in an uninterrupted path through the coupling assembly 10. As the structural members 110, 115 displace the valve lever arms 210, 215 such that the valves 170, 175 pivot towards the valve open position, the slot or groove 220, 225 on the end of each lever arm 210, 215 mates with the slot or groove 160, 165 on the tip 150, 155 of each structural member 110, 115. The mating of the slots or grooves 160, 165, 220, 225 locks the lever arms 210, 215 to the structural members 110, 115, thereby locking the valves 170, 175 pivotally in the open position. As previously discussed, the engagement mechanism 90, 95 on the male and female housings 45, 50 engage to maintain the couplers 15, 20 in the connected state depicted in FIGS. 1-3, 5, 8 and 17-20.

As shown in FIG. 20, when the couplers 15, 20 are connected together as depicted in FIGS. 1-3 and 17-19, the fluid flow path 65 extends uninterrupted through the coupling assembly 10 from the male barbed end 25 to the female barbed end 30. In one embodiment, as depicted in FIG. 20, the fluid flow path 65 transitions from a circular cross-section fluid flow path 65a to a rectangular cross-section fluid flow path 65b at fluid flow path transitions 235, 240 located at the following locations: (1) between the male barbed end 25 and the male valve 170; and between the female barbed end 30 and the female valve 175. As a result, in one embodiment, the rectangular cross-section fluid flow path 65b extends in a continuous non-varying path through the orifices 207 of each valve and the distance between the transitions 235, 240 including the necks 120, 125 of the male and female barrels 66, 67.

As can be understood from FIGS. 1-3, 5, 8 and 17-20, by pressing on the slots 60 on the outer surface of the male housing 45, the engagement mechanism 90, 95 is disengaged. With the engagement mechanism 90, 95 disengaged, the couplers 15, 20 are longitudinally displaced away from each other, which causes the male neck 120 to withdraw from within the orifice 130 of the female neck 125 and the structural members 110, 115 to pull away from the lever arms 210, 215 and withdraw from the faceplate openings 180, 185. As a result, each valve 170, 175 is biased via its respective spring 200, 205 to pivot to the closed position wherein the end of each valve lever arm 210, 215 resides near the faceplate 100, 105 and no portion of the each valve orifice 207 coincides with the rectangular fluid flow path 65b extending through each barrel 66, 67. Consequently, the valves 170, 175 automatically seal closed the fluid flow path 65 in each coupler 15, 20.

c. Second Embodiment of the Quick Disconnect Coupling Assembly

Figure 21:
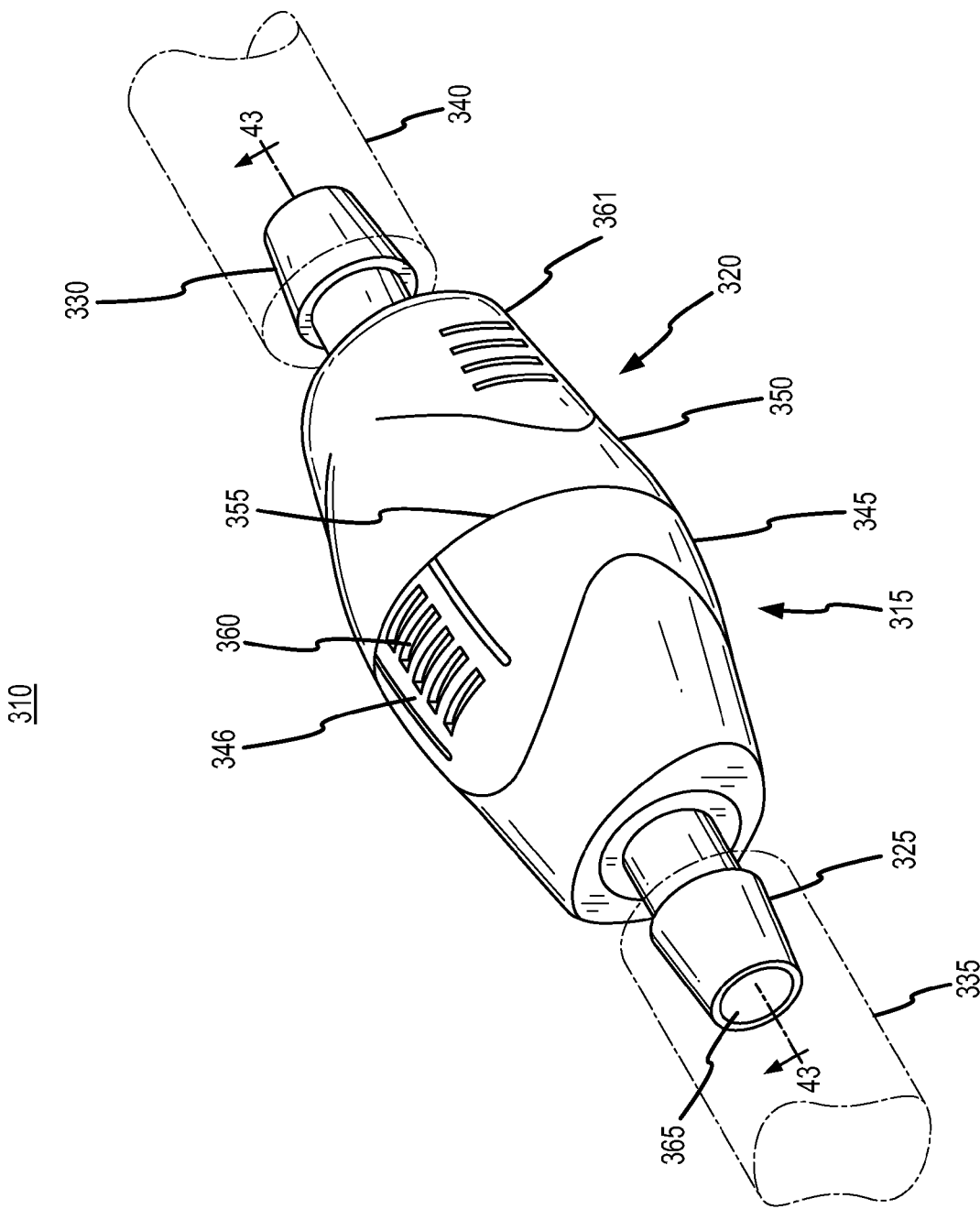
FIG. 21 is an isometric view of the quick disconnect coupling assembly, wherein the male coupler and female coupler are connected.
Figure 22:
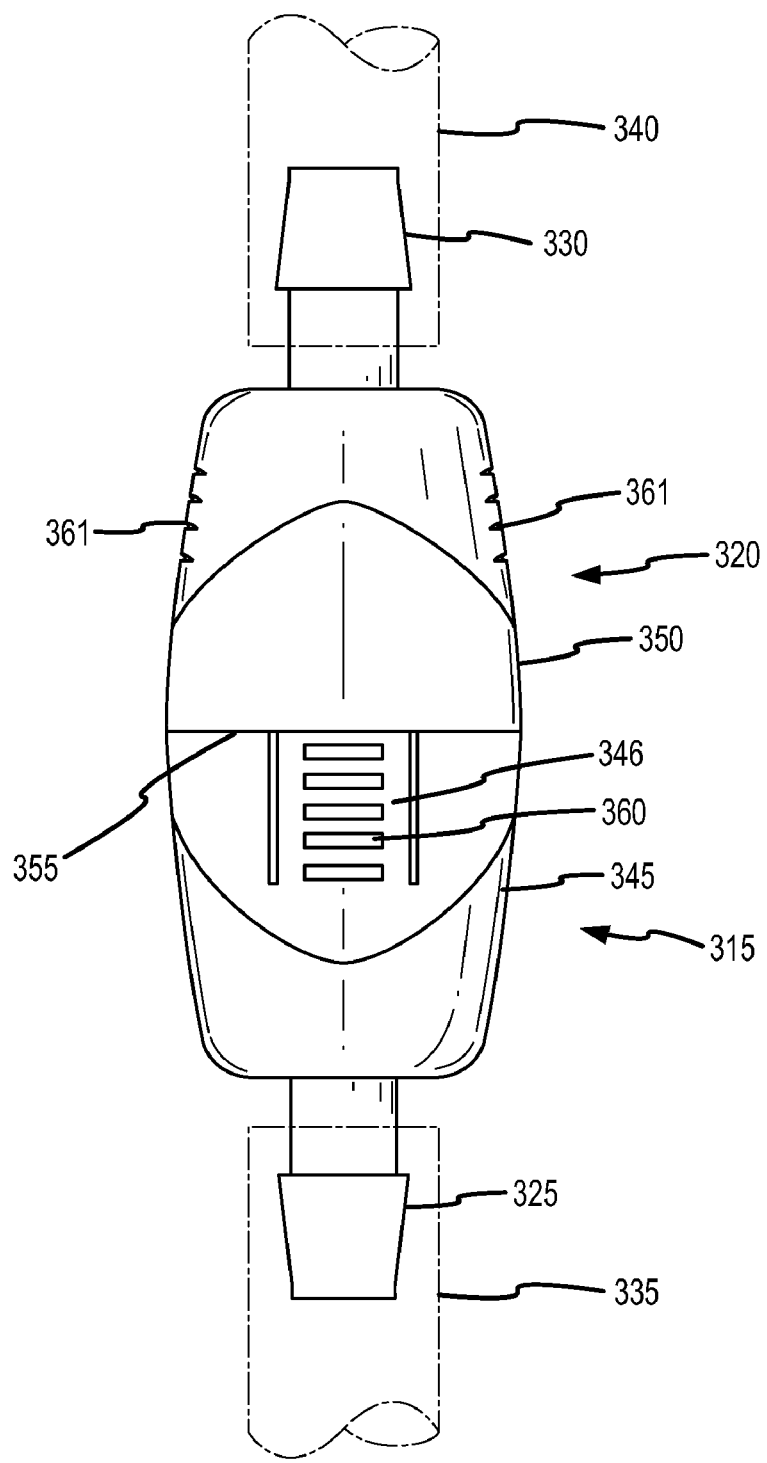
FIG. 22 is a top plan of the coupling assembly in the same connected state as depicted in FIG. 21.
Figure 23:
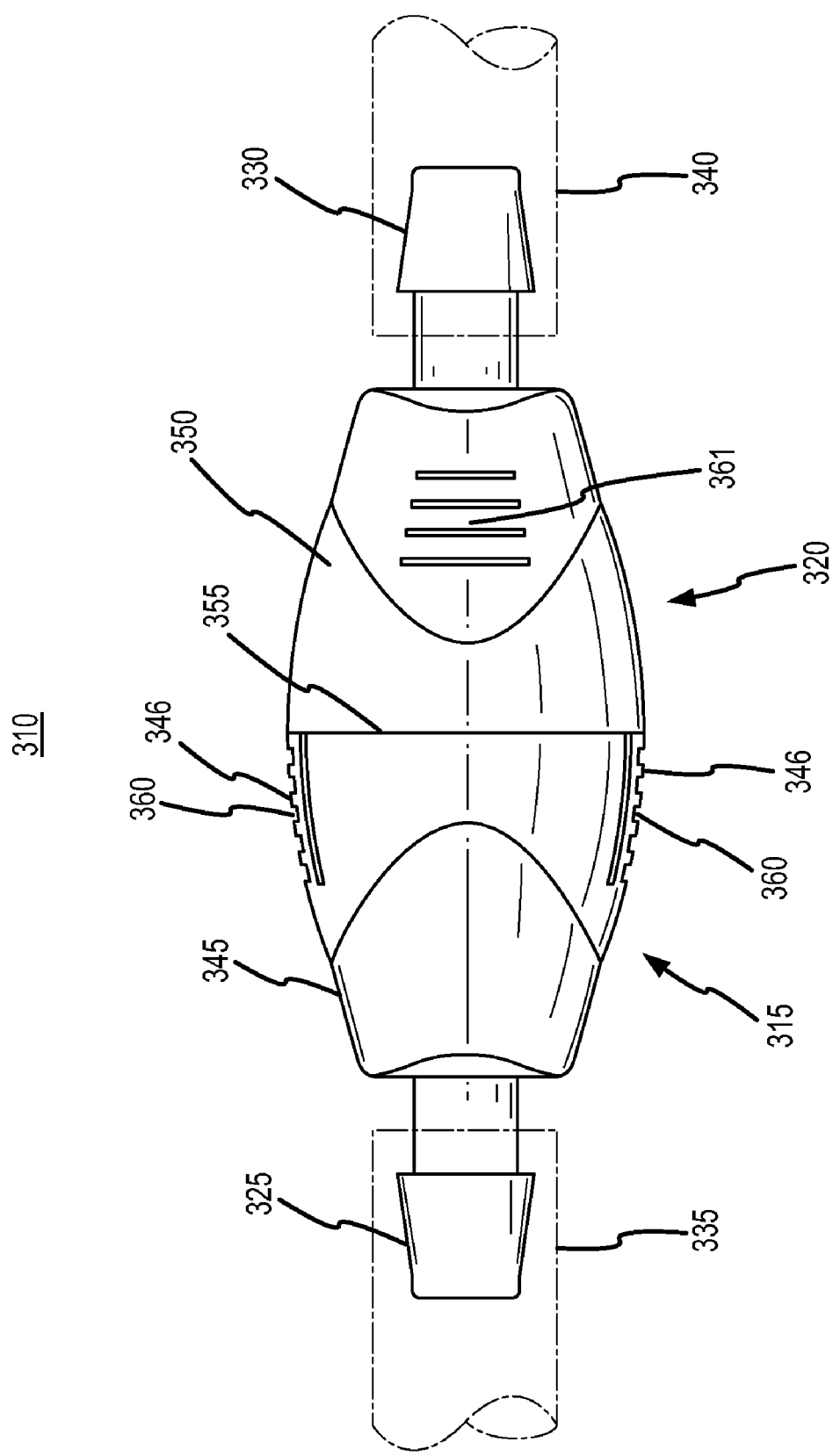
FIG. 23 is a side elevation of the coupling assembly in the same connected state depicted in FIG. 21.
Figure 24:
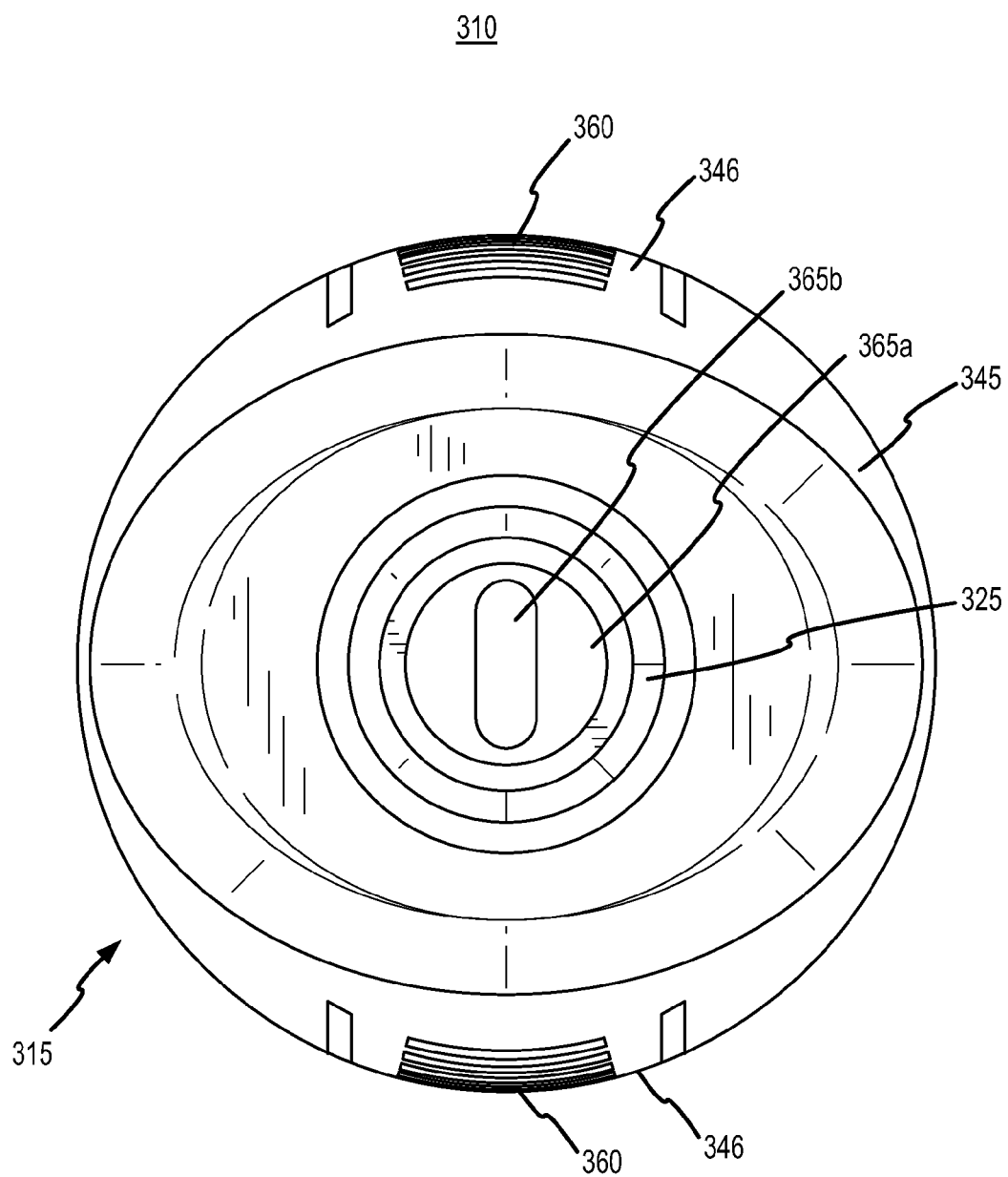
FIG. 24 is an end elevation of the coupling assembly in the same connected state depicted in FIG. 21 and as viewed from the male coupler end.
Figure 25:
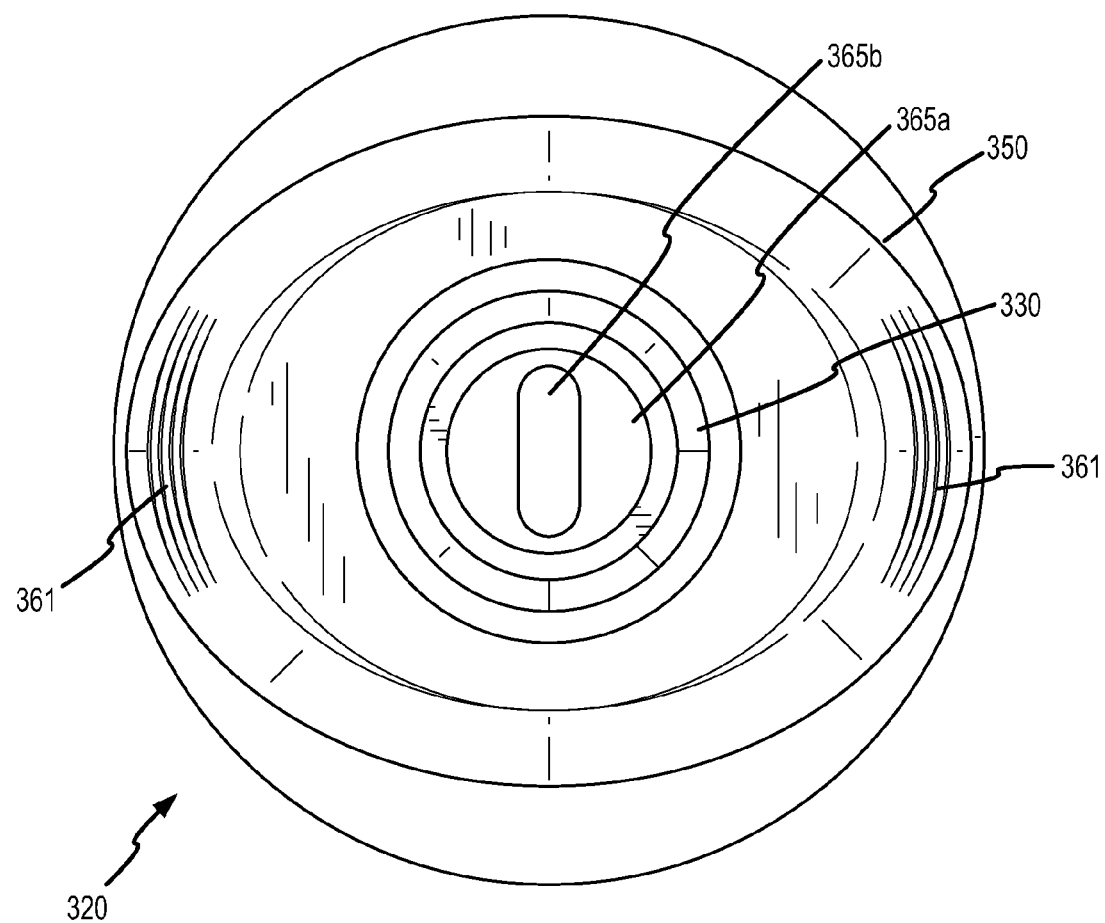
FIG. 25 is an end elevation of the coupling assembly in the same connected state depicted in FIG. 21 and as viewed from the female coupler end.

For a discussion of the second embodiment of the quick disconnect coupling assembly 310 of the present invention, reference is made to FIGS. 21-25. FIG. 21 is an isometric view of the quick disconnect coupling assembly 310, wherein the male coupler 315 and female coupler 320 are connected. FIG. 22 is a top plan of the coupling assembly 310 in the same connected state as depicted in FIG. 21. While a bottom plan of the coupling assembly 310 is not provided, it should be understood that it would appear identical to the view depicted in FIG. 22. FIG. 23 is a side elevation of the coupling assembly 310 in the same connected state depicted in FIG. 21. While a view of the opposite side of the coupling assembly 310 is not provided, it should be understood that it would appear identical to the view depicted in FIG. 23. FIG. 24 is an end elevation of the coupling assembly 310 in the same connected state depicted in FIG. 21 and as viewed from the male coupler end. FIG. 25 is an end elevation of the coupling assembly 310 in the same connected state depicted in FIG. 21 and as viewed from the female coupler end.

As shown in FIG. 21-23, the quick disconnect coupling assembly 310 includes a male coupler 315 and a female coupler 320. Each coupler 315, 320 includes a barbed end 325, 330 for insertion into, and connection with, a fluid conduit 335, 340 such as medical grade flexible tubing. Each coupler 315, 320 includes a housing or shroud 345, 350 that forms the exterior shell of each coupler 315, 320. When the couplers 315, 320 are connected, as depicted in FIGS. 21-23, the housings 345, 350 form a body that is semi-elliptical or egg-shaped as viewed from above, below or from the sides, as shown in FIGS. 22 and 23.

When the couplers 315, 320 are connected, the joining ends of the housings 345, 350 of the coupler 315, 320 abut along a seam 355 that circumferentially latitudinally extends about the exterior shell of the coupling assembly 310. The male coupling housing 345 includes a pair of buttons 346 that are pressed inward to disengage an engagement mechanism (shown in later figures) that holds the couplers 315, 320 together. A group of latitudinal extending slots 360 are located on each button 346 to provide friction contact points for a user's fingers when pressing on the button to disengage the engagement mechanism. Additional groups of latitudinal slots 361 are also located on the female housing 350 to facilitate a user's grasp of the female coupler 320 when longitudinally pulling the couplers 315, 320 apart after having disengaged the engagement mechanism.

As can be understood from FIGS. 21, 24 and 25, a fluid flow path 365 extends through the coupler assembly 310 from the male coupler barbed end 325 to the female coupler barbed end 330. In one embodiment, as indicated in FIGS. 24 and 25, and as will be described with greater detail later in this Detailed Description, the fluid flow path 365 makes the following transitions as it extends through the coupler assembly from the male barbed end 325 to the female barbed end 330: circular cross-section 365a to a rectangular cross-section 365b to a circular cross-section 365a to a rectangular cross-section to a circular cross-section 365a.

Figure 26:
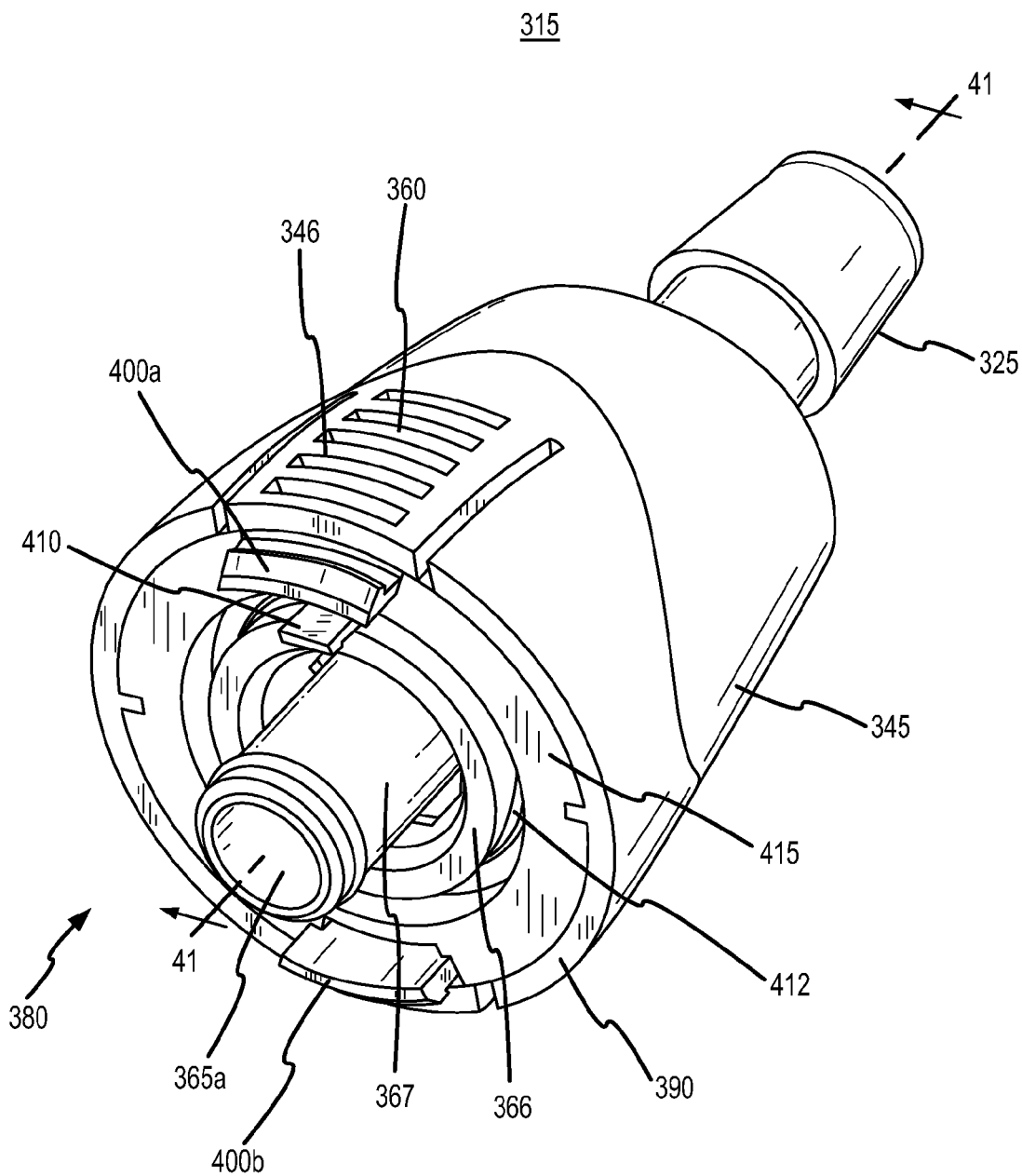
FIG. 26 is an isometric view of the male coupler as viewed from the joining side of the male coupler and indicating how a valve actuator of the male coupler would appear relative to a barrel of the male coupler when the male coupler is connected to the female coupler as illustrated in FIGS. 21-23.
Figure 27:
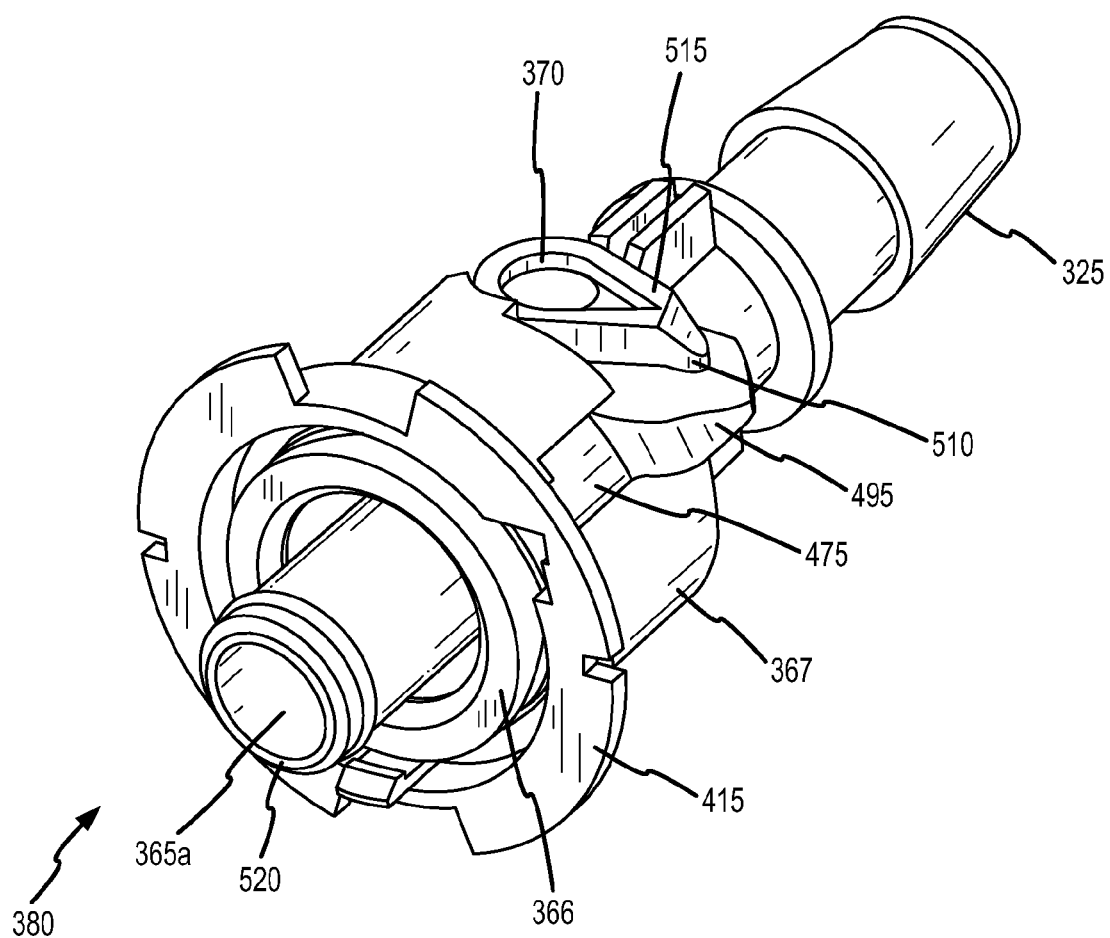
FIG. 27 is the same view of the male coupler depicted in FIG. 26, except the male coupler has been rotated about its longitudinal axis approximately 180 degrees to better depict its features and the male coupler housing has been removed from the male coupler to more fully reveal the male barrel.
Figure 28:
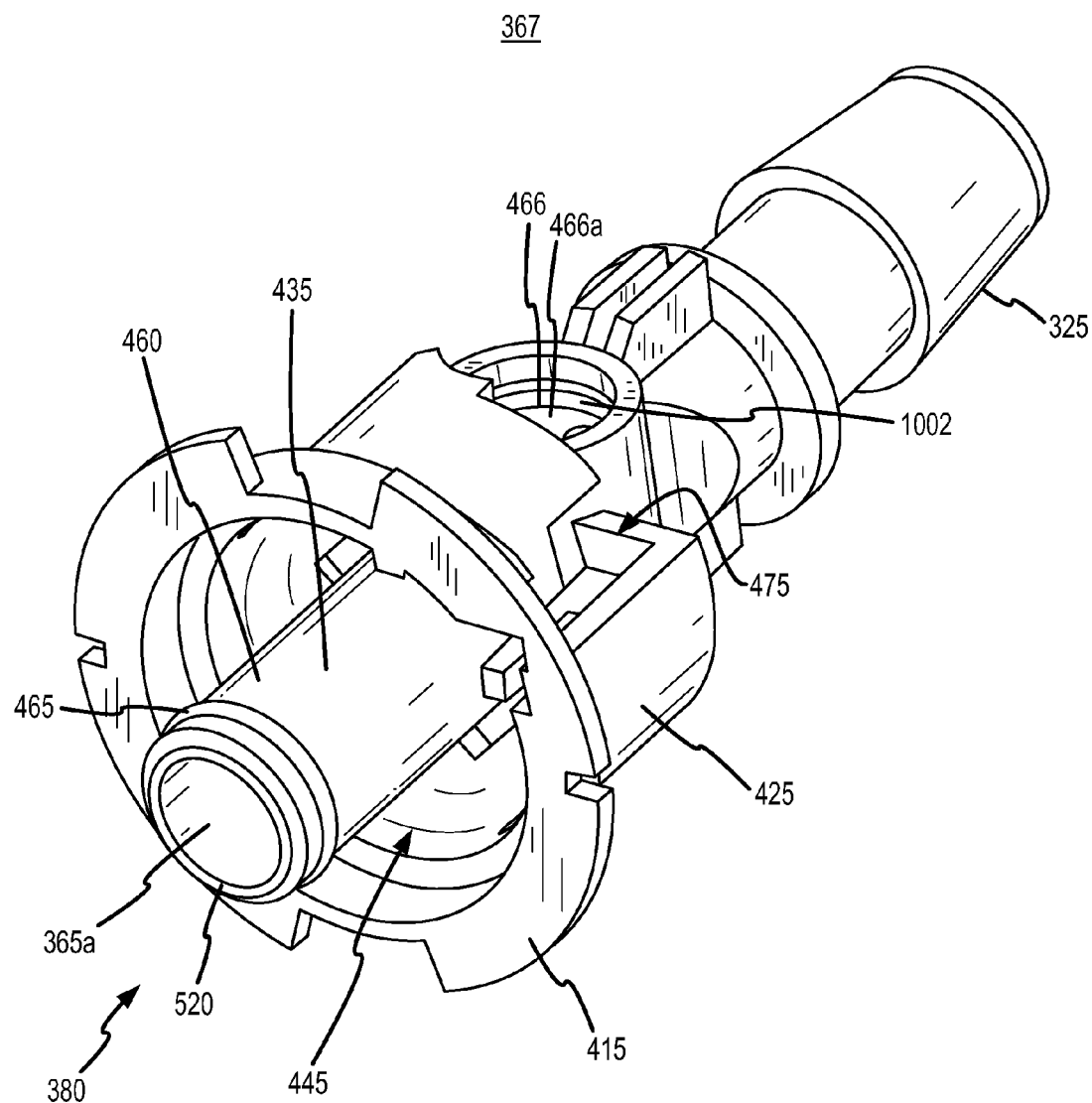
FIG. 28 is the same view of the male barrel depicted in FIG. 27, except the male valve actuator and the male valve have been removed from the male barrel to better illustrate its features.

For a detailed discussion of the elements of the male coupler 315 and female coupler 320, reference is made to FIGS. 26-33. FIG. 26 is an isometric view of the male coupler 315 as viewed from the joining side of the male coupler 315 and indicating how a valve actuator 366 of the male coupler 315 would appear relative to a barrel 367 of the male coupler 315 when the male coupler 315 is connected to the female coupler 320 as illustrated in FIGS. 21-23. FIG. 27 is the same view of the male coupler 315 depicted in FIG. 26, except the male coupler 315 has been rotated about its longitudinal axis approximately 180 degrees to better depict its features and the male coupler housing 345 has been removed from the male coupler 315 to more fully reveal the male barrel 367. FIG. 28 is the same view of the male barrel 367 depicted in FIG. 27, except the male valve actuator 366 and the male valve 370 have been removed from the male barrel 367 to better illustrate its features.

Figure 29:
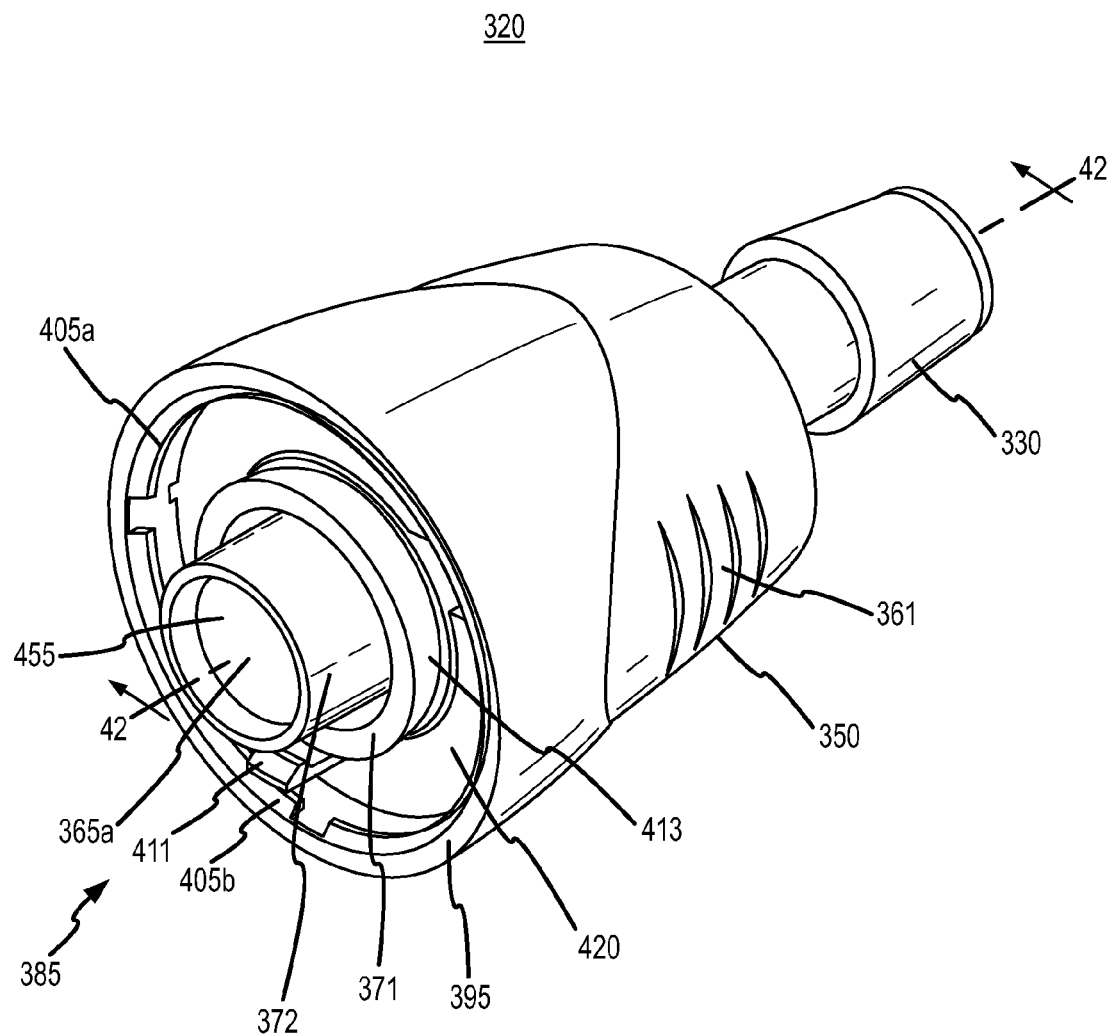
FIG. 29 is an isometric view of the female coupler as viewed from the joining side of the female coupler and indicating how a valve actuator of the female coupler would appear relative to a barrel of the female coupler when the female coupler is connected to the male coupler as illustrated in FIGS. 21-23.
Figure 30:
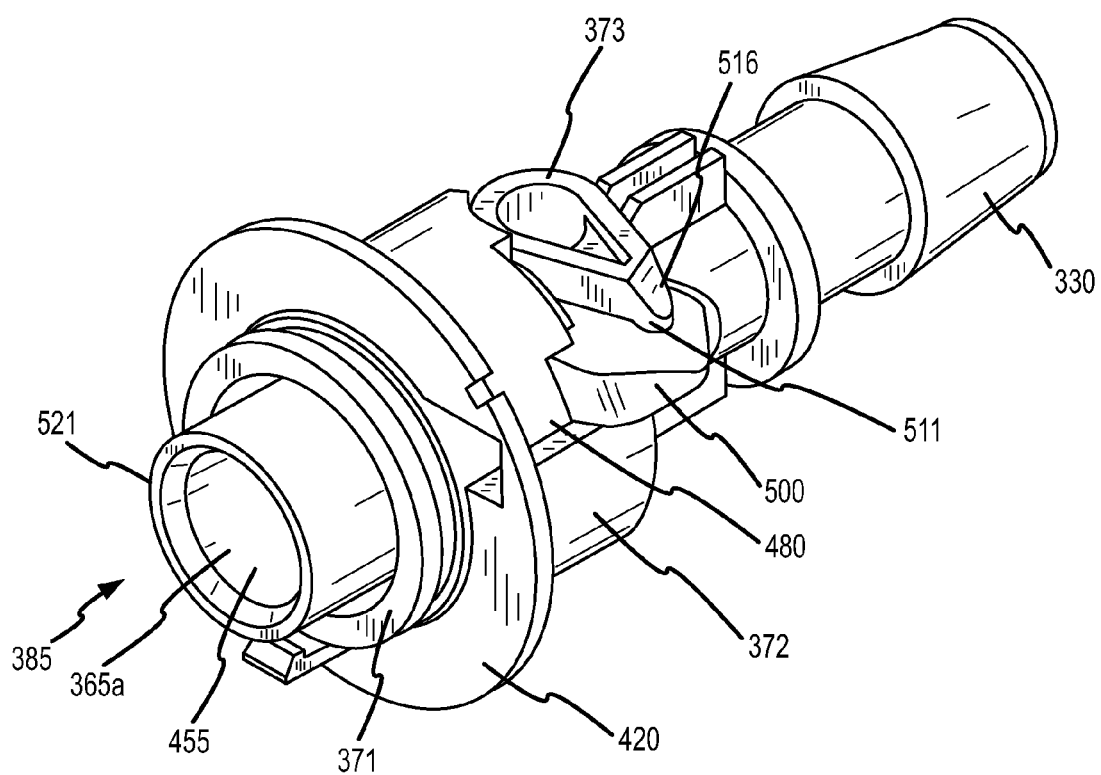
FIG. 30 is the same view of the female coupler depicted in FIG. 29, except the female coupler housing has been removed from the female coupler to more fully reveal the female barrel.
Figure 31:
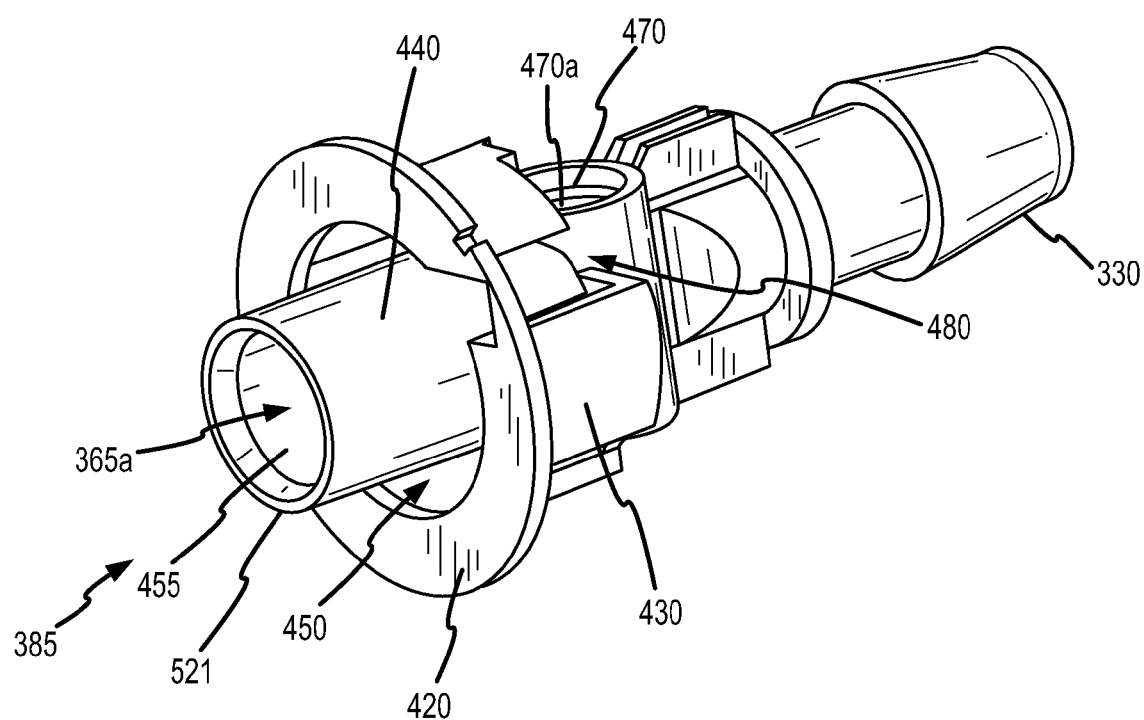
FIG. 31 is the same view of the female barrel depicted in FIG. 30, except the female valve actuator and the female valve have been removed from the female barrel to better illustrate its features.

FIG. 29 is an isometric view of the female coupler 320 as viewed from the joining side of the female coupler 320 and indicating how a valve actuator 371 of the female coupler 320 would appear relative to a barrel 372 of the female coupler 320 when the female coupler 320 is connected to the male coupler 315 as illustrated in FIGS. 21-23. FIG. 30 is the same view of the female coupler 320 depicted in FIG. 29, except the female coupler housing 350 has been removed from the female coupler 320 to more fully reveal the female barrel 372. FIG. 31 is the same view of the female barrel 372 depicted in FIG. 30, except the female valve actuator 371 and the female valve 373 have been removed from the female barrel 372 to better illustrate its features.

Figure 32:
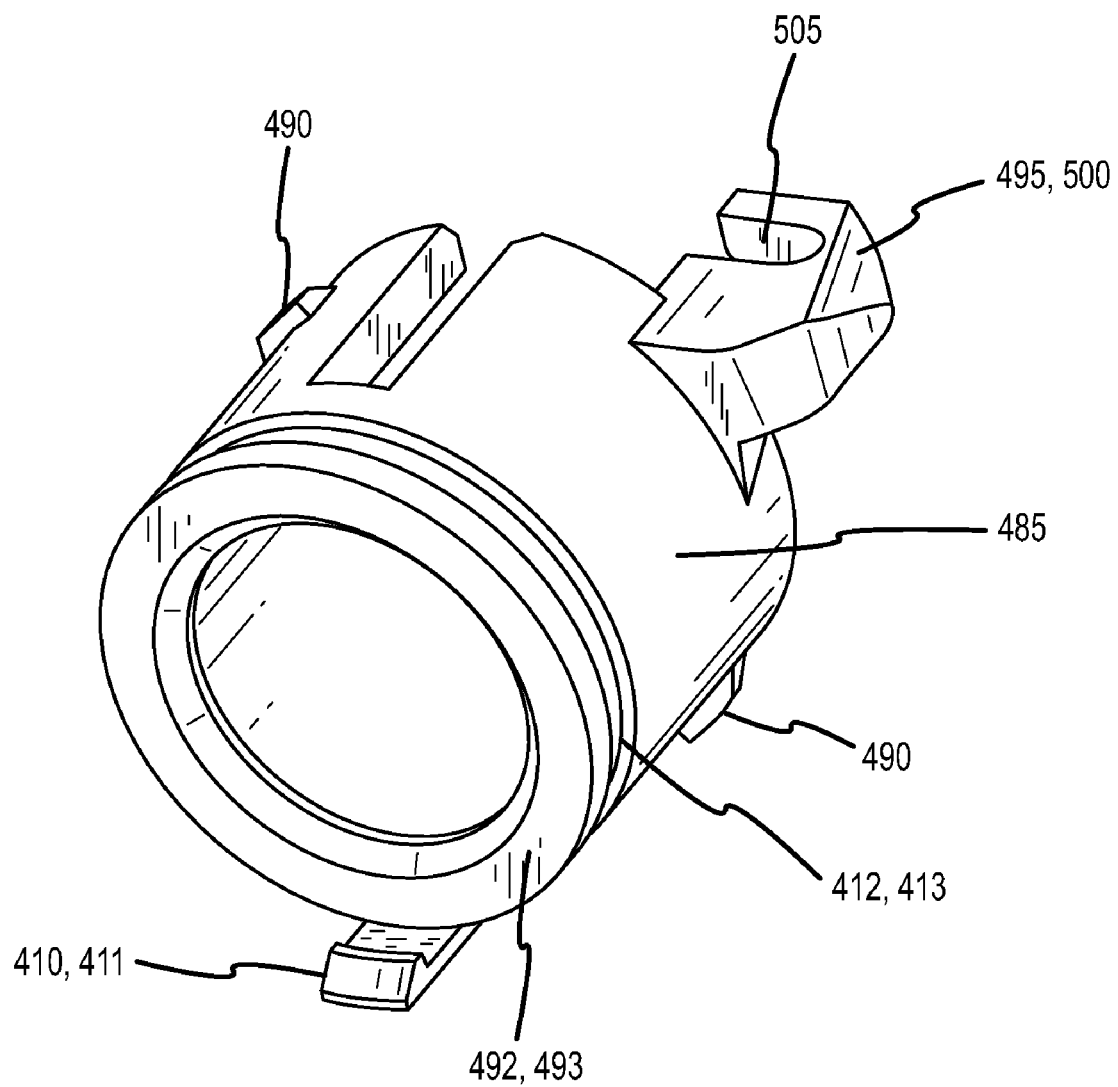
FIG. 32 is an isometric view of a valve actuator as employed in the male and female couplers.
Figure 32A:
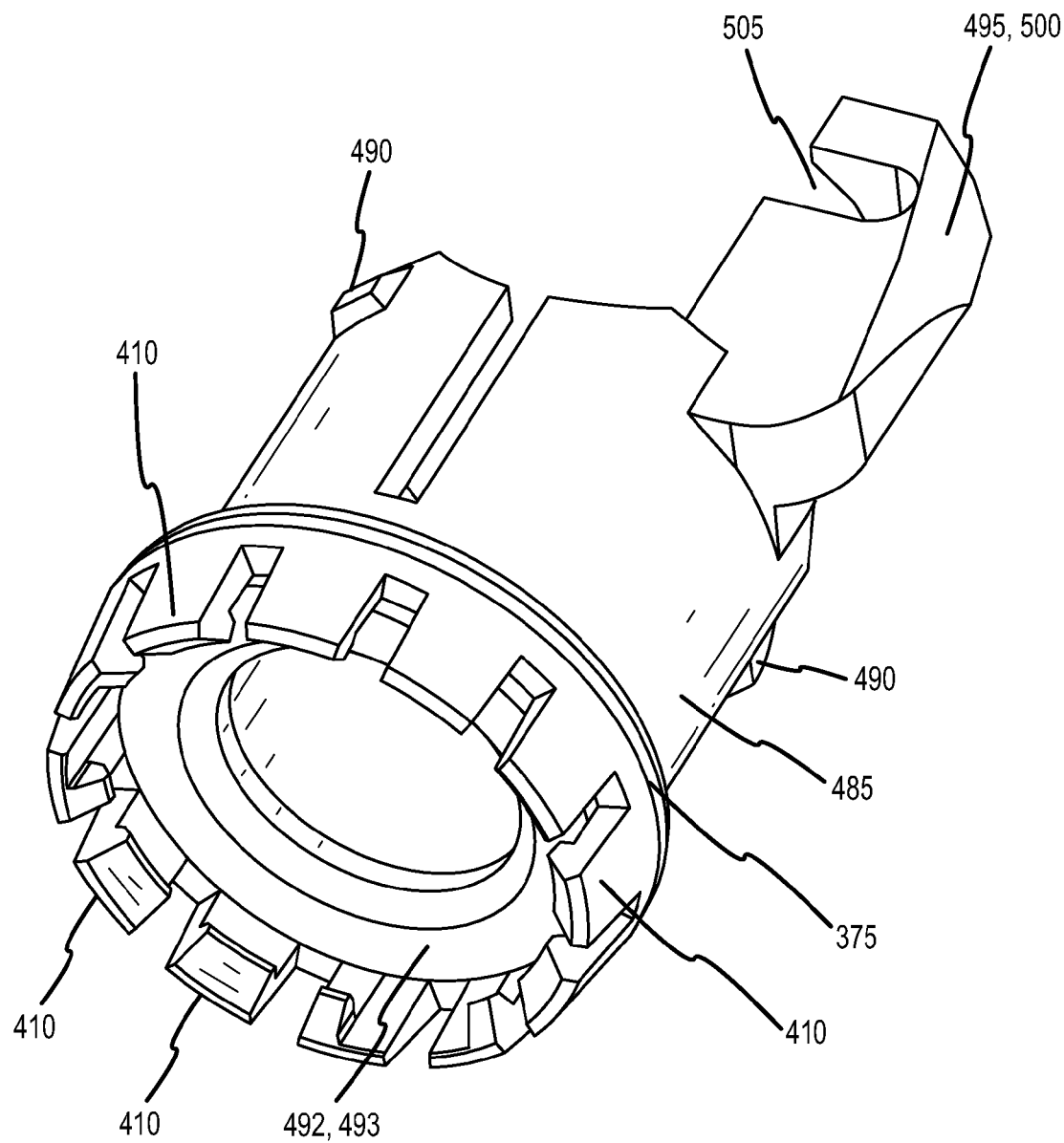
FIG. 32A is an isometric view of a second version of a valve actuator that is similar to the valve actuator depicted in FIG. 32, except the second version employs a latch ring with a plurality of latch fingers.
Figure 33:
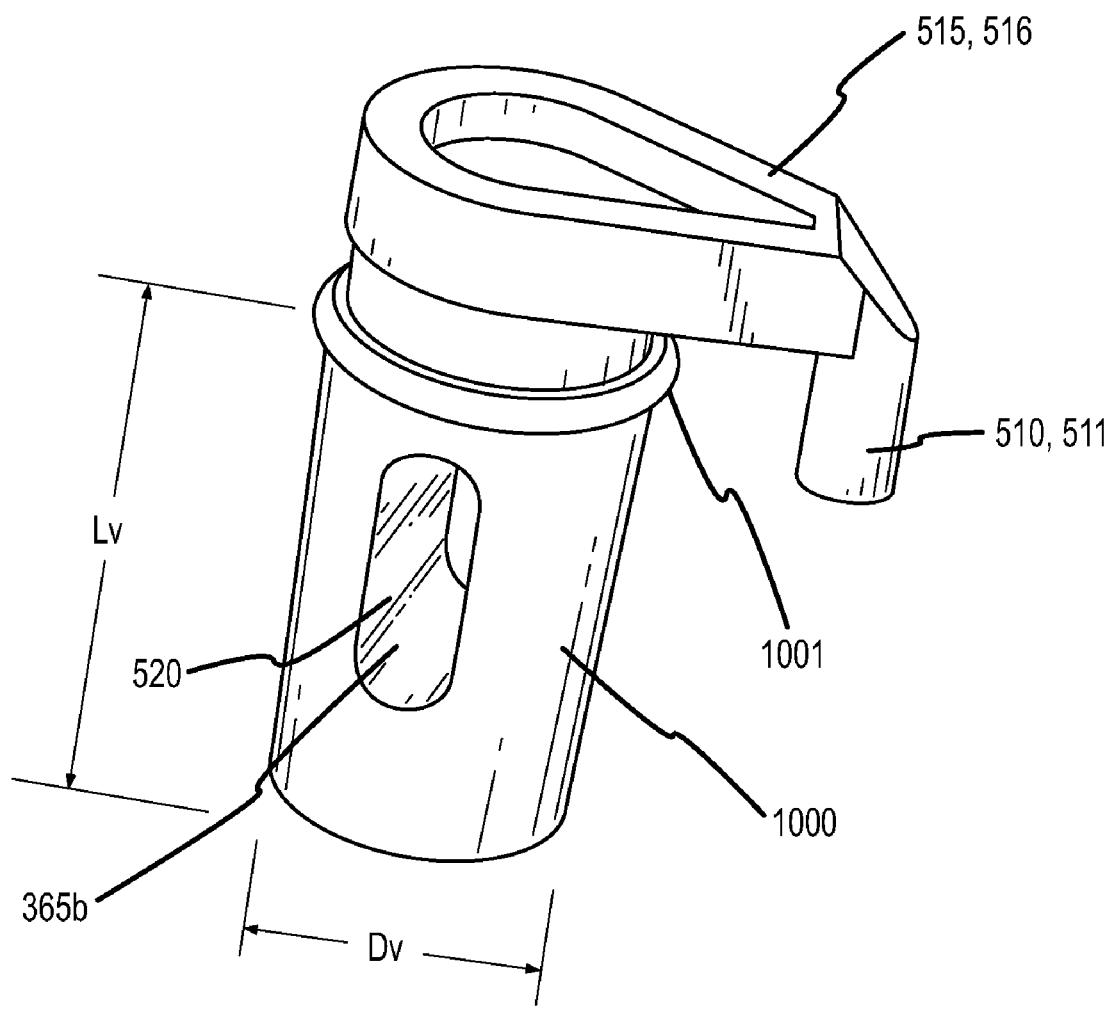
FIG. 33 is an isometric view of a valve as employed in the male and female couplers.

FIG. 32 is an isometric view of a valve actuator 366, 371 as employed in the male and female couplers 315, 320. FIG. 32A is an isometric view of a second version of a valve actuator 366, 371 that is similar to the valve actuator depicted in FIG. 32, except the second version employs a latch ring 375 with a plurality of latch fingers 410. FIG. 33 is an isometric view of a valve 370, 373 as employed in the male and female couplers 315, 320.

As shown in FIGS. 26 and 29, the male and female couplers 315, 320 each have joining ends 380, 385 that mate with, and couple to, the joining end 380, 385 of the other coupler 315, 320. Each joining end 380, 385 includes a seam face 390, 395 that forms a leading surface of each housing 345, 350. When the couplers 315, 320 are connected together, as illustrated in FIGS. 21-23, the seam faces 390, 395 abut to form the seam 355.

As illustrated in FIGS. 26 and 29, the male housing 345 includes upper and lower buttons 360 with engagement lips 400a, 400b that extend forwardly from the male housing 345 to engage with upper and lower engagement ridges or ring portions 405a, 405b formed in the inner surface of the female housing 350. As indicated in FIGS. 26, 29 and 32, in one version of the second embodiment, the leading end of each male and female valve actuator 366, 371 includes a latch finger 410, 411 that engages a groove 412, 413 that circumferentially extends about the outer circumferential surface of the leading tip of each barrel 366, 371. In another version of the second embodiment, as depicted in FIG. 32A, one of the valve actuators 366, 371 will have latch ring 375 with a plurality of latch fingers 410, and the other valve actuator 366, 371 will have a groove 413 for engagement by the plurality of latch fingers 410.

As will be discussed in greater detail later in this Detailed Description, when initially aligning the couplers 315, 320 in preparation for being connected to each other, but prior to pushing the joining ends 380, 385 together such that the housings 345, 350 engage each other, the latch fingers 410, 411 engage the grooves 412, 413. When the joining ends 380, 385 are then pushed together in order to cause the housings 345, 350 to engage such that the couplers 315, 320 fully engage, the lips 400 and ridges 405 engage to maintain the couplers 315, 320 in a connected state. The lips 400 and ridges 405 form the previously mentioned engagement mechanism. The lips 400 are disengaged from the ridges 405 by pressing inward on the buttons 360 and pulling the couplers 315, 320 longitudinally away from each other.

As indicated in FIGS. 28 and 31, the male and female couplers 315, 320 respectively include male and female barrels 367, 372 within the housings 345, 350. Each male and female barrel 367, 372 includes a faceplate 415, 420, an outer cylindrical wall 425, 430, a cylindrical neck 435, 440 coaxially centered within the cylindrical volume defined by the outer cylindrical wall 425, 430, and a cylindrical or ring shaped gap 445, 450 defined between the outer circumferential surface of the neck 435, 440 and the inner circumferential surface of the outer wall 425, 430.

Each neck 435, 440 protrudes forwardly relative to its respective faceplate 415, 420. The circular cross-sectioned fluid flow path 365a extends through the longitudinal center of each neck 435, 440. The fluid flow path 365a extends through the female neck 440 via a longitudinally extending orifice 455 that is sufficiently oversized to receive the outer circumferential surface 460 of the male neck 435 when the male neck 435 is plugged into the orifice 455 of the female neck 440. In one embodiment, the outer circumferential surface 460 of the male neck 435 and the orifice 455 of the female neck 440 are sufficiently close in size to form a fluid tight fit when the male neck 435 is plugged into the female neck 440. In one embodiment, an o-ring 465 extends in a groove about the outer circumferential surface 460 of the male neck 435 to provide a fluid tight fit when the male neck 435 is received within the orifice 455 of the female neck 440.

As shown in FIGS. 28 and 31, each barrel 367, 372 includes a barbed end 325, 330 on the end opposite from the joining ends 380, 385, a cylindrical opening or valve seat 466, 470 for receiving the valve 370, 373, and a longitudinally extending slot 475, 480 in the outer cylindrical wall 425, 430. The fluid flow path 365 extends through each barrel 367, 372 from the leading tip of each neck 435, 440 to the extreme tip of the barb end 325, 330.

As illustrated in FIG. 32, each valve actuator 366, 371 has a cylindrically shaped body 485, guides 490, a latch finger 410, 411, a groove 412, 413, a leading end face 492, 493, and an arm 495, 500. Alternatively, as depicted in FIG. 32A, one of the valve actuators 366, 371 will have a latch ring 375 with a plurality of latch fingers 410, and the other valve actuator 366, 371 will not have a latch ring 375 or latch fingers 410, 411, but will instead have only a groove 413 for engagement by the plurality of latch fingers 410 extending from the latch ring 375.

As shown in FIGS. 32 and 32A, each arm 495, 500 radially extends from the outer circumferential surface of the body 485 near the rear portion of the body 485. Each arm 495, 500 includes a slot or hole 505 that, as indicated in FIGS. 27 and 30, pivotally receives a pivot pin 510, 511 that extends from a lever arm 515, 516 of the valve 370, 373. As shown in FIGS. 28 and 31, the guides 490 radially extend from the outer circumferential surface of the body 485 to engage slots in the barrel 367, 372 to prevent the valve actuator 366, 371 from rotating within the barrel 367, 372.

As can be understood from FIGS. 27 and 30, the valve actuators 366, 371 are longitudinally displaceable about the necks 435, 440 of the barrels 367, 372 within the ring-like voids 445, 450 defined between the outer circumferential surfaces of the necks 435, 440 and the inner circumferential surfaces of the outer cylindrical walls 425, 430 of the barrels 367, 372. When the valve actuators 366, 371 longitudinally displace within the voids 445, 450, the arms 495, 500 displace within the longitudinally extending slots 475, 480 in the outer cylindrical walls 425, 430, which causes the valves 370, 373 to pivot within the valve seats 466, 470.

When the couplers 315, 320 are initially aligned for connection, the leading end faces 492, 493 are aligned and abutted against each other. At this time, each latch finger 410, 411 engages the groove 412, 413 of the other valve actuator 366, 371 to maintain the leading edge faces 482, 493 in alignment. When the couplers 315, 320 are then forced towards each other to cause the housings 345, 350 to become engaged via the coupling mechanism 400, 405, the valve actuators 366, 371 telescopically retreat against a biasing force about their respective necks 367, 372 into the ring-shaped voids 445, 450 in the barrels 367, 372. Each valve actuator 366, 371 is biased via a biasing mechanism (shown in later figures) towards the leading tip 520, 521 of each neck 435, 440. In one embodiment, the biasing mechanism is a helical spring (shown in later figures) extending about the outer circumferential surface of each neck 435, 440 between the neck 435, 440 and the inner circumferential surface of the valve actuator 367, 372.

As indicated in FIGS. 27 and 30, each barrel 367, 372 includes a valve 370, 373 that is located along the fluid flow path 365 between the back edge of the outer cylindrical wall 425, 430 and the barbed end 325, 330. As shown in FIG. 33, each valve 370, 373 has a cylindrical or barrel shaped body and includes a non-circular shaped orifice 520 that extends through the body of the valve 370, 373 perpendicular to the longitudinal axis of the body of the valve 370, 373. In one embodiment, the orifice 520 is rectangular and oriented such that its longitudinal axis coincides with the longitudinal axis of the body of the valve 370, 373. The orifice 520 serves as part of the rectangular cross-section fluid flow path 365b in each barrel 367, 372.

As shown in FIG. 33, each valve 370, 373 includes a lever arm 515, 516 that radially extends outward from the valve 370, 373. Each lever arm 515, 516 includes a pivot pin 510, 511 that extends downward from the lever arm 515, 516 generally parallel to the longitudinal axis of the body of the valve 370, 373. As indicated in FIGS. 27 and 30, each pivot pin 510, 511 is pivotally received in the slot or hole 505 (see FIG. 32) in the end of the arm 495, 500 of a valve actuator 366, 371.

As indicated in FIGS. 27, 28, 30 and 31, each barrel 367, 372 includes a cylindrical opening 466, 470 that receives therein the body of the valve 370, 373 and serves as a valve seat for the valve 370, 373. In a manner similar to that previously discussed regarding FIGS. 12 and 14 with respect to the first embodiment, the rectangular cross-section fluid flow path 365b penetrates each cylindrical opening 466, 470 to form a pair of rectangular openings 365b in the inner circumferential surface 466a, 470a of the cylindrical opening 466, 470. Each valve 370, 373 is pivotally displaceable about its longitudinal axis within its cylindrical opening or valve seat 466, 470 of a barrel 367, 372.

As can be understood from FIGS. 27 and 30, when the valve 370, 373 is pivotally displaced within the valve seat 466, 470 of a barrel 367, 372 such that the valve's lever arm 495, 500 is displaced away from the faceplate 415, 420 of the barrel 367, 372, the rectangular orifice 520 extending through each valve 370, 373 aligns with the rectangular openings 365b in the inner circumferential surface 466a, 470a of the valve seat 466, 470. As a result, the fluid flow path 365 extends uninterrupted through the barrel 367, 372 from the extreme end of the barbed end 320, 330 to the leading tip 520, 521 of the neck 435, 440. Conversely, when the valve 370, 373 is pivotally displaced within the valve seat 466, 470 of a barrel 367, 372 such that the valve's lever arm 495, 500 is displaced towards the faceplate 415, 420 of the barrel 367, 372, the rectangular orifice 520 extending through each valve 370, 373 does not coincide to any extent with the rectangular openings 365b in the inner circumferential surface 466a, 470a of the valve seat 466, 470. As a result, the fluid flow path 365 is sealed off or interrupted at the location of the valve 370, 373.

Figure 34:
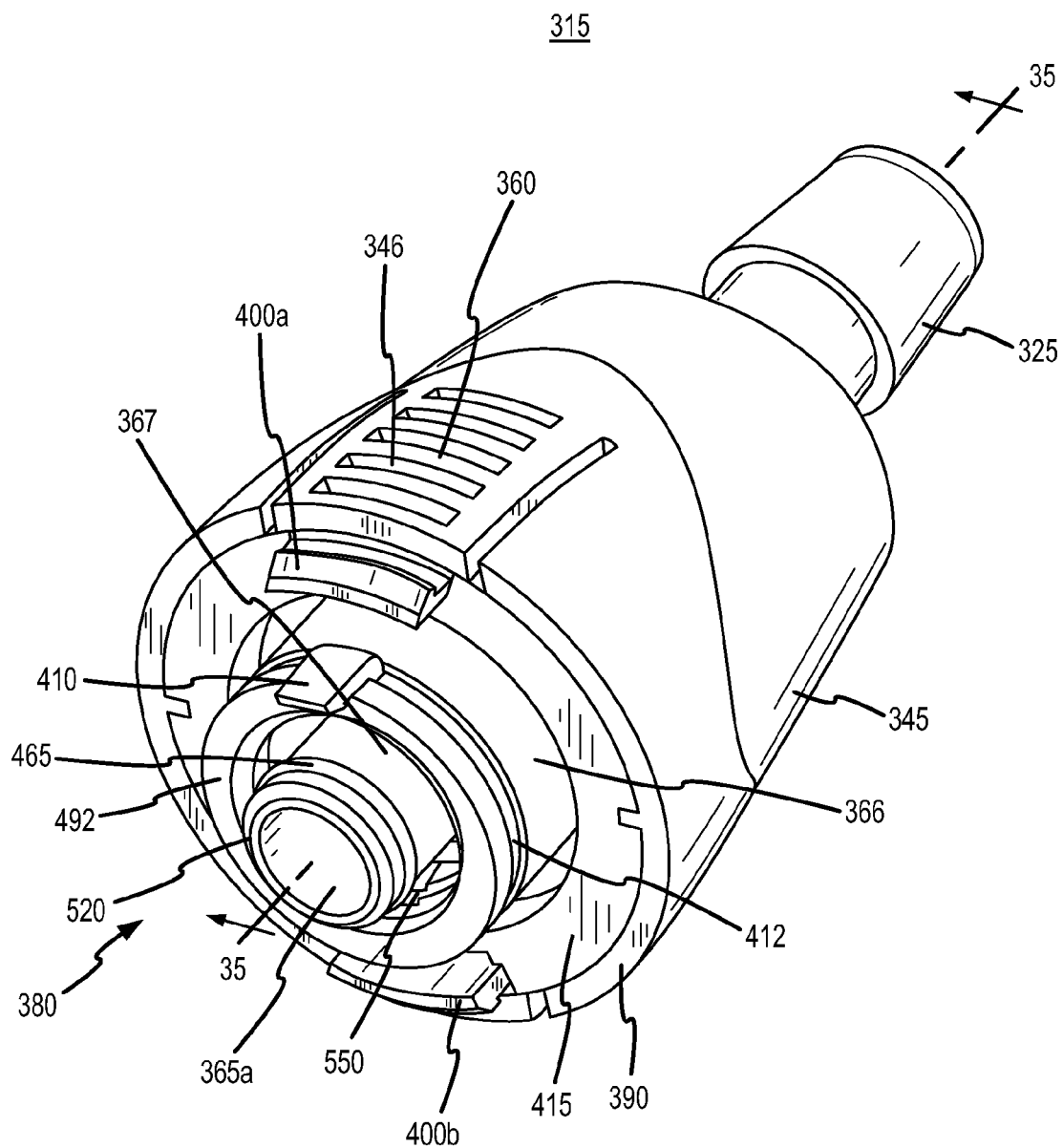
FIG. 34 is an isometric view of the male coupler as viewed from the joining side of the male coupler and indicating how a valve actuator of the male coupler would appear relative to a barrel of the male coupler when the male coupler is not connected to the female coupler.
Figure 35:
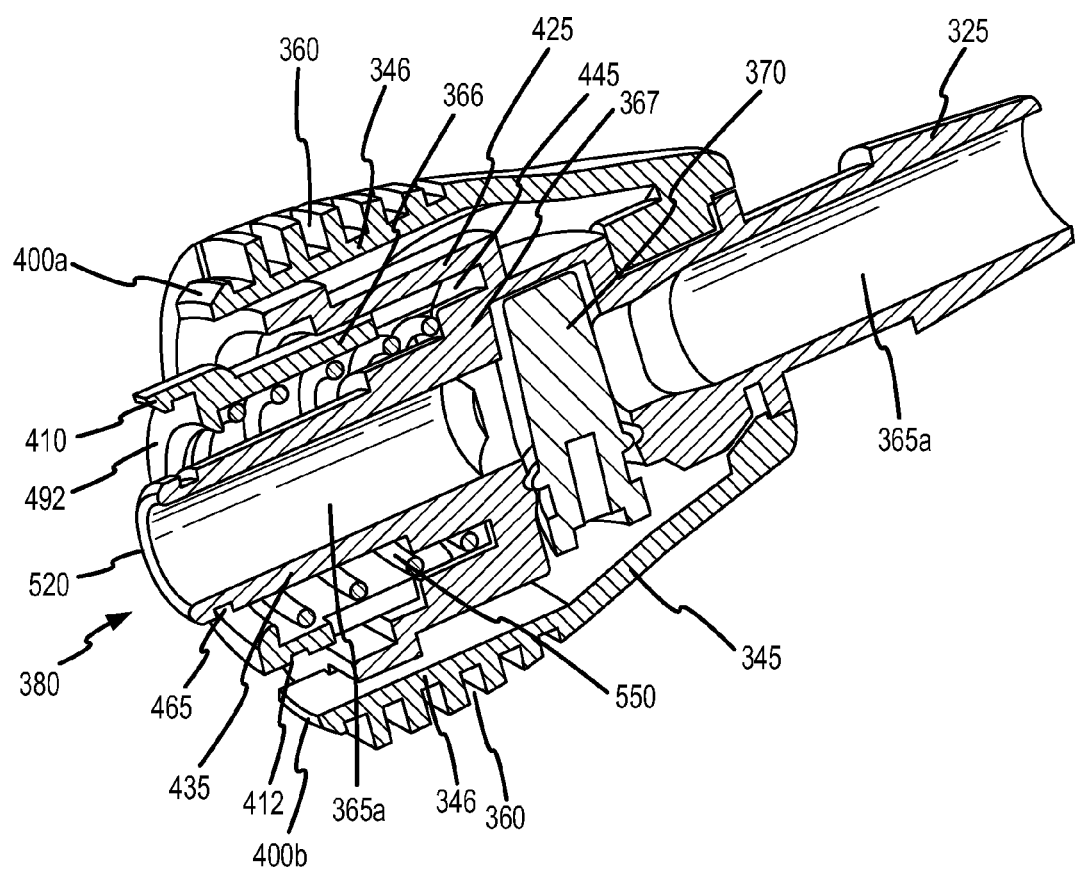
FIG. 35 is an isometric cross-sectional view of the male coupler as taken along section line 35-35 in FIG. 34.
Figure 36:
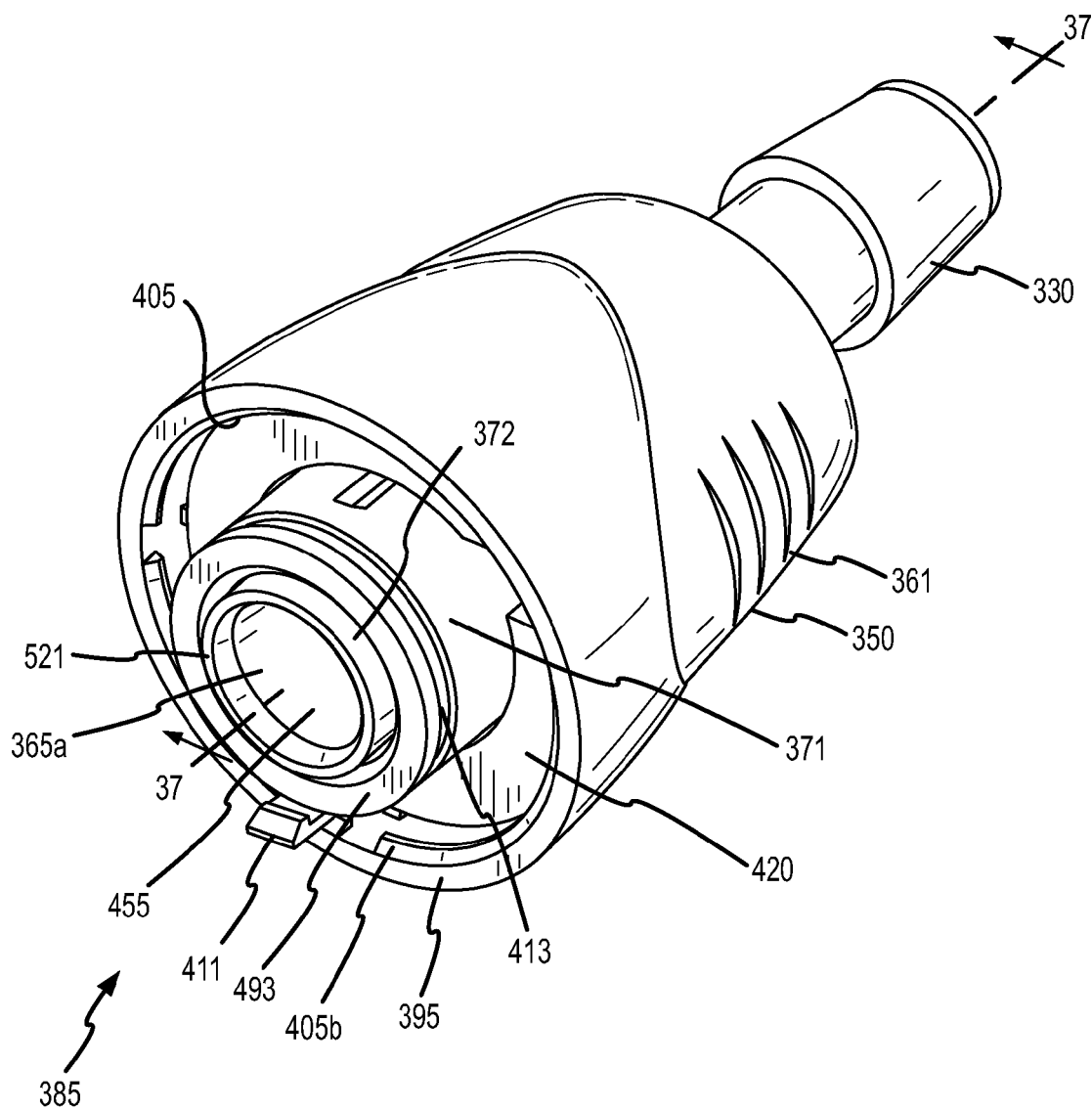
FIG. 36 is an isometric view of the female coupler as viewed from the joining side of the female coupler and indicating how a valve actuator of the female coupler would appear relative to a barrel of the female coupler when the female coupler is not connected to the male coupler.
Figure 37:
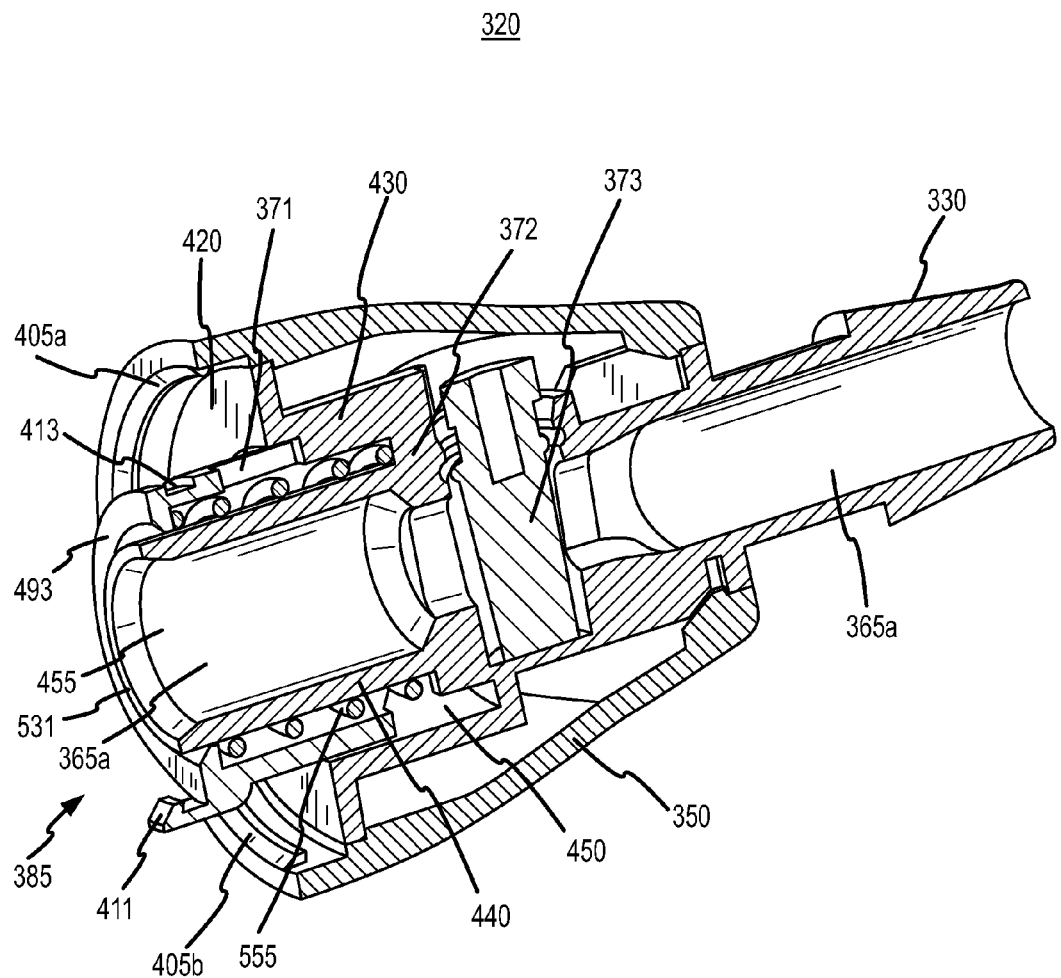
FIG. 37 is an isometric cross-sectional view of the female coupler as taken along section line 37-37 in FIG. 36.
Figure 38:
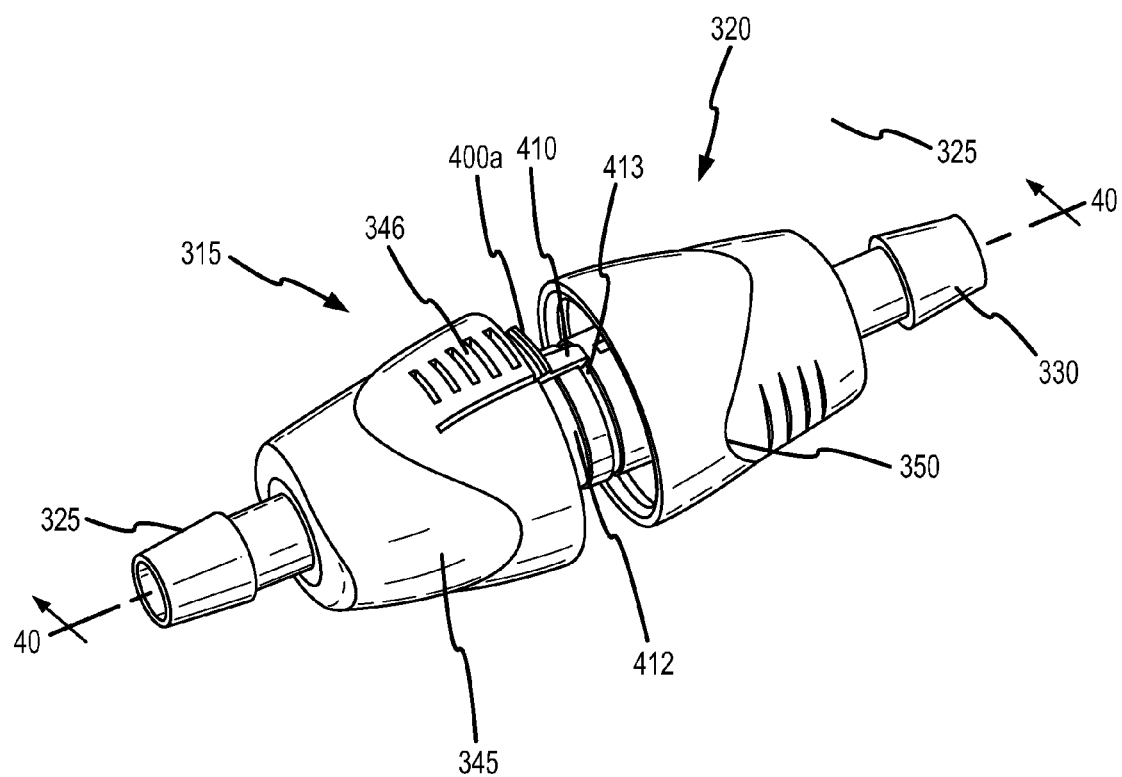
FIG. 38 is an isometric view of the male coupler being aligned for engagement with the female coupler, wherein the leading end faces of the valve actuators have abutted and the latch fingers have engaged the grooves on the valve actuators to maintain the valve actuators in an abutting alignment.
Figure 38A:
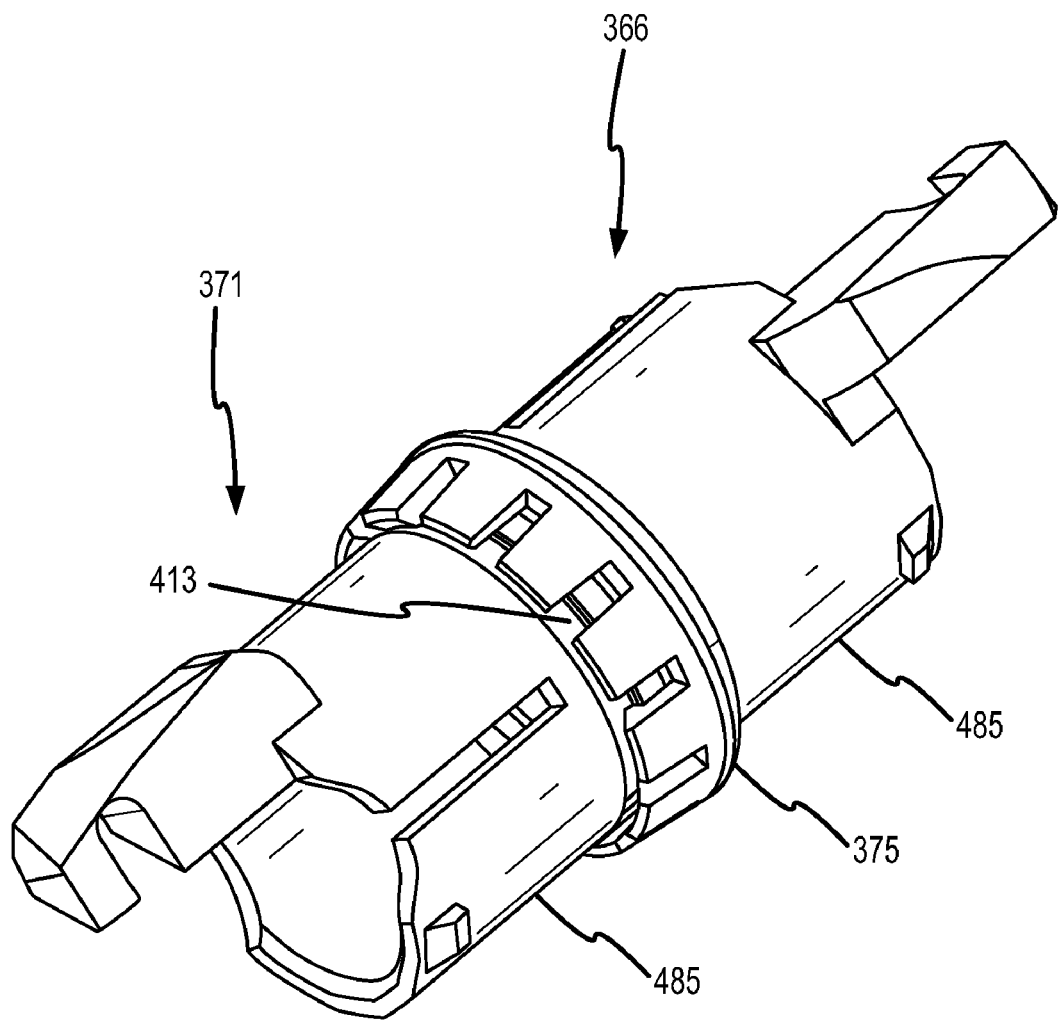
FIG. 38A is similar to FIG. 38, except only the valve actuators are illustrated and the valve actuator depicted in FIG. 32A is employed such that the plurality of latch fingers of a latch ring have engaged the groove of the opposing actuator when the actuators are in abutting contact.
Figure 39:
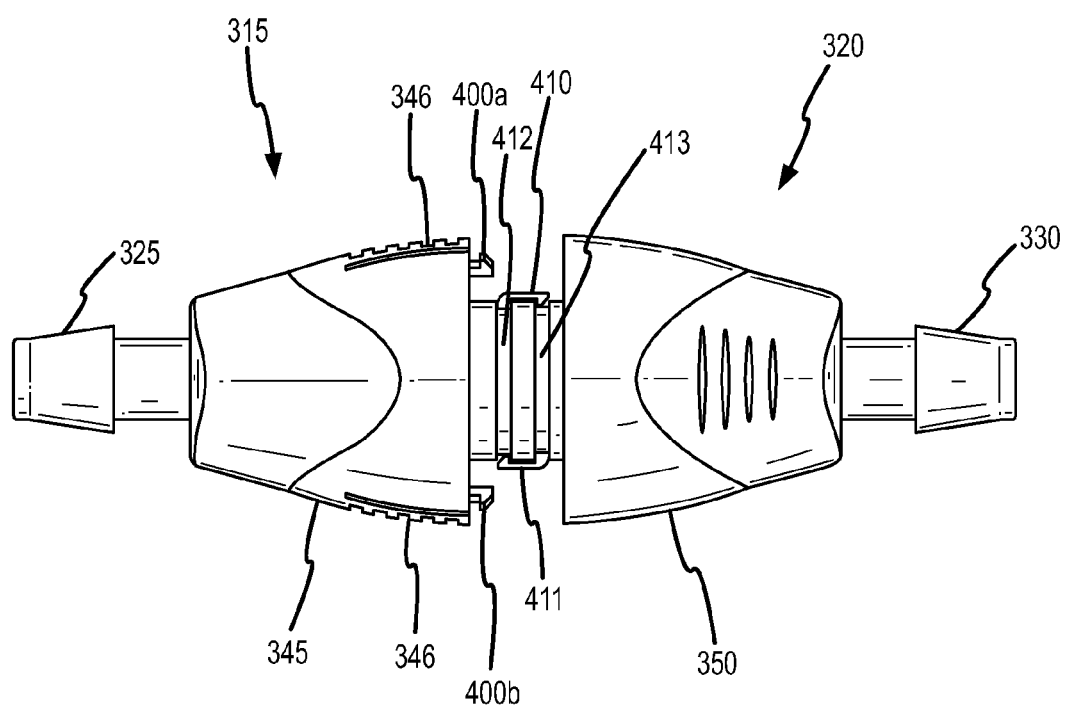
FIG. 39 is a side elevation of the male and female couplers as depicted in FIG. 38.
Figure 40:
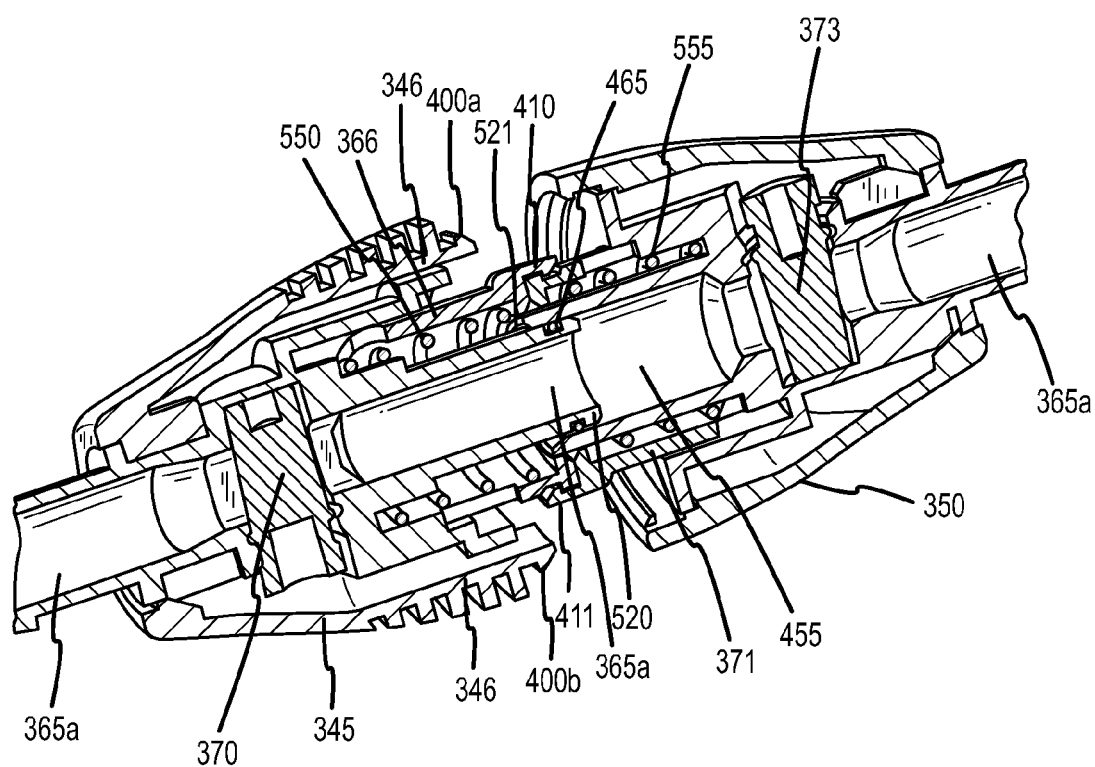
FIG. 40 is an isometric cross-sectional view of the male and female couplers as taken along section line 40-40 in FIG. 38.
Figure 41:
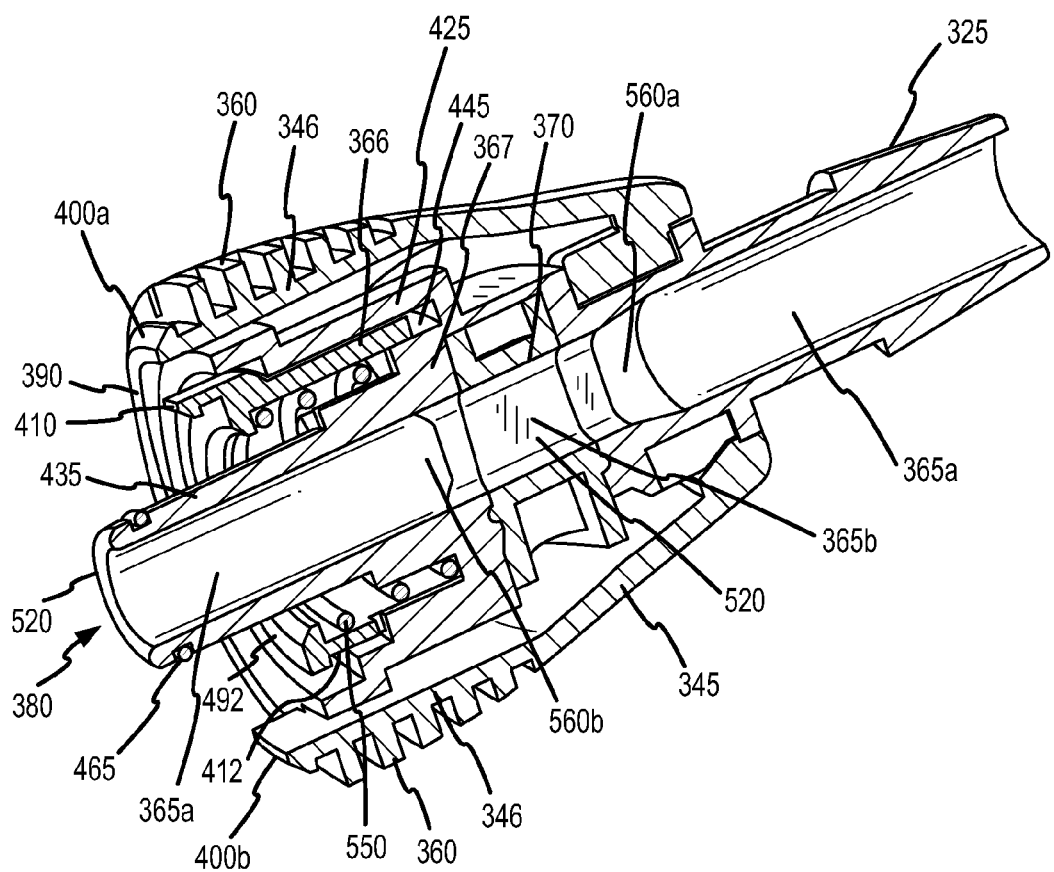
FIG. 41 is an isometric cross-sectional view of the male coupler as taken along section line 41-41 in FIG. 26.
Figure 42:
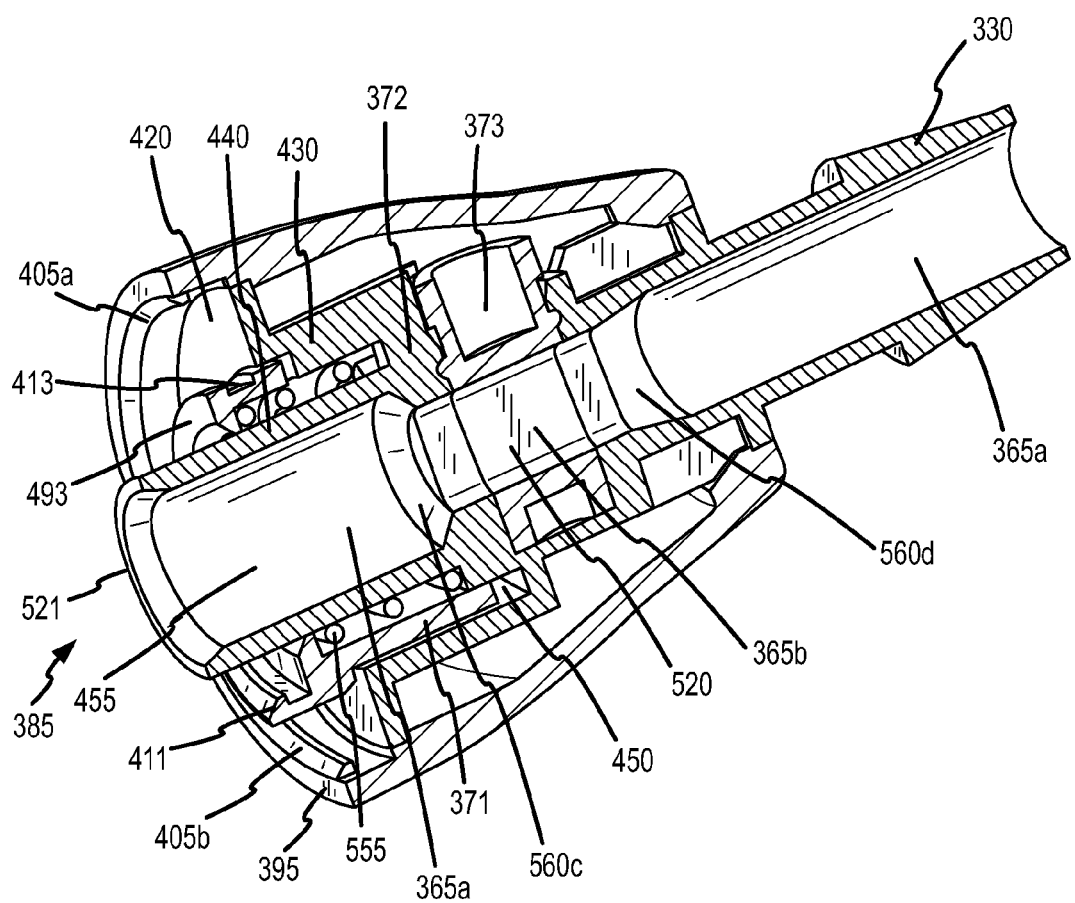
FIG. 42 is an isometric cross-sectional view of the female coupler as taken along section line 42-42 in FIG. 29.
Figure 43:
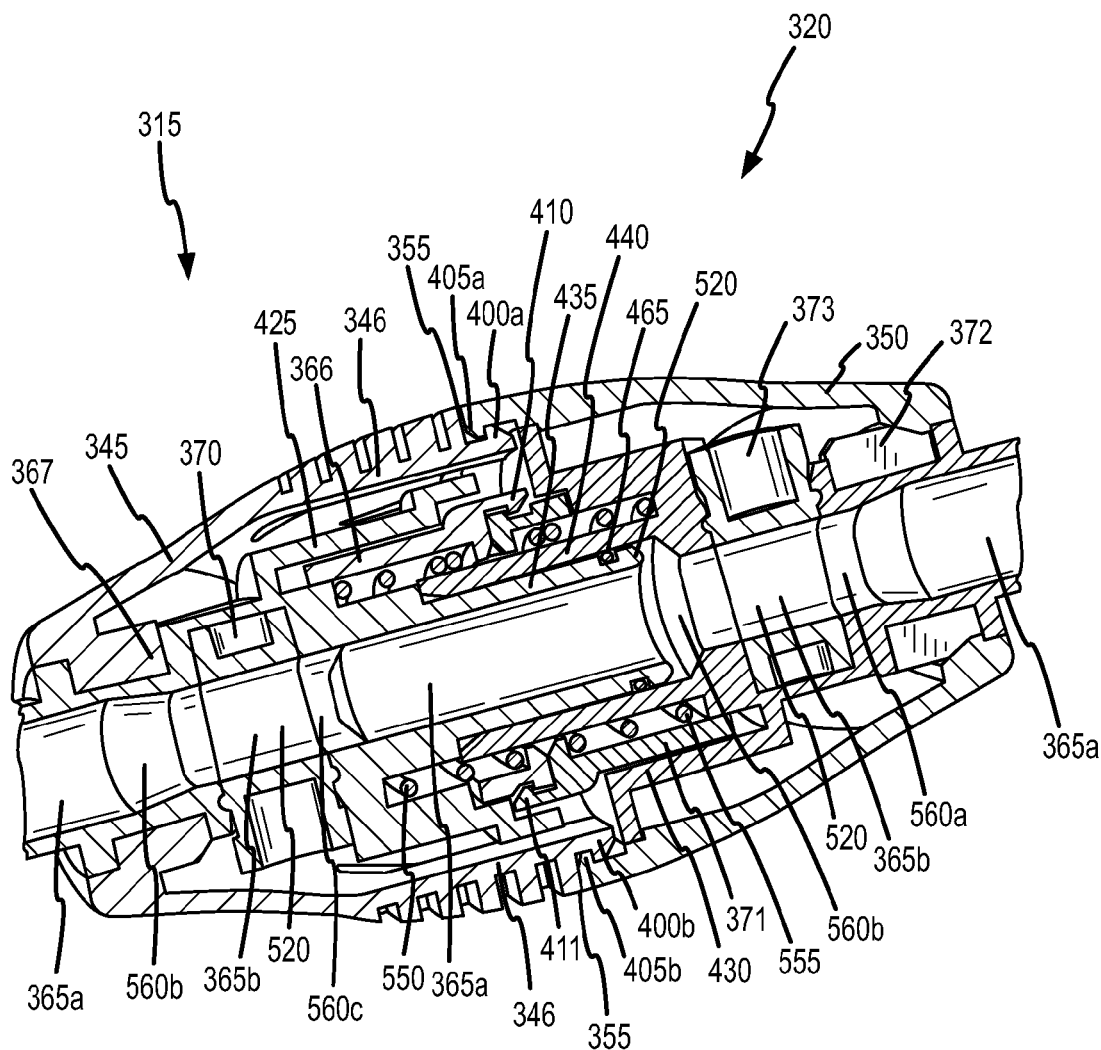
FIG. 43 is an isometric cross-sectional view of the male and female couplers as taken along section line 43-43 in FIG. 21.

For a better understanding of the interaction of the various components of the quick disconnect coupling assembly 310 when the male and female couplers 315, 320 are connected as illustrated in FIGS. 21-23, reference is made to FIGS. 21-23, 26, 27, 29, 30, and 34-43. FIG. 34 is an isometric view of the male coupler 315 as viewed from the joining side of the male coupler 315 and indicating how a valve actuator 366 of the male coupler 315 would appear relative to a barrel 367 of the male coupler 315 when the male coupler 315 is not connected to the female coupler 320. FIG. 35 is an isometric cross-sectional view of the male coupler 315 as taken along section line 35-35 in FIG. 34. FIG. 36 is an isometric view of the female coupler 320 as viewed from the joining side of the female coupler 320 and indicating how a valve actuator 371 of the female coupler 320 would appear relative to a barrel 372 of the female coupler 320 when the female coupler 320 is not connected to the male coupler 315. FIG. 37 is an isometric cross-sectional view of the female coupler 320 as taken along section line 37-37 in FIG. 36. FIG. 38 is an isometric view of the male coupler 315 being aligned for engagement with the female coupler 320, wherein the leading end faces 492, 493 of the valve actuators 366, 371 have abutted and the latch fingers 410, 411 have engaged the grooves 412, 413 on the valve actuators 366, 371 to maintain the valve actuators 366, 377 in an abutting alignment. FIG. 38A is similar to FIG. 38, except only the valve actuators 366, 371 are illustrated and the valve actuator depicted in FIG. 32A is employed such that the plurality of latch fingers 410 of a latch ring 375 have engaged the groove 413 of the opposing actuator 371 when the actuators 366, 371 are in abutting contact. FIG. 39 is a side elevation of the male and female couplers 315, 320 as depicted in FIG. 38. FIG. 40 is an isometric cross-sectional view of the male and female couplers 315, 320 as taken along section line 40-40 in FIG. 38. FIG. 41 is an isometric cross-sectional view of the male coupler 315 as taken along section line 41-41 in FIG. 26. FIG. 42 is an isometric cross-sectional view of the female coupler 320 as taken along section line 42-42 in FIG. 29. FIG. 43 is an isometric cross-sectional view of the male and female couplers 315, 320 as taken along section line 43-43 in FIG. 21.

As shown in FIGS. 34-37, when the male and female couplers 315, 320 are disconnected from each other, their respective valve actuators 366, 371 are biased by a biasing mechanism (e.g., a helical spring 550, 555) towards the leading tip 520, 521 of each neck 435, 440. As can be understood from FIGS. 27 and 30 and as indicated in FIGS. 35 and 37, because the valve actuators 366, 371 are biased in a position near the leading tips 520, 521 when the male and female couplers 315, 320 are not connected to each other, the valve actuator arms 495, 500 are positioned in the longitudinally extending barrel slots 475, 480 near the barrel faceplates 415, 420. As a result, the valves 370, 373 are caused to pivot within the valve seats 466, 470 via the linkage between the valve actuator arms 495, 500 and the valve lever arms 515, 516 such that the valve orifices 520 do not coincide with any part of the fluid flow path 365. Accordingly, the fluid flow path 365 is sealed at each valve 370, 373.

In aligning the couplers 315, 320 to facilitate their engagement, as depicted in FIGS. 21-23, the couplers 315, 320 are brought together such that the leading end faces 492, 493 of the valve actuators 366, 371 abut as shown in FIGS. 38-40 and 38A. When bringing the leading end faces 492, 493 into abutment, the latch fingers 410, 411 serve as guides to assist in achieving proper alignment between the couplers 315, 320. Also, when the leading end faces 492, 493 abut against each other, the latch fingers 410, 411 engage the grooves 412, 413 on the valve actuators 366, 371 to maintain the valve actuators 366, 377 in proper abutting alignment.

As indicated in FIG. 40, when the leading end faces 492, 493 of the valve actuators 366, 371 are in proper abutting alignment, the leading tip 520 of the male neck 435 is received in the orifice 455 of the leading tip 521 of the female neck 440. However, the valves 370, 373 remain pivoted in the closed positions because the valve actuators 366, 371 have not been caused to telescopically retreat against their respective biasing forces. The o-ring 465 provides a seal between the outer circumferential surface of the male neck 435 and the circumferential surface of the orifice 455.

After being properly abuttingly aligned as depicted in FIGS. 38-40 and 38A, the couplers 315, 320 can be fully engaged, as depicted in FIGS. 21-23 and 43, by pressing the couplers 315, 320 together with sufficient force to overcome the biasing force provided by the helical springs 550, 555 of the respective couplers 315, 320. In doing so, the valve actuators 366, 371 are caused to telescopically displace about the necks 435, 440 as the valve actuators 366, 371 retreat into the ring-like voids 445, 450 defined between the outer circumferential surfaces of the necks 435, 440 and the inner circumferential surfaces of the outer cylindrical walls 425, 430 of the barrels 367, 372.

As can be understood from FIGS. 27 and 30 and as indicated in FIGS. 41-43, because the valve actuators 366, 371 are forced away from the leading tips 520, 521 and well into the ring-like voids 445, 450 when the male and female couplers 315, 320 are connected to each other, the valve actuator arms 495, 500 are positioned in the longitudinally extending barrel slots 475, 480 near the valve seats 466, 470. As a result, the valves 370, 373 are caused to pivot within the valve seats 466, 470 via the linkage between the valve actuator arms 495, 500 and the valve lever arms 515, 516 such that the valve orifices 520 fully coincide with the fluid flow path 365. Accordingly, the fluid flow path 365 extends uninterrupted through the entire coupling assembly 10, including through each valve 370, 373.

As shown in FIG. 43, when the couplers 315, 320 are fully engaged, the engagement lips 400a, 400b of the male housing 345 attach to the ring portions 405a, 405b of the female housing 350 such that the seam face 390 (see FIG. 41) of the male housing 345 abuts against the seam face 395 (see FIG. 42) of the female housing 350 to form the seam 355 (see FIGS. 21-23). Also, as indicated in FIG. 43, when the couplers 315, 320 are fully engaged, the male neck 435 is fully inserted into the orifice 455 of the female neck 440.

As illustrated in FIGS. 41-43, the fluid flow path 365 has four transition points 560 where the fluid flow path 365 changes between circular and rectangular cross-sections. Following the fluid flow path 365 from the male barb end 325 towards the female barb end 330, the fluid flow path 365 begins as a circular cross-section fluid flow path 365a and transitions at a first transition point 560a to a rectangular cross-section fluid flow path 365b just prior to reaching the male valve 370. Shortly after passing through the male valve 370, the rectangular cross-section fluid flow path 365b transitions at a second transition point 560b to a circular cross-section fluid flow path 365a, which continues through the male neck 435. Shortly before reaching the female valve 373, the circular cross-section fluid flow path 365a transitions at a third transition point 560c to a rectangular cross-section fluid flow path 365b. Shortly after passing through the female valve 373, the rectangular cross-section fluid flow path 365b transitions at a fourth transition point 560d to a circular cross-section fluid flow path 365a, which continues to the female barbed end 330.

As can be understood from FIG. 33, transitioning from a circular to a rectangular cross-section fluid flow path 365 prior to passing through the orifice 520 of the valves 370, 373 allows the use of small diameter valve bodies and seats without having to settle for valve orifices 520 that have small fluid flow path cross-sections. As a result of using the generally rectangular valve orifices 520, the couplers 315, 320 of the present invention can have relatively thin housings 345, 350 without having valves 370, 373 with significant fluid flow constrictions that result in large pressure drops, as typically found in the art.

The couplers 315, 320 are disengaged from each other by first pressing inward the buttons 346 on the male housing 345 to cause the engagement lips 400a, 400b to detach from the ring portions 405a, 405b of the female housing 350. The couplers 315, 320 are then pulled longitudinally away from each other while continuing to press inward on the buttons 346. As the couplers 315, 320 are withdrawn from each other, the valve actuators 366, 371 are allowed to bias back towards the leading tip 520, 521 of the necks 435, 440, thereby causing the valves 370, 373 to pivot back to the closed position depicted in FIGS. 35, 37 and 40.

As can be understood from a review of FIGS. 11-16, 28, 31, 33, 35, 37 and 41-43, in one embodiment, the cylindrical or barrel shaped bodies of the valves 170, 175, 370, 373 are conically shaped such that they taper slightly when traveling along the longitudinal axis of the valve body away from the lever arm end. The conically shaped bodies of the valves are received in conically shaped cylindrical openings 235, 240, 466, 470 in the barrels 66, 67, 367, 372. The conically shaped cylindrical openings taper in a manner similar to the conically shaped cylindrical bodies of the valves.

For each of the disclosed embodiments of the fluid coupling assembly 10, 310, the various parts comprising the fluid coupling assembly are formed from polymer materials. In one embodiment, the housings 15, 20, 315, 320 are made from copolyester, nylon, CYROLITE®, or other similar polymers. In one embodiment, the actuators 366, 371 are made from copolyester, polycarbonate, polycarbonate blend, or other similar polymers. In one embodiment, the barrels 66, 67, 367, 372, including their cylindrical openings 235, 240, 466, 470, are formed from generally rigid types of polymer materials (e.g., hard polycarbonates, Teflon® impregnated polycarbonates, nylon 66, high density polyethylene ("HDPE"), etc.), and the cylindrical or barrel shaped bodies of the valves 170, 175, 370, 373 are formed from less rigid polymer materials (e.g., Delrin®, polyethylene, nylon 66, etc.).

In one embodiment, the barrels 66, 67, 367, 372 will be formed from a polymer material (e.g., hard polycarbonates, Teflon® impregnated polycarbonates, nylon 66, etc.) having a durometer range of approximately 118 to approximately 122 Rockwell R Scale, and the cylindrical or barrel shaped bodies of the valves 170, 175, 370, 373 will be formed from a polymer material (e.g., Delrin®, polyethylene, nylon 66, acetale, etc.) having a durometer range of approximately 107 to approximately 120 Rockwell R Scale.

In one embodiment, the barrels 66, 67, 367, 372 will be formed from a polymer material (e.g., hard polycarbonates, Teflon® impregnated polycarbonates, nylon 66, etc.) having a durometer range of approximately 118 to approximately 122 Rockwell R Scale, and the cylindrical or barrel shaped bodies of the valves 170, 175, 370, 373 will be formed from a polymer material (e.g., HDPE, nylon 66, Kynar®, etc.) having a durometer range of approximately 60 to approximately 65 Rockwell R Scale.

In one exemplary embodiment, where the diameter D, of the cylindrical body of the valve 170, 175, 370, 373 (see FIGS. 15 and 33) ranges between approximately 0.2 inch and approximately 0.5 inch and the length $L_v$ of the cylindrical body 1000 ranges between approximately 0.5 inch to 1.0 inch, a hard polycarbonate cylindrical opening 235, 240, 466, 470 is combined with a Delrin® or HDPE cylindrical valve body, and both the opening and valve body 1000 are conically shaped. In such a valve arrangement, the valve will be able to provide leak-free shutoff with a gas or liquid at a pressure of up to 60 psi and a fluid flow path 65, 365 through the valve that has a diameter (in a direction normal to the longitudinal axis of the cylindrical valve body) of approximately 10% to 75% (in one preferable embodiment, 60%) of the diameter $D_v$ of the cylindrical body of the valve. Thus, in one embodiment, where the diameter $D_v$ of the cylindrical body of the valve is 0.27 inch, the fluid flow path may be as large as approximately 0.20 inch in a direction transverse to the longitudinal axis of the cylindrical valve body.

Despite having fluid flow paths with diameters that are nearly as large as the diameters $D_v$ of the valve bodies, valves of the aforementioned sizes, configurations and materials are advantageous because they are able to provide the aforementioned leak-free shutoff performance without employing o-rings or other separate sealing elements between the surfaces of the cylindrical openings 235, 240, 466, 470 and the cylindrical bodies of the valves 170, 175, 370, 373.

During assembly, the conical valve bodies 1000 are forced into the conical openings 235, 240, 466, 470 in the barrels to seat the valve bodies 1000 in said openings. For example, in one embodiment, conical valve bodies 1000 are forced into the conical openings in the barrels via a valve body insertion force of between approximately 5 pounds and approximately 10 pounds of force. As each valve body 1000 is forced into its respective opening 235, 240, 466, 470 in a barrel 66, 67, 367, 372, a retaining rim 1001 (see FIG. 33) snaps into place within a groove 1002 (see FIG. 28) in the opening. As a result, the valve body 1000 is retained in the opening 235, 240, 466, 470 via a press fit (i.e., the engagement between the rim 1001 and groove 1002). The press fit maintains a press fit force between the conical valve body 1000 and conical opening 235, 240, 466, 470 that provides a pressure between the abutting surfaces of the conical valve body 1000 and the conical opening 235, 240, 466, 470 that is between approximately 2.0 psi and approximately 45.0 psi.

Because of the aforementioned material combinations and the wedging effect of the conical surfaces when the valve bodies are forced into and maintained within the openings, the surface irregularities common to polymer parts are eliminated, thereby providing the fit between the valve bodies and valve seats that is necessary to provide the aforementioned leak-free performance without the use of o-rings or other separate sealing elements between the surfaces of the valve bodies and valve seats. In other words, the pressure between the abutting surfaces of the valve bodies and valve seats, as maintained via the press fit, forms or flattens away the surface irregularities that plague polymer parts. Because of the elimination of the surface irregularities, the diameter of the fluid flow path through the valve body can be a substantially larger percentage of the diameter $D_v$ of the valve body than would otherwise be possible, especially considering no o-rings are utilized. Thus, the valve arrangement of the subject invention provides for substantially greater flow rates as compared to similarly sized valve arrangements in the art.

In one version of each of the disclosed embodiments of the fluid coupling assembly 10, 310, the fluid flow path 65, 365 extending through the assembly will have a circular cross-section. In another version of each of the disclosed embodiments of the fluid coupling assembly, the fluid flow path 65, 365 will transition between circular cross-sections and non-circular cross-sections, as previously described in this Detailed Description.

d. Third Embodiment of the Quick Disconnect Coupling Assembly

Figure 44:
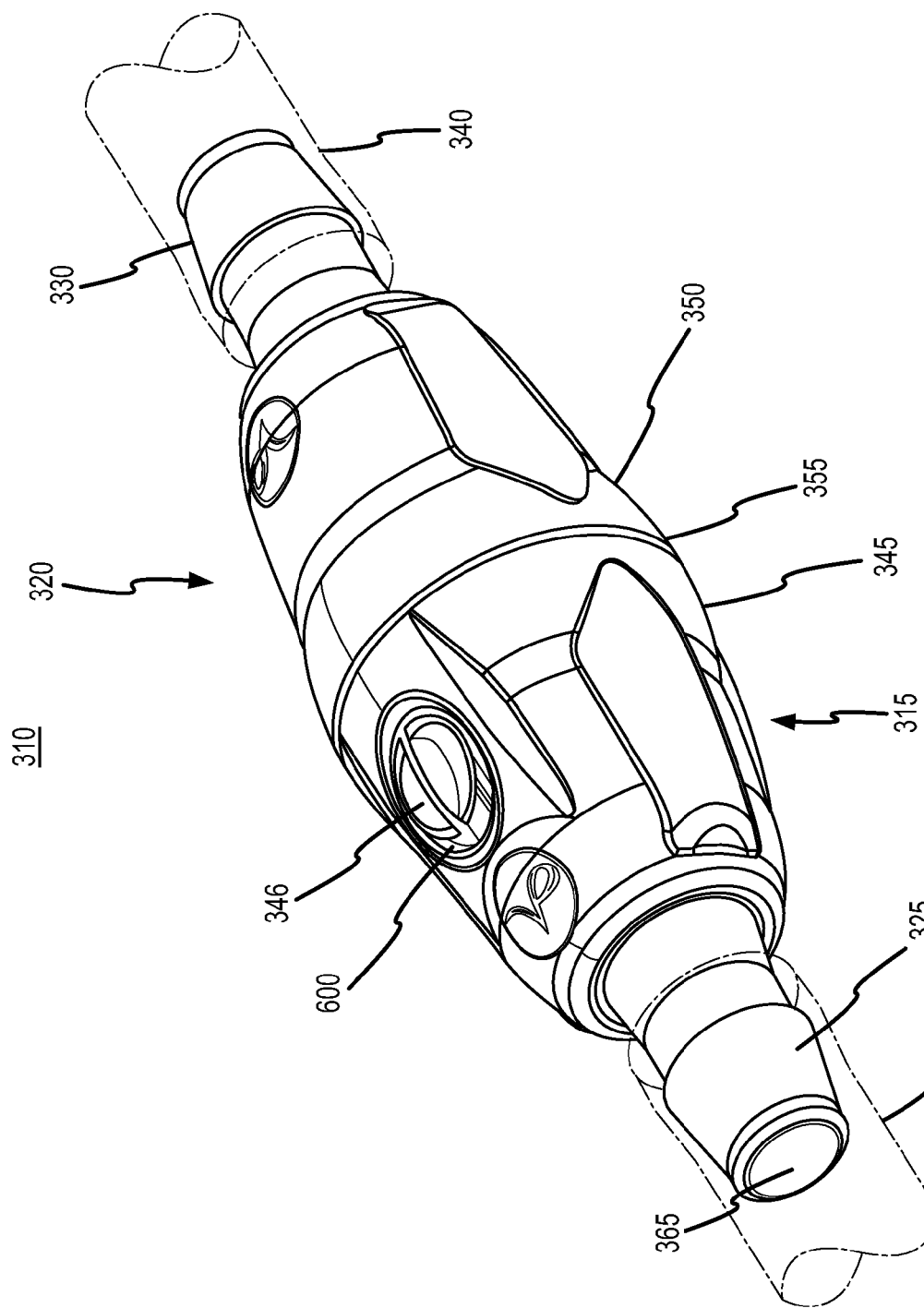
FIG. 44 is an isometric view of the quick disconnect coupling assembly, wherein the male coupler and female coupler are connected.
Figure 45:
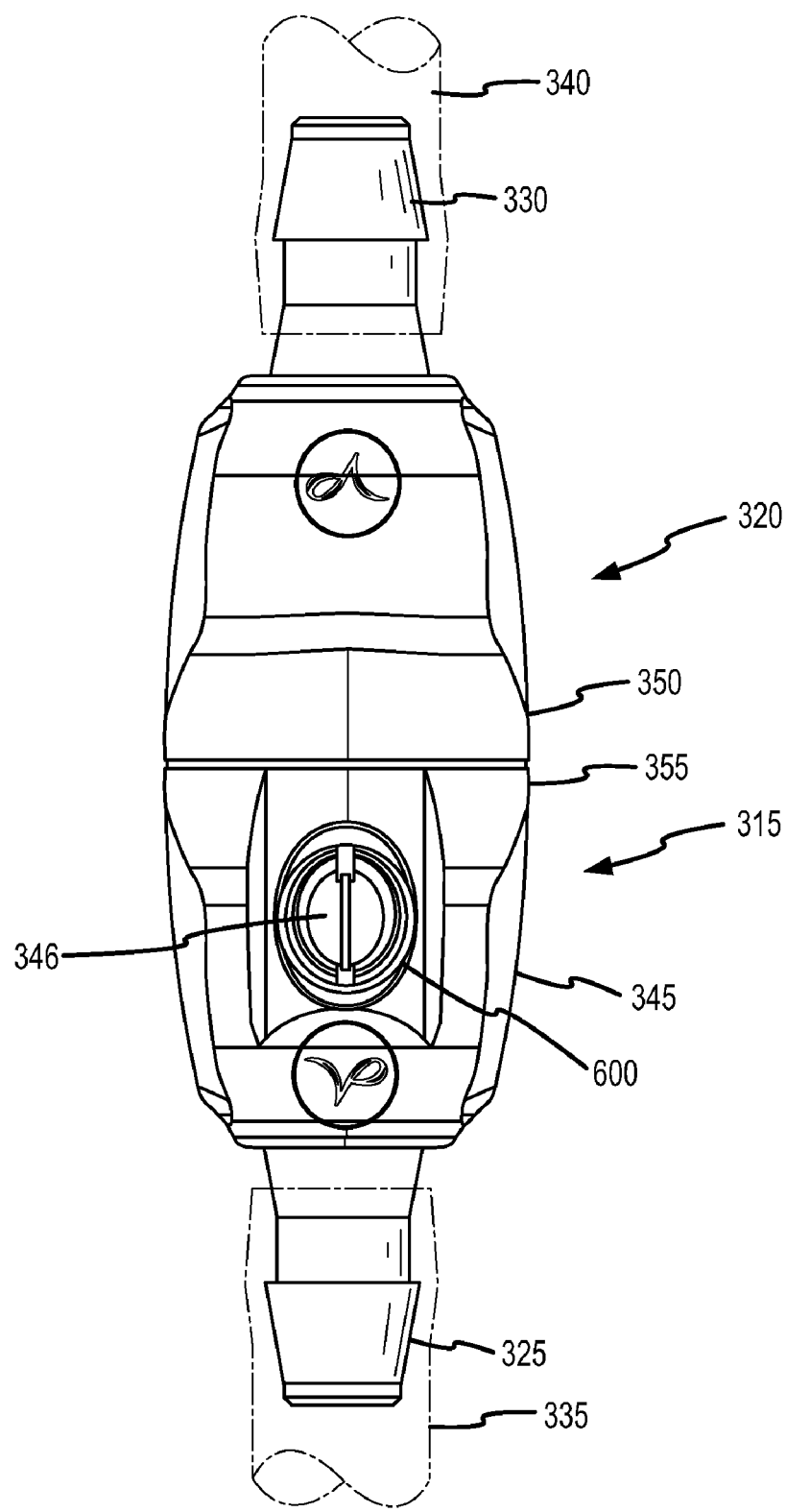
FIG. 45 is a top plan of the coupling assembly in the same connected state as depicted in FIG. 44.
Figure 46:
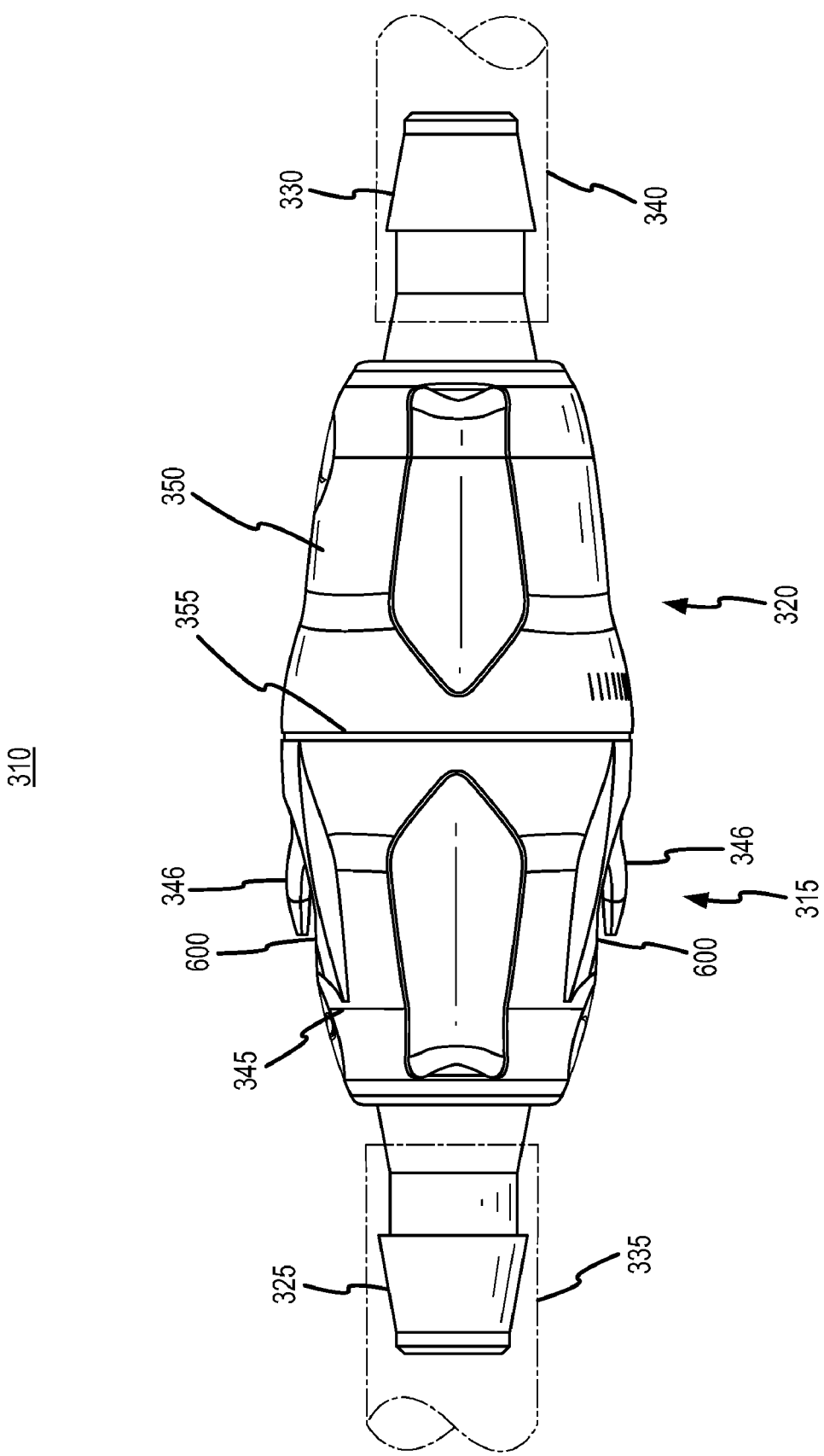
FIG. 46 is a side elevation of the coupling assembly in the same connected state depicted in FIG. 44.
Figure 47:
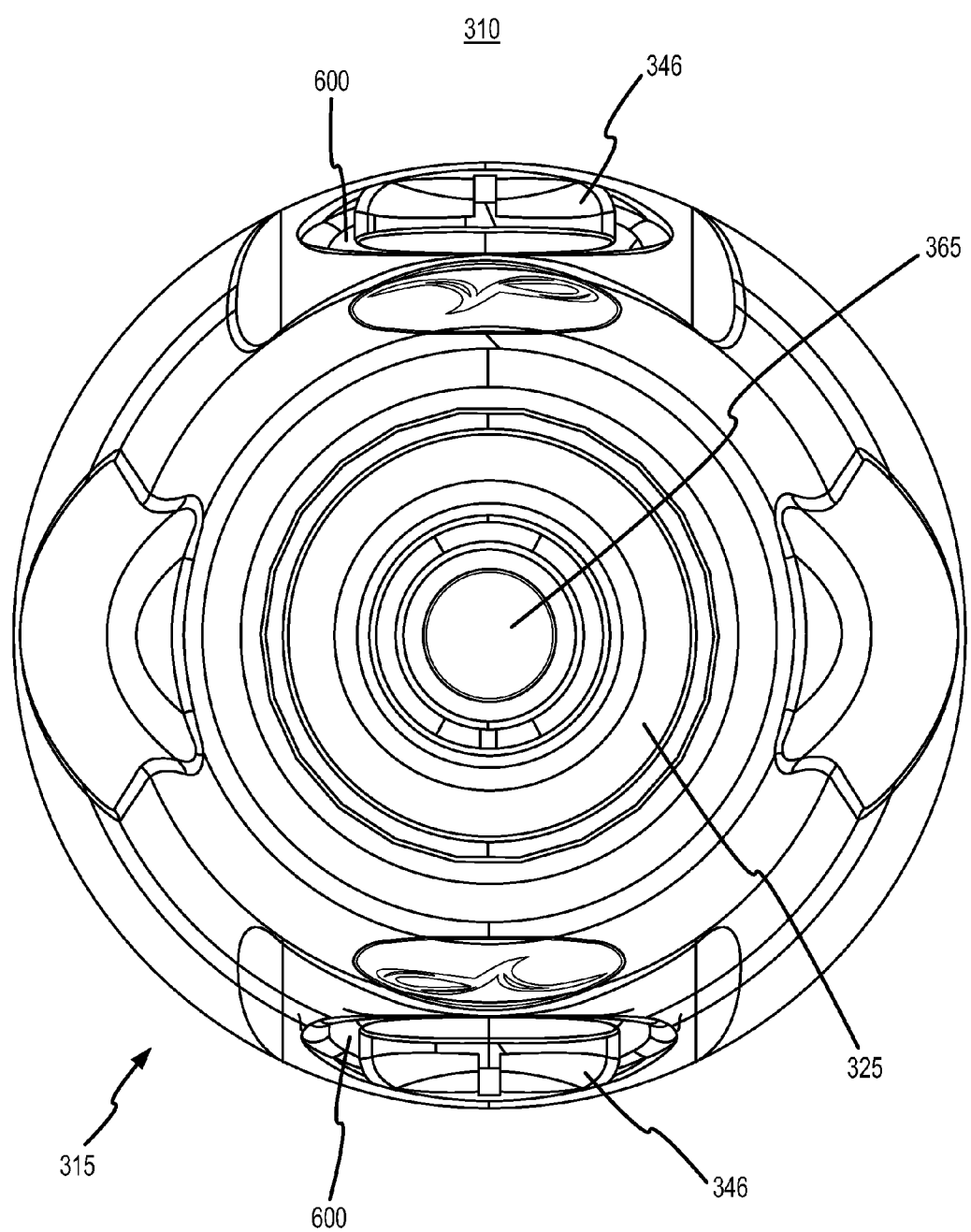
FIG. 47 is an end elevation of the coupling assembly in the same connected state depicted in FIG. 44 and as viewed from the male coupler end.
Figure 48:
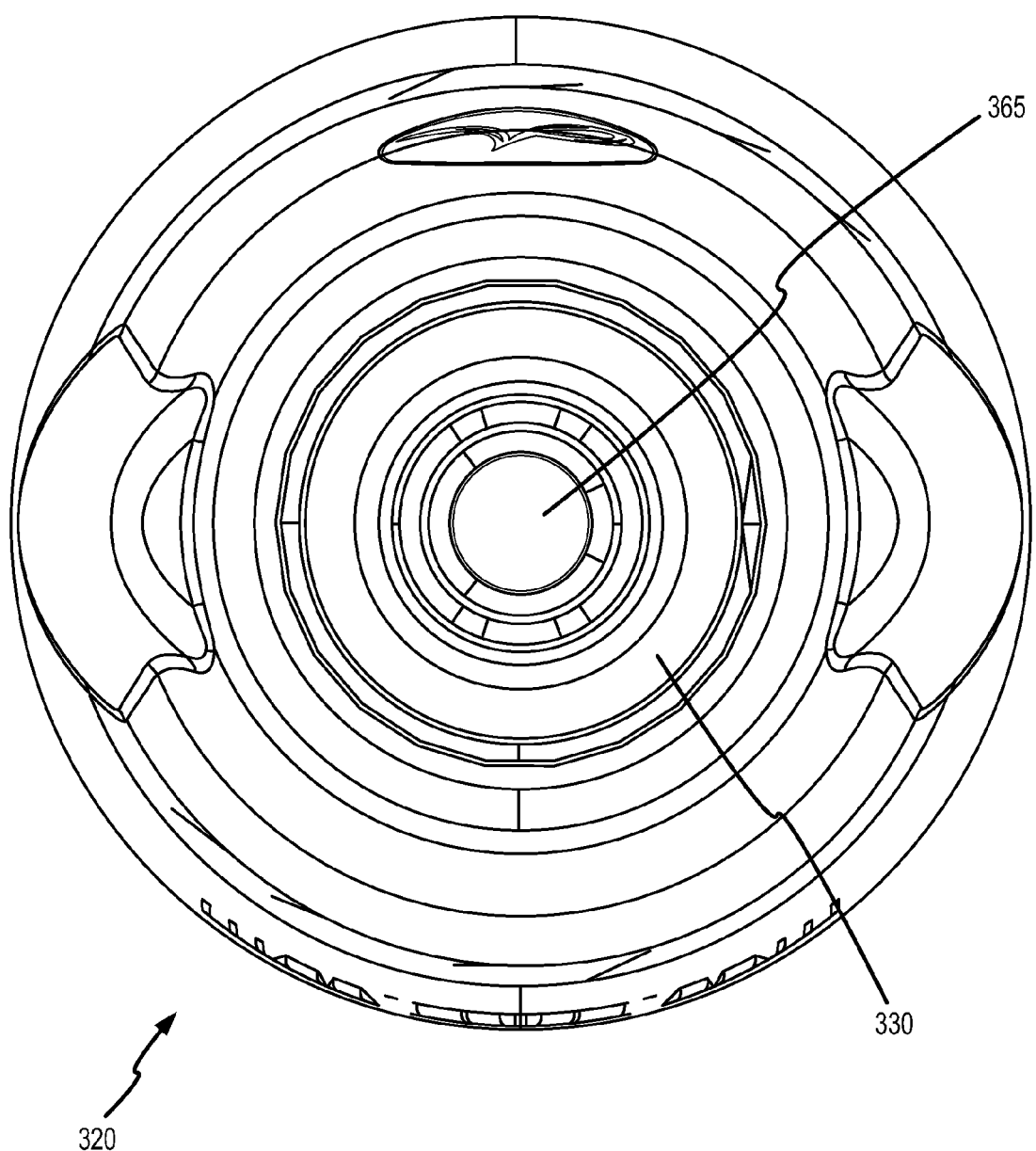
FIG. 48 is an end elevation of the coupling assembly in the same connected state depicted in FIG. 44 and as viewed from the female coupler end.
Figure 49:
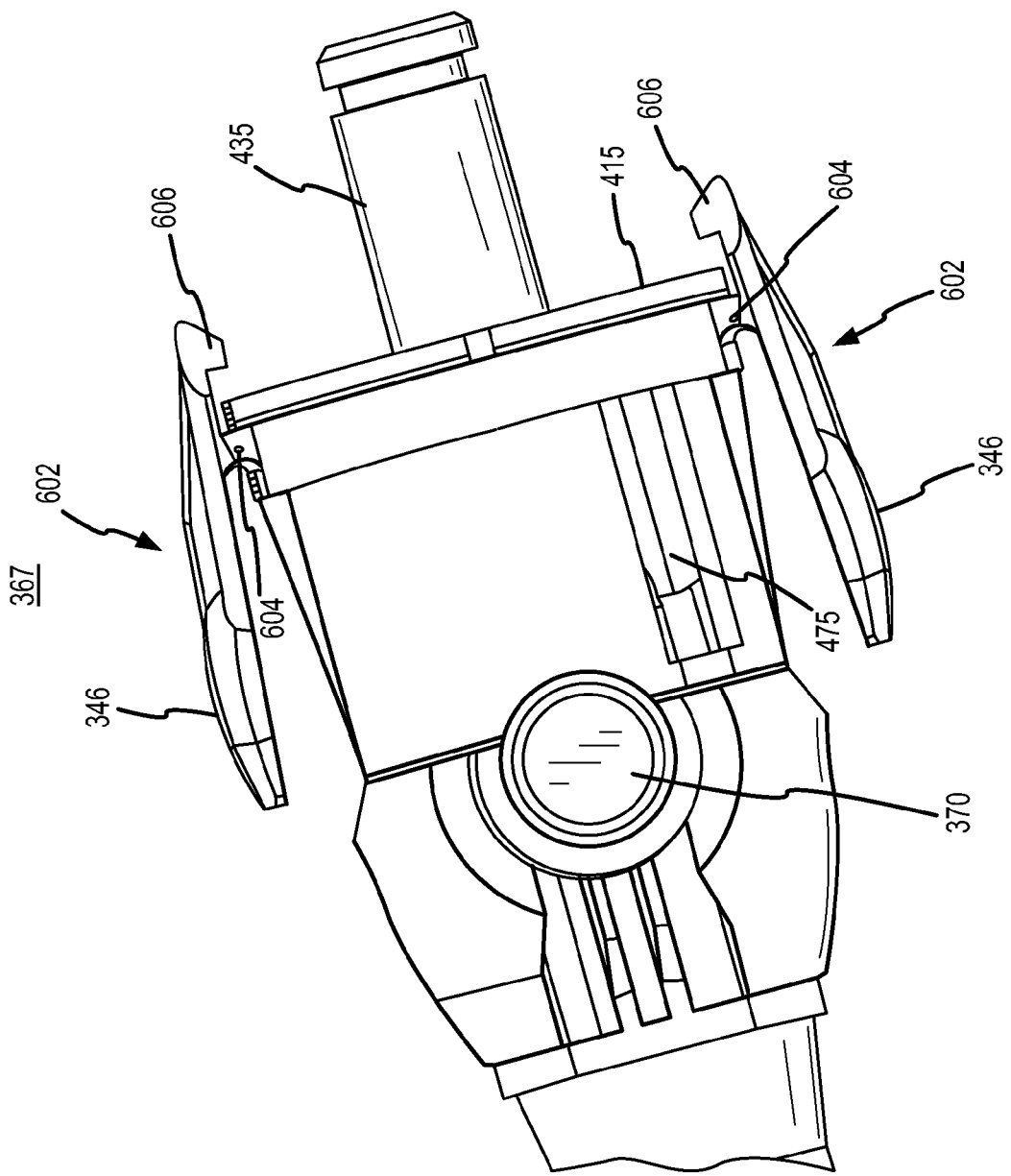
FIG. 49 is a side view of the male coupler with the male housing and the female coupler hidden to illustrate the engagement mechanism employed in the second version of the second embodiment of the coupling assembly.
Figure 50:
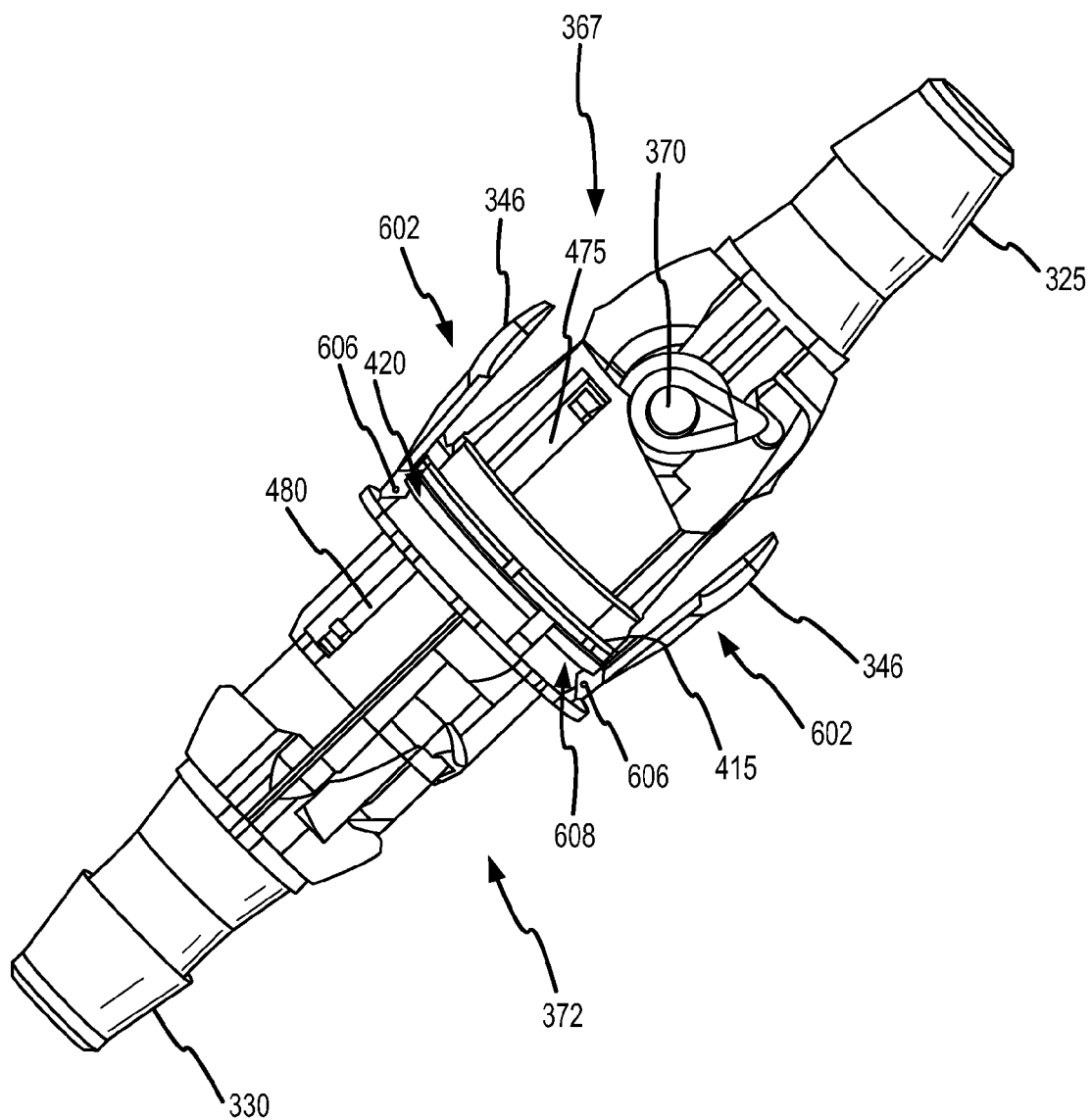
FIG. 50 is a side view of the coupling assembly that is generally similar to the side view depicted in FIG. 46, except the male and female housings are hidden to illustrate the engagement mechanism employed in the second version of the second embodiment of the coupling assembly.

A third embodiment of the quick disconnect coupling assembly 310 of the present invention is depicted in FIGS. 44-50. FIG. 44 is an isometric view of the quick disconnect coupling assembly 310, wherein the male coupler 315 and female coupler 320 are connected. FIG. 45 is a top plan of the coupling assembly 310 in the same connected state as depicted in FIG. 44. While a bottom plan of the coupling assembly 310 is not provided, it should be understood that it would appear identical to the view depicted in FIG. 44. FIG. 46 is a side elevation of the coupling assembly 310 in the same connected state depicted in FIG. 44. While a view of the opposite side of the coupling assembly 310 is not provided, it should be understood that it would appear identical to the view depicted in FIG. 46. FIG. 47 is an end elevation of the coupling assembly 310 in the same connected state depicted in FIG. 44 and as viewed from the male coupler end. FIG. 48 is an end elevation of the coupling assembly 310 in the same connected state depicted in FIG. 44 and as viewed from the female coupler end. FIG. 49 is a side view of the male coupler 315 with the male housing 345 and the female coupler 320 hidden to illustrate the engagement mechanism employed in the second version of the second embodiment of the coupling assembly 310. FIG. 50 is a side view of the coupling assembly that is generally similar to the side view depicted in FIG. 46, except the male and female housings 345, 350 are hidden to illustrate the engagement mechanism employed in the second version of the second embodiment of the coupling assembly 310.

With the exception of the appearance of the male and female housings 345, 350 and the engagement mechanism illustrated in FIGS. 49 and 50, the second version of the second embodiment of the coupling assembly 310 has the same features and operation (including with respect to the valves 370, 373 and the valve actuators 366, 371) as the first version of the second embodiment of the coupling assembly 310 depicted in FIGS. 21-43. Accordingly, the preceding discussion of the features and operation of the first version of the second embodiment of the coupling assembly 310, as depicted in FIGS. 21-43, should be considered equally applicable to the second version of the second embodiment depicted in FIGS. 44-50, except as noted in the following discussion pertaining to the engagement mechanism and overall appearance of the male and female housings 345, 350.

As shown in FIG. 44-46, the quick disconnect coupling assembly 310 includes a male coupler 315 and a female coupler 320. Each coupler 315, 320 includes a barbed end 325, 330 for insertion into, and connection with, a fluid conduit 335, 340 such as medical grade flexible tubing. Each coupler 315, 320 includes a housing or shroud 345, 350 that forms the exterior shell of each coupler 315, 320. When the couplers 315, 320 are connected, as depicted in FIGS. 44-46, the housings 345, 350 form a body that is semi-elliptical or egg-shaped as viewed from above, below or from the sides, as shown in FIGS. 45 and 46.

When the couplers 315, 320 are connected via the engagement mechanism described in the following discussion, the joining ends of the housings 345, 350 of the coupler 315, 320 abut along a seam 355 that circumferentially latitudinally extends about the exterior shell of the coupling assembly 310. The male coupling housing 345 includes a pair of holes 600 on opposite sides of the housing 345. A button 346 extends through each hole 600 in the male housing 345.

As illustrated in FIGS. 49 and 50, the male and female barrels 367, 372 have the same general configuration and appearance as the male and female barrels 367, 372 illustrated in FIGS. 27, 28, 30 and 31, except the male barrel 367 includes a pair of resilient latching fingers 602 that are positioned on opposite sides of the male barrel 367 and are pivotal about a pivot 604 that integrally extends from the male barrel 367 in the vicinity of the face plate 415. Each latching finger 602 includes a button 346 at its proximal end and an engagement or hook end 606 at its distal end.

As illustrated in FIG. 49, the latching fingers 602 are biased so the hook ends 606 are biased towards each other and the buttons 346 are biased away from each other. As indicated in FIG. 50, when the male and female barrels 367, 372 are pushed together in mating engagement, the hook ends 606 engage the faceplate 420 or groove feature 608 on the exterior of the female barrel 372. Thus, the engagement mechanism used to couple the male and female couplers 315, 320 to each other for the second version of the second embodiment depicted in FIGS. 44-50 are elements of the barrels 367, 372 that engage each other. This is unlike the engagement mechanism utilized in the first version of the second embodiment depicted in FIGS. 21-43, wherein elements of the male and female housings 345, 350 engage each other (see FIGS. 21-23, 26, 29, 39, 40 and 43).

As indicated in FIGS. 44-48, because of the bias of the latching fingers 602, the buttons 346 protrude from their respective holes 600 until depressed by a user's finger when trying to disengage the male and female couplers 315, 320. When the buttons 346 are depressed, the hook ends 606 are caused to pivot out of engagement with the faceplate 420 or groove feature 608 on the exterior of the female barrel 372, and the male and female couplers 315, 320 and be withdrawn from each other.

As can be understood from FIGS. 44, 47 and 48, a fluid flow path 365 extends through the coupler assembly 310 from the male coupler barbed end 325 to the female coupler barbed end 330. In one embodiment, the fluid flow path 365 of the coupler assembly 310 depicted in FIGS. 44-50 will be similar to the fluid flow path 365 depicted in FIGS. 24 and 25, wherein the fluid flow path 365 makes the following transitions as it extends through the coupler assembly from the male barbed end 325 to the female barbed end 330: circular cross-section 365a to a rectangular cross-section 365b to a circular cross-section 365a to a rectangular cross-section to a circular cross-section 365a. In another embodiment, the fluid flow path of the coupler assembly 310 depicted in FIGS. 44-50 will have a circular cross-section along the entire length of the coupler assembly 310.

In summary, the present invention, as disclosed in the embodiments depicted in FIGS. 1-20 and 21-43, is a fluid conduit coupling assembly 10, 310 comprising a first coupler 15, 315 and a second coupler 20, 320. The couplers 15, 315, 20, 320 are adapted to couple to each other. Each coupler 15, 315, 20, 320 includes a valve 170, 175, 370, 373 that is automatically caused to pivot from a closed position to an open position via the act of coupling together the couplers 15, 315, 20, 320. Decoupling the couplers 15, 315, 20, 320 results in the valves 170, 175, 370, 373 automatically pivoting closed, thereby providing a positive shutoff for each coupler 170, 175, 370, 373 when decoupled.

Figure 51:
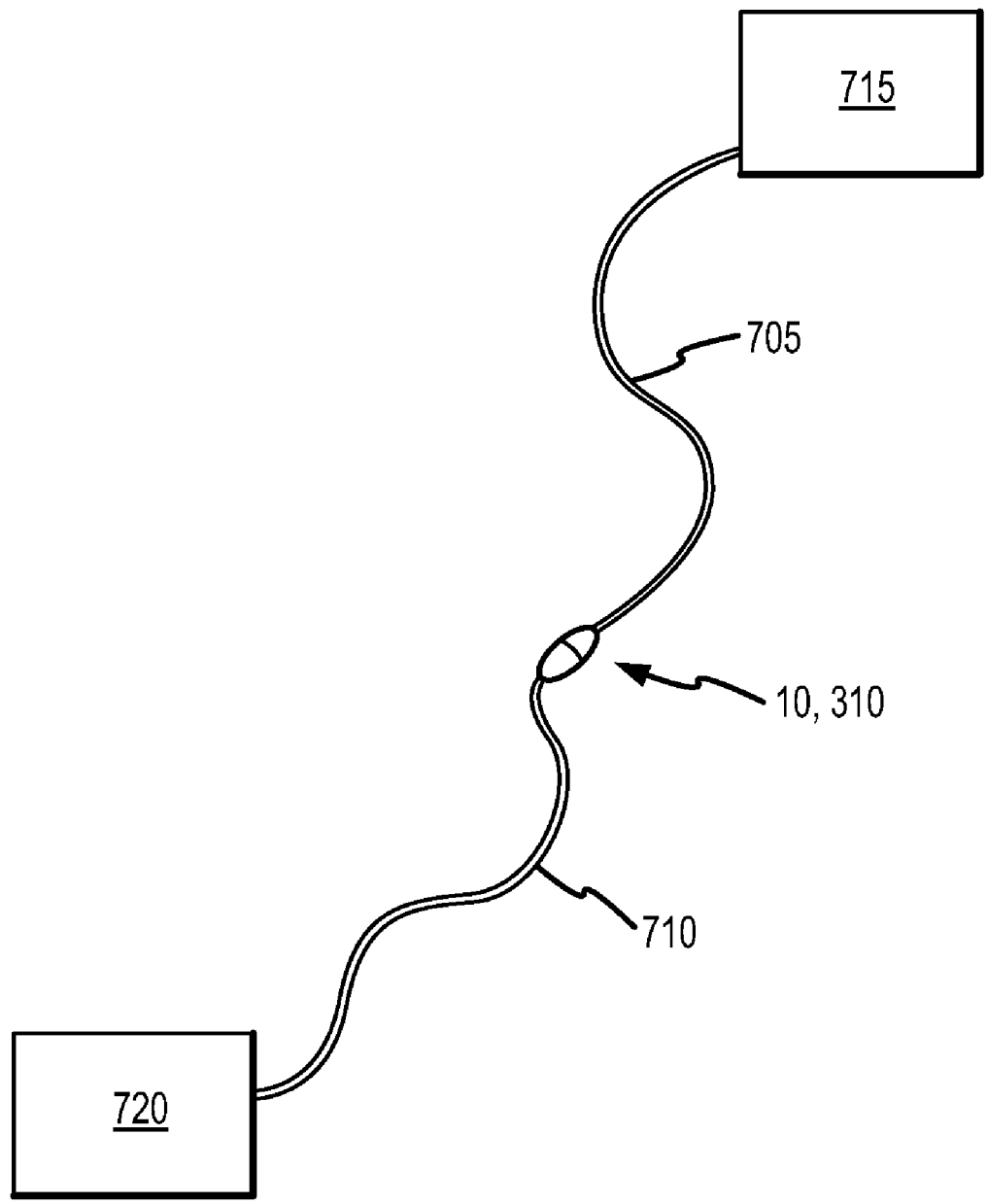
FIG. 51 is a schematic diagram of a fluid conduit coupling assembly of the subject invention being employed as part of a medical system.

As indicated in FIG. 51, in one embodiment the fluid conduit coupling assembly 10, 310 of the subject invention is utilized as part of a medical system 700 comprising the coupling assembly 10, 310, first and second fluid conduits 705, 710, a fluid origination point 715, and a fluid destination point 720. The coupling assembly 10, 310 joins the first fluid conduit 705 to the second fluid conduit 710. The first fluid conduit 705 extends between the coupling assembly 10, 310 and the fluid origination point 715. The second fluid conduit 710 extends between the coupling assembly 10, 310 and the fluid destination location 720. In one embodiment, the first and second fluid conduits 705, 710 are medical grade tubing. In one embodiment, the fluid origination point 715 is a first medical device or a first medical fluid reservoir 715. For example, in one embodiment, the fluid originating point 715 is an I.V. drip bag or other liquid reservoir whether the reservoir employs a rigid or flexible container, a blood pressure device, a medicament supplying device (e.g., insulin pump, etc.), a compressed gas source (e.g., compressed air system, oxygen system, carbon dioxide system, etc.), a medical treatment machine/device (e.g., a dialysis machine, etc.), a patient, or etc. In one embodiment, the fluid destination point 720 is a second medical treatment machine/device, a second medical fluid reservoir, or a patient 720. In one embodiment the fluid destination point 720 is a blood pressure cuff, a bladder or package, a reservoir for recirculation, collection vessels of all types, or etc.

The coupling assembly 10, 310 allows the fluid origination point 715 to be decoupled from the fluid destination point 720 with automatic positive shutoff. The coupling assembly 10, 310 also allows the fluid origination point 715 to be coupled with the fluid destination point 720 while automatically causing the two points 715, 720 to be placed in fluid communication.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the spirit or scope of this invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A fluid conduit coupling assembly comprising
a first coupler comprising
   a first attachment end defining a first fluid lumen and configured for attaching to a first fluid conduit;
   a first housing defining an inner cavity and including a cantilevered button defined within a wall of the first housing, wherein the cantilevered button is attached at a proximal end to the wall, is separated at lateral sides from the wall by slots, extends to a distal end congruent with a seam face of the first housing, and further comprises an engagement lip extending distally from the distal end and having a catch directed radially outward with respect to the first coupler, and wherein the slots are open to the inner cavity; and
   a first barrel substantially encompassed by the first housing and defining a first fluid path in fluid communication with the first fluid lumen in the first attachment end; and
a second coupler comprising a second attachment end defining a second fluid lumen and configured for attaching to a second fluid conduit;
   a second housing defining a ridge on an interior wall of the second housing for interfacing with the catch on the engagement lip on each of the cantilevered buttons; and
   a second barrel substantially encompassed by the second housing and defining a second fluid path in fluid communication with the second fluid lumen in the second attachment end;
   wherein when the first and second couplers are mated together, the catches on the pair of engagement lips operably connect with the ridge on the second housing, and
   the first fluid path of the first barrel is fluidly coupled with the second fluid path in the second barrel.

2. The fluid conduit coupling assembly of claim 1, wherein an outer surface of the cantilevered button is formed to provide a gripping surface for a user's fingers.

3. The fluid conduit coupling assembly of claim 1, wherein the first barrel and the first attachment end are an integrally formed structure; or
   the second barrel and the second attachment end are an integrally formed structure; or both.

4. The fluid conduit coupling assembly of claim 1, wherein one of the first barrel or the second barrel has an outer diameter that is substantially equivalent to an inner diameter of the other barrel whereby, when the first coupler engages the second coupler, the one of the first barrel or the second barrel is received within the other barrel and an interface between the outer diameter of the one of the first barrel or the second barrel and the inner diameter of the other barrel creates a seal between the first fluid path and the second fluid path.

5. The fluid conduit coupling assembly of claim 1, wherein
   a leading tip of the first barrel extends distally beyond the seam face of the first housing; or
   a leading tip of the second barrel extends distally beyond the seam face of the second housing; or both.

6. The fluid conduit coupling assembly of claim 1 further comprising
   a first valve housed within the first barrel and interposed between the first fluid path and the first fluid lumen in the first attachment end; and
   a second valve housed within the second barrel and interposed between the second fluid path and the first fluid lumen in the first attachment end; wherein
   the first valve and the second valve are in a closed configuration when the first coupler is disconnected from the second coupler to prevent fluid flow from the first fluid lumen to the first fluid path and from the second fluid lumen to the second fluid path, respectively; and
   the first valve and the second valve are actuated to an open configuration when the first coupler is connected with the second coupler to allow fluid flow between the first fluid lumen, the first fluid path, the second fluid path, and the second lumen.

7. The fluid conduit coupling assembly of claim 6 further comprising
   a first valve actuation member in contact with the first valve;
   a second valve actuation member in contact with the second valve, wherein either the first valve actuation member, the second valve actuation member, or both, defines a groove in an outer wall thereof; and
   at least one latch extending distally from either the first valve actuation member, the second valve actuation member, or both, respectively; wherein
   when the first and second couplers are mated together the at least one latch mates with the groove; and
   the first and second valve actuation members open the first and second valves, respectively, such that the first and second fluid paths are joined.

8. The fluid conduit coupling assembly of claim 7 further comprising a plurality of latches extending distally from one of the first or second valve actuation members for connection with the groove in the other of the first or second valve actuation members.

9. The fluid conduit coupling assembly of claim 7 further comprising
a first biasing member that biases the first valve actuation member in a position that holds the first valve in a closed position; and
a second biasing member that biases the second valve actuation member in a position that holds the second valve in a closed position.

10. The fluid conduit coupling assembly of claim 7, wherein
the first valve actuation member encompasses and translates along a portion of the first barrel as the first and second couplers are connected and disconnected; and
the second valve actuation member encompasses and translates along a portion of the second barrel as the first and second couplers are connected and disconnected.

11. The fluid conduit coupling assembly of claim 1, wherein the at least one cantilevered button comprises a pair of cantilevered buttons.

12. The fluid conduit coupling assembly of claim 11, wherein each of the cantilevered buttons is located symmetrically opposite from the other on the first housing.

13. A fluid conduit coupling assembly comprising
a male coupler comprising
a first barbed fitting configured for attachment with a first fluid conduit;
a male housing attached to the first barbed fitting and further defining an inner cavity and including a pair of depressible latch mechanisms disposed at a mating end of the male housing, wherein the male housing defines slots that define lateral sides of each depressible latch mechanism, and wherein the slots are open to the inner cavity;
an elongated male fluid port extending from within the male housing toward the mating end and in fluid communication with the first barbed fitting; and
a female coupler comprising
a second barbed fitting configured for attachment with a second fluid conduit;
a female housing defining an engagement feature on an interior wall adjacent a mating end of the female housing; and
an elongated female fluid port extending from within the female housing toward the mating end and in fluid communication with the second barbed fitting;
wherein when the male coupler is connected to the female coupler,
a portion of the depressible latch mechanism enters the female housing and operably connects with the engagement feature on the interior wall thereof to hold the male and female couplers together; and
the elongated male fluid port is received within the elongated female fluid port to create a fluid pathway from the first barbed fitting, through the elongated male and female ports, and through the second barbed fitting.

14. The fluid conduit coupling assembly of claim 13, wherein each of the depressible latch mechanisms comprises a cantilevered button that further has an engagement lip extending therefrom.

15. The fluid conduit coupling assembly of claim 14, wherein each engagement lip further comprises a catch directed radially outward with respect to a center axis of the male coupler.

16. The fluid conduit coupling assembly of claim 13, wherein the engagement feature is a ridge on the interior wall of the female housing.

17. The fluid conduit coupling assembly of claim 13, wherein a leading tip of the elongated male fluid port extends distally beyond a seam face of the male housing.

18. The fluid conduit coupling assembly of claim 13, wherein a leading tip of the elongated female fluid port extends distally beyond a seam face of the female housing.

19. The fluid conduit coupling assembly of claim 13, wherein each of the depressible latch mechanisms is located symmetrically opposite from the other on the male housing.

20. The fluid conduit coupling assembly of claim 13, wherein an outer surface of each of the depressible latch mechanisms is formed to provide a gripping surface for a user's fingers.

21. The fluid conduit coupling assembly of claim 13, wherein
the elongated male fluid port and the first barbed fitting are an integrally formed structure; and
the elongated female fluid port and the second barbed fitting are an integrally formed structure.

22. The fluid conduit coupling assembly of claim 13 further comprising
a first valve disposed between the elongated male fluid port and the first barbed fitting; and
a second valve disposed between the elongated female fluid port and the second barbed fitting; wherein
the first valve and the second valve are in a closed configuration when the male and female couplers are disconnected; and
the first valve and the second valve are in an open configuration when the male coupler is connected to the female coupler.

* * * * *